US008530408B2

(12) United States Patent
Davydov et al.

(10) Patent No.: US 8,530,408 B2
(45) Date of Patent: Sep. 10, 2013

(54) SUBSTRATES OF N-END RULE UBIQUITYLATION AND METHODS FOR MEASURING THE UBIQUITYLATION OF THESE SUBSTRATE

(75) Inventors: Ilia Davydov, North Potomac, MD (US); John H. Kenten, Boyds, MD (US); Hans Biebuyck, Rockville, MD (US); Pankaj Oberoi, Rockville, MD (US)

(73) Assignee: Meso Scale Technologies LLC, Gaithersburg, MD (US)

( * ) Notice: Subject to any disclaimer, the term of this patent is extended or adjusted under 35 U.S.C. 154(b) by 347 days.

(21) Appl. No.: 12/606,787

(22) Filed: Oct. 27, 2009

(65) Prior Publication Data
US 2010/0048485 A1 Feb. 25, 2010

Related U.S. Application Data

(62) Division of application No. 10/693,999, filed on Oct. 28, 2003, now Pat. No. 7,608,682.

(60) Provisional application No. 60/422,448, filed on Oct. 30, 2002, provisional application No. 60/486,529, filed on Jul. 12, 2003.

(51) Int. Cl.
*C07K 14/00* (2006.01)
(52) U.S. Cl.
USPC .............................................. 514/2; 530/300
(58) Field of Classification Search
None
See application file for complete search history.

(56) References Cited

U.S. PATENT DOCUMENTS

| 6,165,731 A | 12/2000 | Deshaies et al. |
| 6,207,369 B1 | 3/2001 | Wohlstadter et al. |
| 6,413,725 B1 | 7/2002 | Deshaies et al. |
| 6,426,205 B1 | 7/2002 | Tyers et al. |
| 6,589,746 B1 * | 7/2003 | Zemlan ........................ 435/7.1 |
| 7,608,682 B2 | 10/2009 | Davydov et al. |
| 2002/0025569 A1 | 2/2002 | Caligiuri et al. |
| 2003/0003460 A1 | 1/2003 | Sigal et al. |
| 2003/0113713 A1 | 6/2003 | Glezer et al. |
| 2003/0124572 A1 | 7/2003 | Umek et al. |
| 2003/0175679 A1 | 9/2003 | Thomas et al. |
| 2003/0207290 A1 | 11/2003 | Kenten et al. |
| 2004/0137597 A1 | 7/2004 | Davydov et al. |

FOREIGN PATENT DOCUMENTS

| EP | 1182458 | 2/2000 |
| WO | 03/001889 | 1/2003 |
| WO | 03/022028 | 3/2003 |

OTHER PUBLICATIONS

Reiss et al.,"Specificity of Binding of NH2-terminal Residue of Proteins to Ubiquitin-Protein Ligase", The Journal of Biological Chemistry, vol. 263, No. 6, pp. 2693-2698, 1988.*

Amano et al. "Thyroid hormone regulation of a transcriptional coactivator in *Xenopus laevis*: Implication for a role in postembryonic tissue remodeling" Developmental Dynamics 223:526-535 2002.
Artavanis-Tsakonas et al. "Notch signaling" Science 268:225-232 (1995).
Brenner "Hint, Fhit, and GalT: Function, structure, evolution, and mechanim of three branches of the histidine triad superfamily of nucleotide hydrolases and transferases" Biochemistry 41:9003-9014 (2002).
Brzovic et al. "The cancer-predisposing mutation C61G disrupts homodimer formation in the $NH_2$-terminal BRCA1 Ring finger domain" J. Biol. Chem. 273:7795-7799 (1998).
Bustin et al. "Expression of HMG chromosomal proteins during cell cycle and differentiation" Crit. Rev. Eukar. Gene Exp. 2:137-143 (1992).
Bustin et al. "High-mobility-group chromosomal proteins: Architectural components that facilitate chromatin function" Prog. Nucl. Acid Res. Mol. Biol. 54:35-100 1996.
Clay-Farrace et al. "Human replication protein Cdc6 prevents mitosis through a checkpoint mechanism that implicates Chk1" EMBO J. 22:704-712 (2003).
Coleman "The 3 Rs of Cdc6: Recruitment, regulation, and replication" Curr. Biol. 12:R759 (2002).
Compton et al. "The analysis of cThy28 expression in avian lymphocytes" Apoptosis 6:299-314 (2001).
Date et al. "Early-onset ataxia with ocular motor apraxia and hypoalbuminemia is caused by mutations in a new HIT superfamily gene" Nature Genetics 29:184-188 (2001).
Davydov et al. "RGS4 is arginylated and degraded by the N-end rule pathway in vitro" J. Biol. Chem. 275:22931-22941 (2000).
De Groot et al. "Sindbis virus RNA polymerase is degraded by the N-end rule pathway" Proc. Natl. Acad. Sci. USA 88:8967-8971 (1991).
Delmolino et al. "Multiple mechanisms regulate subcellular localization of human CDC6" J. Biol. Chem. 276:26947-26954 (2001).
Ditzel et al. " Degradation of DIAP1 by the N-end rule pathway is essential for regulating apoptosis" Nature Cell Biol. 5:467-473 (2003).
Durocher et al. "The molecular basis of FHA domain: Phosphopeptide binding specificity and implications for phospho-dependent signaling mechanisms" Mol. Cell 6:1169-1182 (2000).
Ebneth et al. "Overexperssion of Tau protein inhibits kinesin-dependent trafficking of vesicles, mitochondria and endoplasmic reticulum: Implications for Alzheimer's disease" J. Cell Biol. 143:777-794 (1998).
Einck et al. "Inhibition of transcription in somatic cells by microinjection of antibodies to chromosomal proteins" Proc. Natl. Acad. Sci. USA 80:6735-6739 (1983).

(Continued)

*Primary Examiner* — Anand Desai
(74) *Attorney, Agent, or Firm* — Nixon Vanderhye PC

(57) ABSTRACT

The present invention relates to methods, compositions, compounds and kits for detecting, measuring and modulating protein ubiquitylation via the N-end rule pathway and for identifying novel substrates, enzymes and modulators of N-end rule ubiquitylation. The present invention also relates to specific substrates of N-end rule ubiquitylation as well as activated fragments of these substrates, proteases that expose N-degrons in these substrates, ubiquitin ligases that ubiquitylate these substrates and inhibitors of the ubiquitylation of these substrates.

4 Claims, 11 Drawing Sheets

(56) References Cited

OTHER PUBLICATIONS

Elsasser et al. "Phosphorylation controls timing of Cdc6p destruction: A biochemical analysis" Mol. Biol. cell 10:3263-3277 (1999).
Eng et al. "Glial fibrillary acidic protein: GFAP—thirty-one years (1969-2000)" Neurochem. Res. 25:1439-1451 (2000).
Gerdes et al. "Production of a mouse monoclonal antibody reactive with a human nuclear antigen associated with cell proliferation" Int. J. Cancer 31:13-20 (1983).
Goedert et al. "Multiple isoforms of human microtubule-associated protein Tau: Sequences and localization in neurofibrillary tangles of Alzheimer's disease" Neuron 3:519-526 (1989).
Golbe et al. "The Tau A0 allele in Parkinson's disease" Movement Disorders 16:442-447 (2001).
Guglielmi et al. "The yeast homolog of human PinX1 is involved in rRNA and small nucleolar RNA maturation, not in telomere elongation inhibition" J. Biol. Chem. 277:35712-35719 (2002).
Han et al. "Activation of the transcription factor MEF2C by the MAP kinase p38 in inflammation" Nature 386:296-299 (1997).
Hateboer et al. "Cell cycle-regulated expression of mammalian CDC6 is dependent on E2F" Mol. Cell. Biol. 18:6679-6697 (1998).
Hershko et al. "The ubiquitin system" Annu. Rev. Biochem. 67:425-479 (1998).
Hsieh et al. "CIR, a corepressor linking the DNA binding factor CBF1 to the histone deacetylase complex" Proc. Natl. Acad. Sci. USA 96:23-28 (1999).
Hwang et al. "A conserved RING finger protein required for histone H2B monoubiquitination and cell size control" Mol. Cell 11:261-266 (2003).
Ito et al. "Immunohistochemical localization of the nucleosome-binding protein HMGN3 in mouse brain" J. Histochem. & Cytochem. 50:1273-1275 (2002).
Jiang "Degrading Ci: Who is cul-pable?" Genes & Development 16:2315-2321 (2002).
Joazeiro et al. "The tyrosine kinase negative regulator c-Cbl as a RING-type, E2-dependent ubiquitin-protein ligase" Science 286:309-312 (1999).
Johnson et al. "Tau, where are we now?" J. Alzeimer's Dis. 4:375-398 (2002).
Kishi et al. "A critical role in Pin2/TRF1 in ATM-dependent regulation" J. Biol. Chem. 277:7420-7429 (2002).
Kishino et al. "UBE3A/E6-AP mutations cause Angelman syndrome" Nature Genetics 15:70-73 (1997).
Kleinschmidt et al. "Structure of nucleosome core particles containing uH2A (A24)" Nucl. Acids Res. 9:2423-2431 (1981).
Kosik et al. "Developmentally regulated expression of specific Tau sequences" Neuron 2:1389-1397 (1989).
Kuroda et al. "The Slp homology domain of synaptotagmin-like proteins 1-4 and Slac2 functions as a novel Rab27A binding domain" J. Biol. Chem. 277:9212-9218 (2002).
Kurz et al. "Cytoskeletal regulation by the Nedd8 ubiquitin-like protein modification pathway" Science 295:1294-1298 (2002).
Kwon et al. "Construction and analysis of mouse strains lacking the ubiquitin ligase UBR1 (E3α) of the N-end rule pathway" Mol. Cell. Biol. 21:8007-8021 (2001).
Kwon et al. "Bivalent inhibitor of the N-end rule pathway" J. Biol. Chem. 274:18135-18139 (1999).
Landsman et al. "Chromosomal protein HMG-17" J. Biol. Chem. 261:7479-7484 (1986).
Lecker et al. "Ubiquitin conjugation by the N-end rule pathway and mRNAs for its components increase in muscles of diabetic rats" J. Clin. Invest. 104:1411-1420 (1999).
Lee et al. "Two classes of proteins dependent on either the presence or absence of thyroid hormone for interaction with the thyroid hormone receptor" Mol. Endocrinol. 9:243-254 (1995).
Lu et al. "Competition for microtubule-binding with dual expression of Tau missense and splice isoforms" Mol. Biol. Cell 12:171-184 (2001).
Maeda et al. "In vitro ubiquitination of cyclin D1 and ROC1-CUL1 and ROC1-CUL3" FEBS Letters 494:181-185 (2001).
Mandelkow et al. "On the structure of microtubules, Tau, and paired helical filaments" Neurobiol. Aging 16:347-354 (1995).
Miyaji et al. "Molecular cloning and characterization of the mouse thymocyte protein gene" Gene 297:189-196 (2002).
Moreira et al. "The gene mutated in ataxia-ocular apraxia 1 encodes the new HIT/Zn-finger protein aprataxin" Nature Genetics 29:189-193 (2001).
Morishima-Kawashima et al. "Ubiquitin is conjugated with amino-terminally processed tau in paired helical filaments" Neuron. 10:1151-1160 (1993).
Mufson et al. "Gene expression profiles of cholinergic nucleus basalis neurons in Alzheimer's disease" Neurochem. Res. 27:1035-1048 (2002).
O'Connor et al. "Synaptic vesicle fusion and synaptotagmin: 2B or not 2B?" Nature Neurosci. 5:823-824 (2002).
Ohta et al. "Cdc6 expression as a marker of proliferative activity in brain tumors" Oncology Reports 8:1063-1066 (2001).
Ohtani et al. "Regulation of cells growth-dependent expression of mammalian CDC6 gene by the cell cycle transcription factor E2F" Oncogene 17:1777-1785 (1998).
Ou et al. "Distinct protein degradation mechanisms mediated by Cul1 and Cul3 controlling Ci stability in *Drosophila* eye development" Genes & Development 16:2403-2414 (2002).
Pallanck et al. "A tale of two $C_2$ domains" Trends Neurosci. 26:2-4 (2003).
Pash et al. "Aberrant expression of high mobility group chromosomal protein 14 affects cellular differentiation" J. Biol. Chem. 268:13632-13638 (1993).
Pash et al. "Chromosomal protein HMG-14 is overexpressed in down syndrome" Exp. Cell Res. 193:232-235 (1991).
Pickart et al. "Mechanisms underlying ubiquitination" Annu. Rev. Biochem. 70:503-533 (2001).
Porkka et al. "A fragment of the HMGN2 protein homes to the nuclei of tumor cells and tumor endothelial cells in vivo" Proc. Natl. Acad. Sci. USA 99:7444-7449 (2002).
Rao et al. "Degradation of a cohesin subunit by the N-end rule pathway is essential for chromosome stability" Nature 410:955-959 (2001).
Reiss et al. "Affinity purification of ubiquitin-protein ligase on immobilized protein substrates" J. Biol. Chem. 265:3685-3690 (1990).
Rickman et al. "Mechanism of calcium-independent synaptotagmin binding to target" J. Biol. Chem. 278:5501-5504 (2002).
Robles et al. "Down-regulation of Cdc6, a cell cycle regulatory gene, in prostate cancer" J. Biol. Chem. 277:25431-25438 (2002).
Shimazaki et al. "Early-onset ataxia with ocular motor apraxia and hypoalbuminemia" Neurol. 59:590-595 (2002).
Shimura et al. "Familial Parkinson disease gene product, parkin, is a ubiquitin-protein ligase" Nature Genetics 25:302-305 (2000).
Singer et al. "Cullin-3 targets cyclin E for ubiquitination and controls S phase in mammalian cells" Genes & Development 13:2375-2387 (1999).
Solomon et al. "Rates of ubiquitin conjugation increase when muscles atrophy, largely through activation of the N-end rule pathway" Proc. Natl. Acad. Sci. USA 95:12602-12607 (1998).
Strom et al. "A family of Rab27-binding proteins" J. Biol. Chem. 277:25423-25430 (2002).
Thapar et al. "Proliferative activity and invasiveness among pituitary adenomas and carcinomas: an analysis using the MIB-1 antibody" Neuro. Surgery 38:99-107 (1996).
Turner et al. "Peptides accelerate their uptake by activating a ubiquitin-dependent proteolytic pathway" Nature 405:579-583 (2000).
Varshaysky "The ubiquitin system" Trends Biochem. Sci. 22:383-387 (1997).
Varshaysky "The N-end rule: Functions, mysteries, uses" Proc. Natl. Acad. Sci. USA 93:12142-12149 (1996).
Varshaysky "The N-end rule and regulation of apoptosis" Nature Cell Biol. 5:373-376 (2003).
Weissman "Themes and variations on ubiquitylation" Nature Rev. Mol. Cell Biol. 2:169-178 (2001).
Williams et al. "Improved cervical smear assessment using antibodies against proteins that regulate DNA replication" Proc. Natl. Acad. Sci. USA 95:14932-14937 (1998).

Winston et al. "Culprits in the degradation of cylin E apprehended" Genes & Development 13:2751-2757 (1999).

Woods et al. "Regulation of p53 function" Exp. Cell Res. 264:56-66 (2001).

Yam et al, "Cyclin a in cell cycle control and cancer" Cell. Mol. Life Sci. 59:1317-1326 (2002).

Yan et al. "PR48, a novel regulatory subunit of protein phosphatase 2A, interacts with Cdc6 and modulates DNA replication in human cells" Mol. Cell. Biol. 20:1021-1029 (2000).

Yang et al. "Ubiquitin protein ligase activity of IAPs and their degradation in proteasomes in resposne to apoptotic stimuli" Science 288:874-877 (2000).

Yoshihara et al. "Synaptotagmin I functions as a calcium sensor to synchronize neurotransmitter release" Neuron 36:897-908 (2002).

Zhen et al. "The Pin2/TRF1-interacting protein PinX1 is a potent telomerase inhibitor" Cell 107:347-359 (2001).

Zhou et al. A role for SKIP in EBNA2 activation of CBF1-repressed promoters J. Virol. 74:1939-1947 (2000).

International Search Report for PCT/US2003/34148 mailed Dec. 20, 2004.

International Preliminary Examination Report for PCT/US2003/34148 mailed May 5, 2005.

* cited by examiner

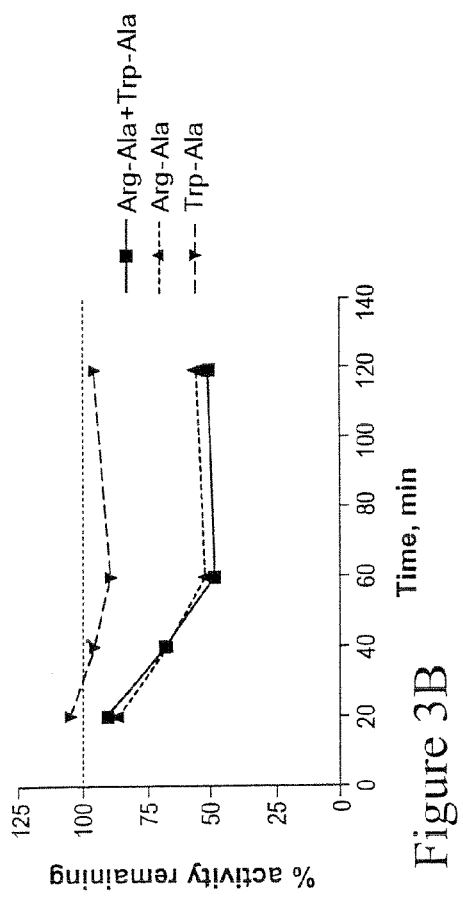
Figure 3B
Figure 3A
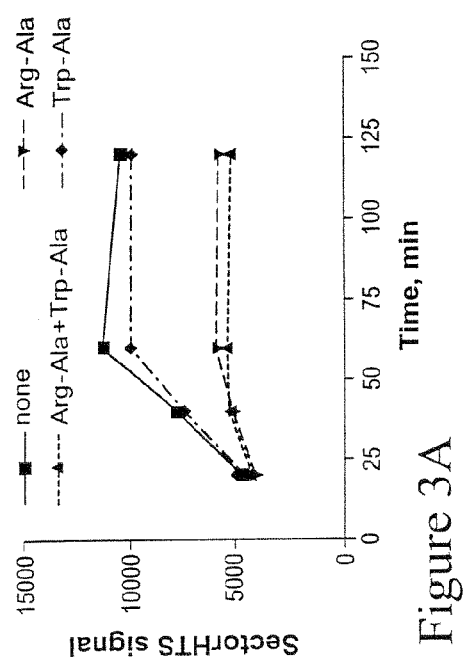
Figure 3C
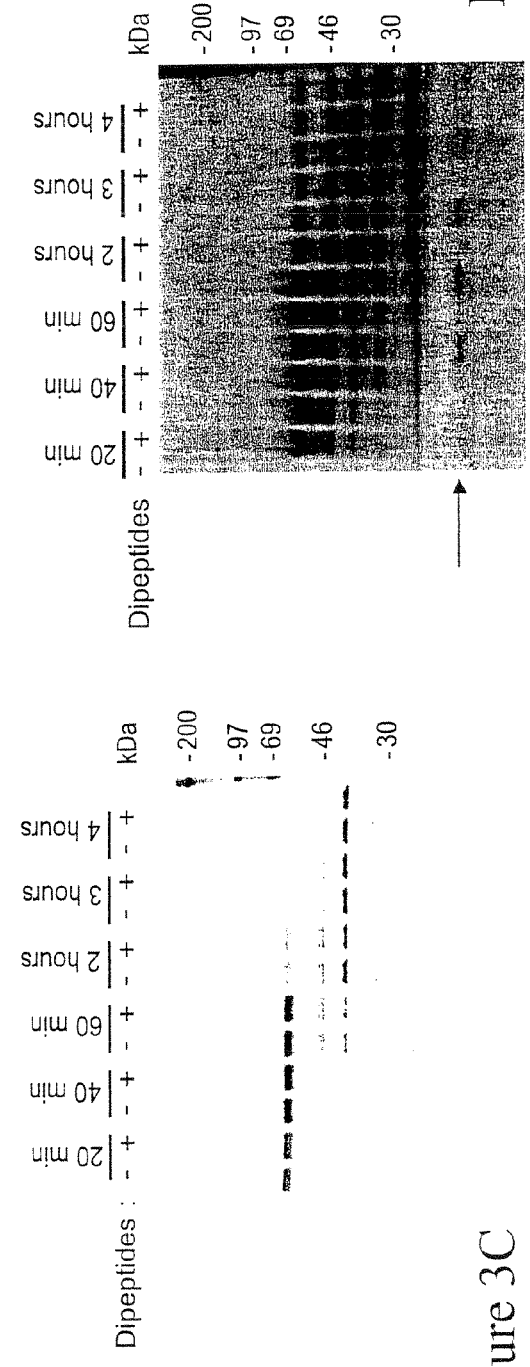
Figure 3D

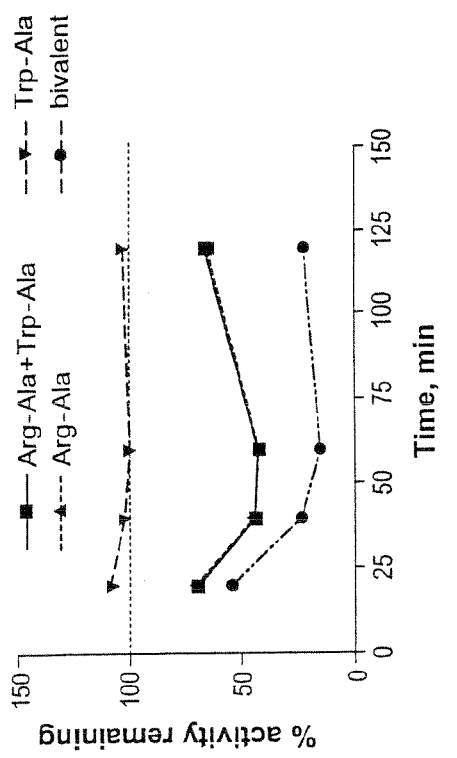
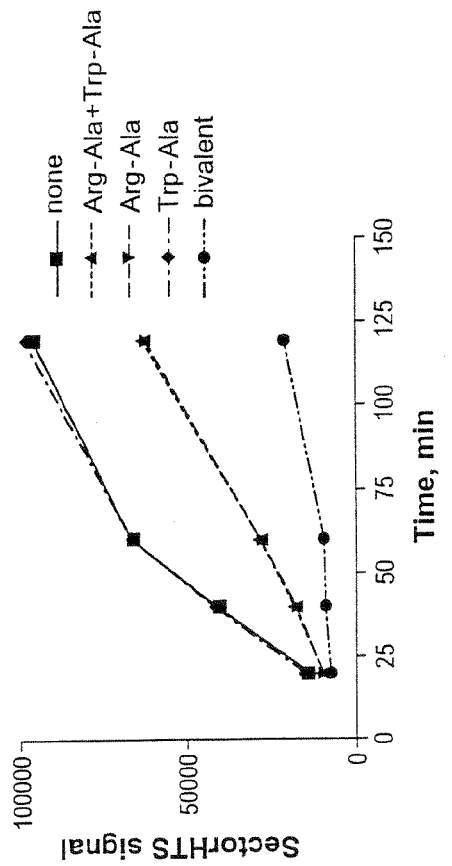
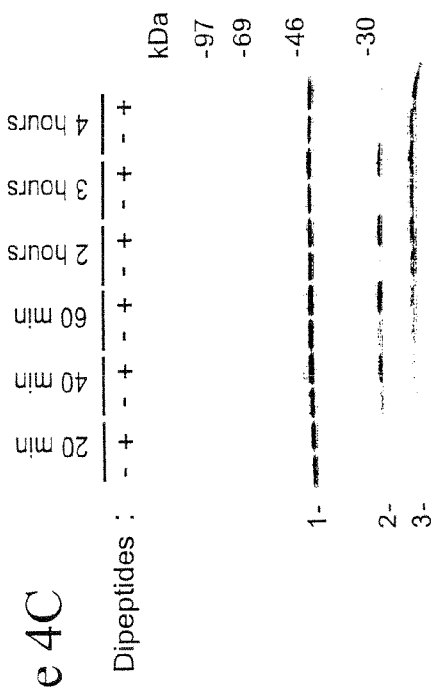
Figure 4A
Figure 4B
Figure 4C

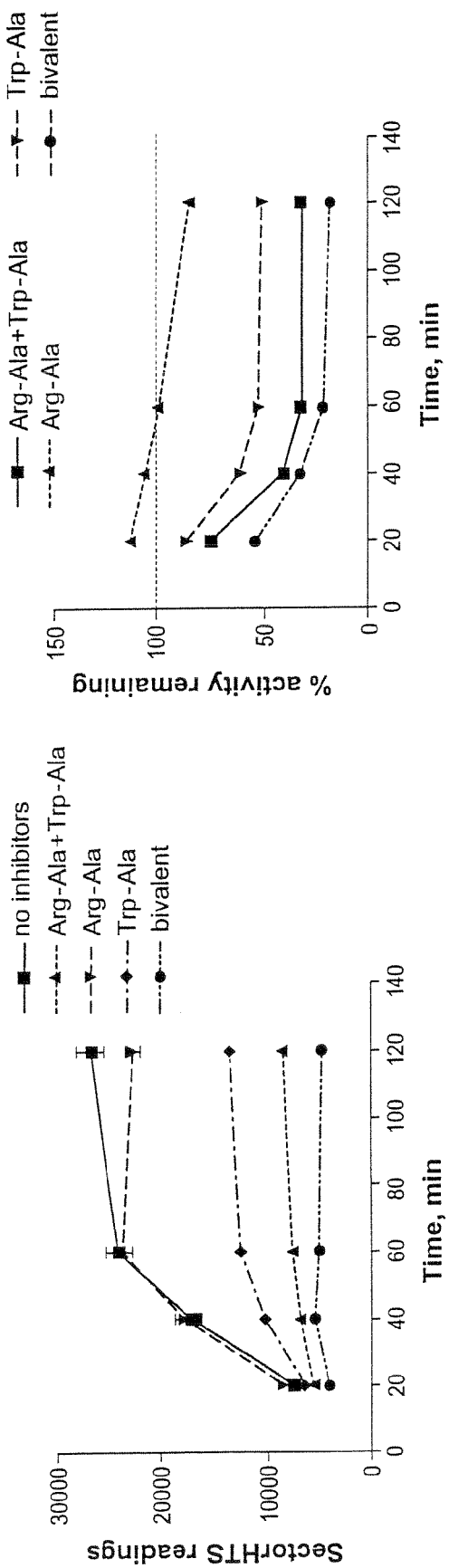
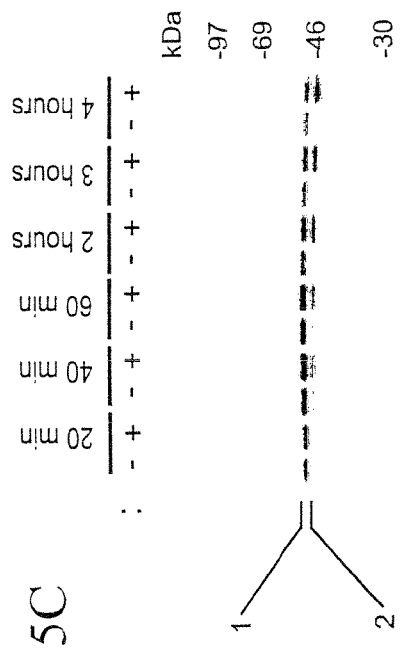
Figure 5A
Figure 5B
Figure 5C

SEQUENCE LISTING

```
<160> NUMBER OF SEQ ID NOS: 24

<210> SEQ ID NO 1
<211> LENGTH: 447
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45
```

```
Gln Thr Pro Thr Glu Asp Gly Ser Glu Pro Gly Ser Glu Thr Ser
     50                  55                  60

Asp Ala Lys Ser Thr Pro Thr Ala Glu Ala Glu Ala Gly Ile Gly
 65                  70                  75                  80

Asp Thr Pro Ser Leu Glu Asp Glu Ala Ala Gly His Val Thr Gln Ala
                 85                  90                  95

Arg Met Val Ser Lys Ser Lys Asp Gly Thr Gly Ser Asp Asp Lys Lys
                100                 105                 110

Ala Lys Thr Ser Thr Arg Ser Ser Ala Lys Thr Leu Lys Asn Arg Pro
        115                 120                 125

Cys Leu Ser Pro Lys His Pro Thr Pro Gly Ser Ser Asp Pro Leu Ile
130                 135                 140

Gln Pro Ser Ser Pro Ala Val Cys Pro Glu Pro Pro Ser Ser Pro Lys
145                 150                 155                 160

Tyr Val Ser Ser Val Thr Pro Arg Thr Gly Ser Ser Gly Ala Lys Glu
                165                 170                 175

Met Lys Leu Lys Gly Ala Asp Gly Lys Thr Lys Ile Ala Thr Pro Arg
            180                 185                 190

Gly Ala Ala Pro Pro Gly Gln Lys Gly Gln Ala Asn Ala Thr Arg Ile
        195                 200                 205

Pro Ala Lys Thr Pro Pro Ala Pro Lys Thr Pro Pro Ser Ser Gly Glu
210                 215                 220

Pro Pro Lys Ser Gly Asp Arg Ser Gly Tyr Ser Ser Pro Gly Ser Pro
225                 230                 235                 240

Gly Thr Pro Gly Ser Arg Ser Arg Thr Pro Ser Leu Pro Thr Pro Pro
                245                 250                 255

Thr Arg Glu Pro Lys Lys Val Ala Val Val Arg Thr Pro Pro Lys Ser
            260                 265                 270

Pro Ser Ser Ala Lys Ser Arg Leu Gln Thr Ala Pro Val Pro Met Pro
        275                 280                 285

Asp Leu Lys Asn Val Lys Ser Lys Ile Gly Ser Thr Glu Asn Leu Lys
290                 295                 300

His Gln Pro Gly Gly Gly Lys Val Gln Ile Val Tyr Lys Pro Val Asp
305                 310                 315                 320

Leu Ser Lys Val Thr Ser Lys Cys Gly Ser Leu Gly Asn Ile His His
                325                 330                 335

Lys Pro Gly Gly Gly Gln Val Glu Val Lys Ser Glu Lys Leu Asp Phe
            340                 345                 350

Lys Asp Arg Val Gln Ser Lys Ile Gly Ser Leu Asp Asn Ile Thr His
        355                 360                 365

Val Pro Gly Gly Gly Asn Lys Lys Ile Glu Thr His Lys Leu Thr Phe
370                 375                 380

Arg Glu Asn Ala Lys Ala Lys Thr Asp His Gly Ala Glu Ile Val Tyr
385                 390                 395                 400

Lys Ser Pro Val Val Ser Gly Asp Thr Ser Pro Arg His Leu Ser Asn
                405                 410                 415

Val Ser Ser Thr Gly Ser Ile Asp Met Val Asp Ser Pro Gln Leu Ala
            420                 425                 430

Thr Leu Ala Asp Glu Val Ser Ala Ser Leu Ala Lys Gln Gly Leu
        435                 440                 445

<210> SEQ ID NO 2
<211> LENGTH: 335
<212> TYPE: PRT
<213> ORGANISM: Homo sapiens
```

<400> SEQUENCE: 2

| | | | | | | | | | | | | | | |
|---|---|---|---|---|---|---|---|---|---|---|---|---|---|---|
|Met|Arg|Val|Cys|Trp|Leu|Val|Arg|Gln|Asp|Ser|Arg|His|Gln|Arg|Ile|
|1| | | |5| | | | |10| | | | |15| |

Lys Leu Pro His Leu Glu Ala Val Ile Gly Arg Ser Pro Glu Thr
              20                  25                  30

Lys Ile Thr Asp Lys Lys Cys Ser Arg Gln Gln Val Gln Leu Lys Ala
              35                  40                  45

Glu Cys Asn Lys Gly Tyr Val Lys Val Gln Gln Met Gly Val Asn Pro
 50                          55                  60

Thr Ser Ile Asp Ser Gly Val Ile Gly Lys Asp Gln Glu Lys Leu Leu
 65                      70                  75                  80

Leu Pro Gly Gln Val Leu His Met Val Asn Gly Leu Tyr Pro Tyr Ile
                  85                  90                  95

Val Glu Phe Glu Glu Val Ala Glu Ser Pro Asn Leu Thr Gln Arg Lys
                 100                 105                 110

Arg Lys Arg Ser Asp Cys Asp Ser Glu Glu Met Glu Ala Glu Ser Gly
             115                 120                 125

Thr Gly Leu Ala Pro Gly Ser Ser Pro Ser Gln Cys Ser Val Ser Pro
130                     135                 140

Lys Lys Asp Lys Asn Gly Ala Thr Lys Lys Glu Ser Leu Gly His Trp
145                 150                 155                 160

Ser Gln Gly Leu Lys Met Ser Met Lys Asp Pro Lys Met Gln Val Tyr
                 165                 170                 175

Lys Asp Asp Gln Val Val Ile Lys Asp Lys Tyr Pro Lys Ala Arg
             180                 185                 190

His His Trp Leu Val Leu Pro Trp Ala Ser Ile Ser Ser Leu Lys Val
             195                 200                 205

Val Thr Ser Glu His Leu Glu Leu Leu Lys His Met His Ala Val Gly
210                 215                 220

Glu Lys Val Ile Ala Glu Phe Ala Gly Ser Ser Lys Leu Arg Phe Arg
225                 230                 235                 240

Leu Gly Tyr His Ala Ile Pro Ser Met Ser His Val His Leu His Val
                 245                 250                 255

Ile Ser Gln Asp Phe Asp Ser Pro Cys Leu Lys Asn Lys Lys His Trp
             260                 265                 270

Asn Ser Phe Asn Thr Glu Tyr Phe Leu Glu Ser Gln Ala Val Ile Lys
             275                 280                 285

Met Val Gln Glu Ala Gly Arg Val Thr Val Lys Asp Gly Thr Cys Glu
290                 295                 300

Leu Leu Lys Leu Pro Leu Arg Cys His Glu Cys Gln Gln Leu Leu Pro
305                 310                 315                 320

Ser Ile Pro Gln Leu Lys Glu His Leu Arg Lys His Trp Gly Gly
                 325                 330                 335

<210> SEQ ID NO 3
<211> LENGTH: 376
<212> TYPE: PRT
<213> ORGANISM: Homo sapiens

<400> SEQUENCE: 3

Met Ser Lys Ser Val Pro Ala Phe Leu Gln Asp Glu Ser Asp Arg
1               5                   10                  15

Glu Thr Asp Thr Ala Ser Glu Ser Ser Tyr Gln Leu Ser Arg His Lys
              20                  25                  30

```
Lys Ser Pro Ser Ser Leu Thr Asn Leu Ser Ser Ser Gly Met Thr
         35                  40                  45
Ser Leu Ser Ser Val Ser Gly Ser Val Met Ser Val Tyr Ser Gly Asp
 50                  55                  60
Phe Gly Asn Leu Glu Val Lys Gly Asn Ile Gln Phe Ala Ile Glu Tyr
 65                  70                  75                  80
Val Glu Ser Leu Lys Glu Leu His Val Phe Val Ala Gln Cys Lys Asp
                 85                  90                  95
Leu Ala Ala Ala Asp Val Lys Lys Gln Arg Ser Asp Pro Tyr Val Lys
                100                 105                 110
Ala Tyr Leu Leu Pro Asp Lys Gly Lys Met Gly Lys Lys Lys Thr Leu
                115                 120                 125
Val Val Lys Lys Thr Leu Asn Pro Val Tyr Asn Glu Ile Leu Arg Tyr
130                 135                 140
Lys Ile Glu Lys Gln Ile Leu Lys Thr Gln Lys Leu Asn Leu Ser Ile
145                 150                 155                 160
Trp His Arg Asp Thr Phe Lys Arg Asn Ser Phe Leu Gly Glu Val Glu
                165                 170                 175
Leu Asp Leu Glu Thr Trp Asp Trp Asp Asn Lys Gln Asn Lys Gln Leu
                180                 185                 190
Arg Trp Tyr Pro Leu Lys Arg Lys Thr Ala Pro Val Ala Leu Glu Ala
                195                 200                 205
Glu Asn Arg Gly Glu Met Lys Leu Ala Leu Gln Tyr Val Pro Glu Pro
                210                 215                 220
Val Pro Gly Lys Lys Leu Pro Thr Thr Gly Glu Val His Ile Trp Val
225                 230                 235                 240
Lys Glu Cys Leu Asp Leu Pro Leu Leu Arg Gly Ser His Leu Asn Ser
                245                 250                 255
Phe Val Lys Cys Thr Ile Leu Pro Asp Thr Ser Arg Lys Ser Arg Gln
                260                 265                 270
Lys Thr Arg Ala Val Gly Lys Thr Thr Asn Pro Ile Phe Asn His Thr
                275                 280                 285
Met Val Tyr Asp Gly Phe Arg Pro Glu Asp Leu Met Glu Ala Cys Val
                290                 295                 300
Glu Leu Thr Val Trp Asp His Tyr Lys Leu Thr Asn Gln Phe Leu Gly
305                 310                 315                 320
Gly Leu Arg Ile Gly Phe Gly Thr Gly Lys Ser Tyr Gly Thr Glu Val
                325                 330                 335
Asp Trp Met Asp Ser Thr Ser Glu Glu Val Ala Leu Trp Glu Lys Met
                340                 345                 350
Val Asn Ser Pro Asn Thr Trp Ile Glu Ala Thr Leu Pro Leu Arg Met
                355                 360                 365
Leu Leu Ile Ala Lys Ile Ser Lys
                370                 375

<210> SEQ ID NO 4
<211> LENGTH: 90
<212> TYPE: PRT
<213> ORGANISM: Homo sapiens

<400> SEQUENCE: 4

Met Pro Lys Arg Lys Ala Glu Gly Asp Ala Lys Gly Asp Lys Ala Lys
 1               5                  10                  15
Val Lys Asp Glu Pro Gln Arg Arg Ser Ala Arg Leu Ser Ala Lys Pro
                 20                  25                  30
```

```
Ala Pro Pro Lys Pro Glu Pro Lys Lys Ala Pro Ala Lys Lys
            35                  40                  45

Gly Glu Lys Val Pro Lys Lys Lys Gly Lys Ala Asp Ala Gly Lys
 50                  55                  60

Glu Gly Asn Asn Pro Ala Glu Asn Gly Asp Ala Lys Thr Asp Gln Ala
 65                  70                  75                  80

Gln Lys Ala Glu Gly Ala Gly Asp Ala Lys
                85                  90

<210> SEQ ID NO 5
<211> LENGTH: 90
<212> TYPE: PRT
<213> ORGANISM: Homo sapiens

<400> SEQUENCE: 5

Met Pro Lys Arg Lys Ala Glu Gly Asp Ala Lys Gly Asp Lys Ala Lys
 1               5                  10                  15

Val Lys Asp Glu Pro Gln Arg Arg Ser Ala Arg Leu Ser Ala Lys Pro
                20                  25                  30

Ala Pro Pro Lys Pro Glu Pro Lys Pro Lys Lys Ala Pro Ala Lys Lys
            35                  40                  45

Gly Glu Lys Val Pro Lys Gly Lys Lys Gly Lys Ala Asp Ala Gly Lys
 50                  55                  60

Glu Gly Asn Asn Pro Ala Glu Asn Gly Asp Ala Lys Thr Asp Gln Ala
 65                  70                  75                  80

Gln Lys Ala Glu Gly Ala Gly Asp Ala Lys
                85                  90

<210> SEQ ID NO 6
<211> LENGTH: 560
<212> TYPE: PRT
<213> ORGANISM: Homo sapiens

<400> SEQUENCE: 6

Met Pro Gln Thr Arg Ser Gln Ala Gln Ala Thr Ile Ser Phe Pro Lys
 1               5                  10                  15

Arg Lys Leu Ser Arg Ala Leu Asn Lys Ala Lys Asn Ser Ser Asp Ala
                20                  25                  30

Lys Leu Glu Pro Thr Asn Val Gln Thr Val Thr Cys Ser Pro Arg Val
            35                  40                  45

Lys Ala Leu Pro Leu Ser Pro Arg Lys Arg Leu Gly Asp Asp Asn Leu
 50                  55                  60

Cys Asn Thr Pro His Leu Pro Pro Cys Ser Pro Pro Lys Gln Gly Lys
 65                  70                  75                  80

Lys Glu Asn Gly Pro Pro His Ser His Thr Leu Lys Gly Arg Arg Leu
                85                  90                  95

Val Phe Asp Asn Gln Leu Thr Ile Lys Ser Pro Ser Lys Arg Glu Leu
                100                 105                 110

Ala Lys Val His Gln Asn Lys Ile Leu Ser Ser Val Arg Lys Ser Gln
            115                 120                 125

Glu Ile Thr Thr Asn Ser Glu Gln Arg Cys Pro Leu Lys Lys Glu Ser
        130                 135                 140

Ala Cys Val Arg Leu Phe Lys Gln Glu Gly Thr Cys Tyr Gln Gln Ala
145                 150                 155                 160

Lys Leu Val Leu Asn Thr Ala Val Pro Asp Arg Leu Pro Ala Arg Glu
                165                 170                 175
```

-continued

```
Arg Glu Met Asp Val Ile Arg Asn Phe Leu Arg His Ile Cys Gly
            180                 185                 190
Lys Lys Ala Gly Ser Leu Tyr Leu Ser Gly Ala Pro Gly Thr Gly Lys
        195                 200                 205
Thr Ala Cys Leu Ser Arg Ile Leu Gln Asp Leu Lys Lys Glu Leu Lys
210                 215                 220
Gly Phe Lys Thr Ile Met Leu Asn Cys Met Ser Leu Arg Thr Ala Gln
225                 230                 235                 240
Ala Val Phe Pro Ala Ile Ala Gln Glu Ile Cys Gln Glu Glu Val Ser
                245                 250                 255
Arg Pro Ala Gly Lys Asp Met Met Arg Lys Leu Glu Lys His Met Thr
            260                 265                 270
Ala Glu Lys Gly Pro Met Ile Val Leu Val Leu Asp Glu Met Asp Gln
        275                 280                 285
Leu Asp Ser Lys Gly Gln Asp Val Leu Tyr Thr Leu Phe Glu Trp Pro
290                 295                 300
Trp Leu Ser Asn Ser His Leu Val Leu Ile Gly Ile Ala Asn Thr Leu
305                 310                 315                 320
Asp Leu Thr Asp Arg Ile Leu Pro Arg Leu Gln Ala Arg Glu Lys Cys
                325                 330                 335
Lys Pro Gln Leu Leu Asn Phe Pro Pro Tyr Thr Arg Asn Gln Ile Val
            340                 345                 350
Thr Ile Leu Gln Asp Arg Leu Asn Gln Val Ser Arg Asp Gln Val Leu
        355                 360                 365
Asp Asn Ala Ala Val Gln Phe Cys Ala Arg Lys Val Ser Ala Val Ser
370                 375                 380
Gly Asp Val Arg Lys Ala Leu Asp Val Cys Arg Arg Ala Ile Glu Ile
385                 390                 395                 400
Val Glu Ser Asp Val Lys Ser Gln Thr Ile Leu Lys Pro Leu Ser Glu
                405                 410                 415
Cys Lys Ser Pro Ser Glu Pro Leu Ile Pro Lys Arg Val Gly Leu Ile
            420                 425                 430
His Ile Ser Gln Val Ile Ser Glu Val Asp Gly Asn Arg Met Thr Leu
        435                 440                 445
Ser Gln Glu Gly Ala Gln Asp Ser Phe Pro Leu Gln Gln Lys Ile Leu
450                 455                 460
Val Cys Ser Leu Met Leu Leu Ile Arg Gln Leu Lys Ile Lys Glu Val
465                 470                 475                 480
Thr Leu Gly Lys Leu Tyr Glu Ala Tyr Ser Lys Val Cys Arg Lys Gln
                485                 490                 495
Gln Val Ala Ala Val Asp Gln Ser Glu Cys Leu Ser Leu Ser Gly Leu
            500                 505                 510
Leu Glu Ala Arg Gly Ile Leu Gly Leu Lys Arg Asn Lys Glu Thr Arg
        515                 520                 525
Leu Thr Lys Val Phe Phe Lys Ile Glu Glu Lys Glu Ile Glu His Ala
530                 535                 540
Leu Lys Asp Lys Ala Leu Ile Gly Asn Ile Leu Ala Thr Gly Leu Pro
545                 550                 555                 560
```

<210> SEQ ID NO 7
<211> LENGTH: 560
<212> TYPE: PRT
<213> ORGANISM: Homo sapiens

```
<400> SEQUENCE: 7

Met Pro Gln Thr Arg Ser Gln Ala Gln Ala Thr Ile Ser Phe Pro Lys
1               5                   10                  15

Arg Lys Leu Ser Arg Ala Leu Asn Lys Ala Lys Asn Ser Ser Asp Ala
            20                  25                  30

Lys Leu Glu Pro Thr Asn Val Gln Thr Val Thr Cys Ser Pro Arg Val
        35                  40                  45

Lys Ala Leu Pro Leu Ser Pro Arg Lys Arg Leu Gly Asp Asp Asn Leu
    50                  55                  60

Cys Asn Thr Pro His Leu Pro Pro Cys Ser Pro Pro Lys Gln Gly Lys
65                  70                  75                  80

Lys Glu Asn Gly Pro Pro His Ser His Thr Leu Lys Gly Arg Arg Leu
                85                  90                  95

Val Phe Asp Asn Gln Leu Thr Ile Lys Ser Pro Ser Lys Arg Glu Leu
            100                 105                 110

Ala Lys Val His Gln Asn Lys Ile Leu Ser Ser Val Arg Lys Ser Gln
        115                 120                 125

Glu Ile Thr Thr Asn Ser Glu Gln Arg Cys Pro Leu Lys Lys Glu Ser
    130                 135                 140

Ala Cys Val Arg Leu Phe Lys Gln Glu Gly Thr Cys Tyr Gln Gln Ala
145                 150                 155                 160

Lys Leu Val Leu Asn Thr Ala Val Pro Asp Arg Leu Pro Ala Arg Glu
                165                 170                 175

Arg Glu Met Asp Val Ile Arg Asn Phe Leu Arg Glu His Ile Cys Gly
            180                 185                 190

Lys Lys Ala Gly Ser Leu Tyr Leu Ser Gly Ala Pro Gly Thr Gly Lys
        195                 200                 205

Thr Ala Cys Leu Ser Arg Ile Leu Gln Asp Leu Lys Lys Glu Leu Lys
    210                 215                 220

Gly Phe Lys Thr Ile Met Leu Asn Cys Met Ser Leu Arg Thr Ala Gln
225                 230                 235                 240

Ala Val Phe Pro Ala Ile Ala Gln Glu Ile Cys Gln Glu Val Ser
                245                 250                 255

Arg Pro Ala Gly Lys Asp Met Met Arg Lys Leu Glu Lys His Met Thr
            260                 265                 270

Ala Glu Lys Gly Pro Met Ile Val Leu Val Leu Asp Glu Met Asp Gln
        275                 280                 285

Leu Asp Ser Lys Gly Gln Asp Val Leu Tyr Thr Leu Phe Glu Trp Pro
    290                 295                 300

Trp Leu Ser Asn Ser His Leu Val Leu Ile Gly Ile Ala Asn Thr Leu
305                 310                 315                 320

Asp Leu Thr Asp Arg Ile Leu Pro Arg Leu Gln Ala Arg Glu Lys Cys
                325                 330                 335

Lys Pro Gln Leu Leu Asn Phe Pro Pro Tyr Thr Arg Asn Gln Ile Val
            340                 345                 350

Thr Ile Leu Gln Asp Arg Leu Asn Gln Val Ser Arg Asp Gln Val Leu
        355                 360                 365

Asp Asn Ala Ala Val Gln Phe Cys Ala Arg Lys Val Ser Ala Val Ser
    370                 375                 380

Gly Asp Val Arg Lys Ala Leu Asp Val Cys Arg Arg Ala Ile Glu Ile
385                 390                 395                 400

Val Glu Ser Asp Val Lys Ser Gln Thr Ile Leu Lys Pro Leu Ser Glu
                405                 410                 415
```

```
Cys Lys Ser Pro Ser Glu Pro Leu Ile Pro Lys Arg Val Gly Leu Ile
            420                 425                 430

His Ile Ser Gln Val Ile Ser Glu Val Asp Gly Asn Arg Met Thr Leu
            435                 440                 445

Ser Gln Glu Gly Ala Gln Asp Ser Phe Pro Leu Gln Gln Lys Ile Leu
            450                 455                 460

Val Cys Ser Leu Met Leu Leu Ile Arg Gln Leu Lys Ile Lys Glu Val
465                 470                 475                 480

Thr Leu Gly Lys Leu Tyr Glu Ala Tyr Ser Lys Val Cys Arg Lys Gln
                485                 490                 495

Gln Val Ala Ala Val Asp Gln Ser Glu Cys Leu Ser Leu Ser Gly Leu
            500                 505                 510

Leu Glu Ala Arg Gly Ile Leu Gly Leu Lys Arg Asn Lys Glu Thr Arg
            515                 520                 525

Leu Thr Lys Val Phe Phe Lys Ile Glu Glu Lys Glu Ile Glu His Ala
            530                 535                 540

Leu Lys Asp Lys Ala Leu Ile Gly Asn Ile Leu Ala Thr Gly Leu Pro
545                 550                 555                 560

<210> SEQ ID NO 8
<211> LENGTH: 77
<212> TYPE: PRT
<213> ORGANISM: Homo sapiens

<400> SEQUENCE: 8

Met Pro Lys Arg Lys Ser Pro Glu Asn Thr Glu Gly Lys Asp Gly Ser
1               5                   10                  15

Lys Val Thr Lys Gln Glu Pro Thr Arg Arg Ser Ala Arg Leu Ser Ala
            20                  25                  30

Lys Pro Ala Pro Pro Lys Pro Glu Pro Lys Pro Arg Lys Thr Ser Ala
        35                  40                  45

Lys Lys Glu Pro Gly Ala Lys Ile Ser Arg Gly Ala Lys Gly Lys Lys
    50                  55                  60

Glu Glu Lys Gln Glu Ala Gly Lys Glu Gly Thr Glu Asn
65                  70                  75

<210> SEQ ID NO 9
<211> LENGTH: 95
<212> TYPE: PRT
<213> ORGANISM: Homo sapiens

<400> SEQUENCE: 9

Met Pro Lys Arg Lys Ser Pro Glu Asn Thr Glu Gly Lys Asp Gly Ser
1               5                   10                  15

Lys Val Thr Lys Gln Glu Pro Thr Arg Arg Ser Ala Arg Leu Ser Ala
            20                  25                  30

Lys Pro Ala Pro Pro Lys Pro Glu Pro Lys Pro Arg Lys Thr Ser Ala
        35                  40                  45

Lys Lys Glu Pro Gly Ala Lys Ile Ser Arg Gly Ala Lys Gly Lys Lys
    50                  55                  60

Glu Glu Lys Gln Glu Ala Gly Lys Glu Gly Thr Ala Pro Ser Glu Asn
65                  70                  75                  80

Gly Glu Thr Lys Ala Glu Glu Val Leu Ser Ile Asn Thr Ser His
                85                  90                  95
```

```
<210> SEQ ID NO 10
<211> LENGTH: 560
<212> TYPE: PRT
<213> ORGANISM: Homo sapiens

<400> SEQUENCE: 10

Met Gly Lys Gly Phe Gln Asn Phe Met Ser Lys Asp Phe His Pro
1               5                   10                  15

Ser Ala Phe Arg Asn Leu Lys Met Val Trp Glu Ala Arg Gln Lys Lys
                20                  25                  30

Ser Leu Glu Asp Lys Arg Gln Glu Glu Leu Arg Val Ala Tyr Glu Lys
            35                  40                  45

Glu Gln Glu Ile Leu Asn Asn Lys Ala Leu Leu Gly Asp Glu Lys Ala
        50                  55                  60

Lys Met Gly Leu Ser Phe Met Tyr Asp Ala Pro Ala Gly Met Thr Lys
65                  70                  75                  80

Arg Glu Glu Pro Lys Glu Glu Pro Lys Phe Glu Trp Gln Arg Lys Tyr
                85                  90                  95

Gln Ala Pro Arg Glu Asp Trp Ala Lys Gly Asn Glu Glu Ile Gln Asp
            100                 105                 110

Gln Pro Phe Gly Ile Gln Val Arg Asn Val Arg Cys Cys Lys Cys His
        115                 120                 125

Lys Trp Gly His Ile Asn Thr Asp Arg Glu Cys Pro Leu Phe Gly Lys
130                 135                 140

Ser Gly Asn Phe Glu Asp Glu Gly Tyr Ala Asn Asn Pro Ser Asp Leu
145                 150                 155                 160

Ile Lys Asp Leu Arg Arg Arg Gln Glu Gly Lys Ala Gly Pro Ser
                165                 170                 175

Thr Ser Lys Ser Ser Ala Ala Ala Thr Gly Glu Asp Asp Asp Glu
            180                 185                 190

Asp Glu Trp Met Asp His Gln Gln Leu Ala Ser Asp Met Arg Glu Glu
                195                 200                 205

His Gly Ile Lys Leu Lys Ser Val Leu Ala Gly Met Gln Thr Asp
        210                 215                 220

Gln Gln Leu Thr Arg Met Lys Lys Glu Met Thr Glu Glu Met Met
225                 230                 235                 240

Leu Glu Phe Phe Asn Ser Met Thr Glu Lys Glu Lys Lys Leu His
                245                 250                 255

Lys Lys Leu Met Ser Gly Ala Asp Leu Glu Asp Val Met Lys Lys
                260                 265                 270

Ser Lys Lys Glu Lys Lys Glu Lys Lys Glu Lys Arg Lys Asn Lys
            275                 280                 285

Asp Lys Lys Asp Lys Lys Asn Lys Lys Ser Lys Arg Glu
            290                 295                 300

Thr Asp Asp Asp Ser Asp Gly Ser Asp Ser Glu Asp Trp Lys Glu
305                 310                 315                 320

Lys Ser Ser Lys Arg Ile Lys Arg Glu Val Glu Ser Ser Pro Glu Tyr
                325                 330                 335

Arg Ser Lys Tyr Ile Lys Gln Glu Val Leu Ser Glu Glu Asn Ser
            340                 345                 350

His Gly Arg Lys Asp Ser Ser Arg Lys Arg Ala His Asn Asp Ser Glu
                355                 360                 365

Ser Ser Asn Glu Val Arg Ser Ser Glu Arg Lys Arg Ser Arg Arg Asp
            370                 375                 380
```

-continued

```
Asp Ser Pro Asn Ala Lys Arg Ser Ile Gly Leu Lys Ser Pro Glu Arg
385                 390                 395                 400

Arg Ser Ser Arg Asp Arg Lys Ser Ser Pro Lys Gln Arg Gln Asp Ser
            405                 410                 415

Pro Val Arg Arg Arg Arg Ser Pro Ser Ser Ile Arg Lys Glu Ser Gln
        420                 425                 430

Arg Val Arg Lys His Ser Pro Glu Gln Lys Arg Asn Gly Arg His Asp
        435                 440                 445

Ser Arg Ser Val Ser Pro Val Arg Arg Arg Ser Pro Ser Pro Asp
    450                 455                 460

Asn Arg Gln Leu Gly Ser Arg Lys Gln Tyr Ser Pro Leu Arg Arg Arg
465                 470                 475                 480

Gln Ser Ser Pro Met Val Ala Ser Pro Arg Arg Arg Ser Pro Ser
            485                 490                 495

Pro Glu Arg Gln Arg Lys Arg Ser Pro Ser Asp Ser Pro Thr
        500                 505                 510

Arg Arg Leu Ser Thr Ser Pro Ile Arg Arg Arg Ser Pro Ser Pro
        515                 520                 525

Asn Lys Leu Pro Val Arg Arg Arg His Asp Ser Gly Ser Pro Asp
530                 535                 540

Arg Asp Gly Ser Glu Ser Pro Lys Met Trp Arg Lys Ser His Lys
545                 550                 555                 560

<210> SEQ ID NO 11
<211> LENGTH: 225
<212> TYPE: PRT
<213> ORGANISM: Homo sapiens

<400> SEQUENCE: 11

Met Ser Arg Pro Arg Lys Arg Leu Ala Gly Thr Ser Gly Ser Asp Lys
1               5                   10                  15

Gly Leu Ser Gly Lys Arg Thr Lys Thr Glu Asn Ser Gly Glu Ala Leu
            20                  25                  30

Ala Lys Val Glu Asp Ser Asn Pro Gln Lys Thr Ser Ala Thr Lys Asn
        35                  40                  45

Cys Leu Lys Asn Leu Ser Ser His Trp Leu Met Lys Ser Glu Pro Glu
    50                  55                  60

Ser Arg Leu Glu Lys Gly Val Asp Val Lys Phe Ser Ile Glu Asp Leu
65                  70                  75                  80

Lys Ala Gln Pro Lys Gln Thr Thr Cys Trp Asp Gly Val Arg Asn Tyr
                85                  90                  95

Gln Ala Arg Asn Phe Leu Arg Ala Met Lys Leu Gly Glu Glu Ala Phe
            100                 105                 110

Phe Tyr His Ser Asn Cys Lys Glu Pro Gly Ile Ala Gly Leu Met Lys
        115                 120                 125

Ile Val Lys Glu Ala Tyr Pro Asp His Thr Gln Phe Glu Lys Asn Asn
    130                 135                 140

Pro His Tyr Asp Pro Ser Ser Lys Glu Asp Asn Pro Lys Trp Ser Met
145                 150                 155                 160

Val Asp Val Gln Phe Val Arg Met Met Lys Arg Phe Ile Pro Leu Ala
                165                 170                 175

Glu Leu Lys Ser Tyr His Gln Ala His Lys Ala Thr Gly Gly Pro Leu
            180                 185                 190

Lys Asn Met Val Leu Phe Thr Arg Gln Arg Leu Ser Ile Gln Pro Leu
        195                 200                 205
```

```
Thr Gln Glu Glu Phe Asp Phe Val Leu Ser Leu Glu Glu Lys Glu Pro
    210                 215                 220
Ser
225

<210> SEQ ID NO 12
<211> LENGTH: 328
<212> TYPE: PRT
<213> ORGANISM: Homo sapiens

<400> SEQUENCE: 12

Met Ser Met Leu Ala Glu Arg Arg Lys Gln Lys Trp Ala Val Asp
1               5                   10                  15

Pro Gln Asn Thr Ala Trp Ser Asn Asp Asp Ser Lys Phe Gly Gln Arg
                20                  25                  30

Met Leu Glu Lys Met Gly Trp Ser Lys Gly Lys Gly Leu Gly Ala Gln
            35                  40                  45

Glu Gln Gly Ala Thr Asp His Ile Lys Val Gln Val Lys Asn Asn His
        50                  55                  60

Leu Gly Leu Gly Ala Thr Ile Asn Asn Glu Asp Asn Trp Ile Ala His
65                  70                  75                  80

Gln Asp Asp Phe Asn Gln Leu Leu Ala Glu Leu Asn Thr Cys His Gly
                85                  90                  95

Gln Glu Thr Thr Asp Ser Ser Asp Lys Lys Glu Lys Lys Ser Phe Ser
                100                 105                 110

Leu Glu Glu Lys Ser Lys Ile Ser Lys Asn Arg Val His Tyr Met Lys
            115                 120                 125

Phe Thr Lys Gly Lys Asp Leu Ser Ser Arg Ser Lys Thr Asp Leu Asp
        130                 135                 140

Cys Ile Phe Gly Lys Arg Gln Ser Lys Lys Thr Pro Glu Gly Asp Ala
145                 150                 155                 160

Ser Pro Ser Thr Pro Glu Glu Asn Glu Thr Thr Thr Ser Ala Phe
                165                 170                 175

Thr Ile Gln Glu Tyr Phe Ala Lys Arg Met Ala Ala Leu Lys Asn Lys
            180                 185                 190

Pro Gln Val Pro Val Pro Gly Ser Asp Ile Ser Val Thr Gln Val Glu
        195                 200                 205

Arg Lys Arg Gly Lys Lys Arg Asn Lys Glu Ala Thr Gly Lys Asp Val
    210                 215                 220

Glu Ser Tyr Leu Gln Pro Lys Ala Lys Arg His Thr Glu Gly Lys Pro
225                 230                 235                 240

Glu Arg Ala Glu Ala Gln Glu Arg Val Ala Lys Lys Ser Ala Pro
                245                 250                 255

Ala Glu Glu Gln Leu Arg Gly Pro Cys Trp Asp Gln Ser Ser Lys Ala
            260                 265                 270

Ser Ala Gln Asp Ala Gly Asp His Val Gln Pro Pro Glu Gly Arg Asp
        275                 280                 285

Phe Thr Leu Lys Pro Lys Arg Arg Gly Lys Lys Leu Gln Lys
    290                 295                 300

Pro Val Glu Ile Ala Glu Asp Ala Thr Leu Glu Glu Thr Leu Val Lys
305                 310                 315                 320

Lys Lys Lys Lys Lys Asp Ser Lys
                325
```

```
<210> SEQ ID NO 13
<211> LENGTH: 1765
<212> TYPE: DNA
<213> ORGANISM: Homo sapiens

<400> SEQUENCE: 13
gtcgacccac gcgtccgggc accaacagca gcgccgctgc caccgcccac cttctgccgc      60
cgccaccaca gccaccttct cctcctccgc tgtcctctcc gtcctcgcct ctgtcgacta     120
tcaggtgagc tttgaaccag gatggctgag ccccgccagg agttcgaagt gatggaagat     180
cacgctggga cgtacgggtt ggggacagg aaagatcagg ggctacac catgcaccaa        240
gaccaagagg gtgacacgga cgctggcctg aaagaatctc ccctgcagac ccccactgag     300
gacggatctg aggaaccggg ctctgaaacc tctgatgcta agagcactcc aacagcggaa     360
gctgaagaag caggcattgg agacaccccc agcctggaag acgaagctgc tggtcacgtg     420
acccaagctc gcatggtcag taaaagcaaa gacgggactg gaagcgatga caaaaaagcc     480
aagacatcca cacgttcctc tgctaaaacc ttgaaaaata ggccttgcct agccccaaa      540
cacccactc ctggtagctc agaccctctg atccaaccct ccagccctgc tgtgtgccca      600
gagccacctt cctctcctaa atacgtctct tctgtcactc cccgaactgg cagttctgga     660
gcaaaggaga tgaaactcaa gggggctgat ggtaaaacga agatcgccac accgcgggga     720
gcagcccctc caggccagaa gggccaggcc aacgccacca ggattccagc aaaaacccca     780
cccgctccaa agacaccacc cagctctggt gaacctccaa aatcagggga tcgcagcggc     840
tacagcagcc ccggctcccc aggcactccc ggcagccgct cccgcaccccc gtcccttcca   900
accccaccca cccgggagcc aagaaggtg gcggtggtcc gtactccacc caagtcgccg      960
tcttccgcca agagccgcct gcagacagcc ccgtgccca tgccagacct gaagaacgtc     1020
aagtccaaga tcggctccac tgagaacctg aagcaccagc cgggaggcgg aaggtgcaa     1080
atagtctaca accagttga cctgagcaag gtgacctcca agtgtggctc attaggcaac     1140
atccatcata accaggagg tggccaggtg gaagtaaaat ctgagaagct tgacttcaag     1200
gacagagtcc agtcgaagat tgggtccctg gacaatatca cccacgtccc tggcggagga     1260
aataaaaaga ttgaaaccca aagctgacc ttccgcgaga cgccaaagc caagacagac      1320
cacggggcgg agatcgtgta caagtcgcca gtggtgtctg gggacacgtc tccacggcat    1380
ctcagcaatg tctcctccac cggcagcatc gacatggtag actcgcccca gctcgccacg    1440
ctagctgacg aggtgtctgc ctccctggcc aagcagggtt tgtgatcagg cccctggggc    1500
ggtcaataat cgtggagagg agagaatgag agagtgtgga aaaaaaaag aataatgacc     1560
cggcccccgc cctctgcccc cagctgctcc tcgcagttcg gttaattggt taatcactta    1620
acctgctttt gtcactcggc tttggctcgg acttcaaaa tcagtgatgg gagtaagagc     1680
aaatttcatc tttccaaatt gatgggtggg ctagtaataa aatattttaa aaaaaccaa     1740
aaaaaaaaaa aaaagggcg gccgc                                           1765

<210> SEQ ID NO 14
<211> LENGTH: 1407
<212> TYPE: DNA
<213> ORGANISM: Homo sapiens

<400> SEQUENCE: 14
gcggcgaggc gcagtagagc agcgtgaagt ttgtgggtgt ccacagtcga gagctaagat      60
gcgagtgtgc tggttggtga cacaggacag caggcaccag cgaatcaaac ttccccattt     120
ggaagctgtt gtgattggtc gaagcccaga gaccaagatc acagataaga aatgttcccg     180
```

-continued

| | |
|---|---|
| acagcaagta cagttgaaag cagagtgtaa caagggatat gtcaaagtac agcagatggg | 240 |
| ggtcaacccc accagcattg actcgggcgt catcgggaag gaccaagaga agctgctgct | 300 |
| gcctggtcag gttctccaca tggtgaatgg actttatcca tacatcgtag agtttgagga | 360 |
| agtggcagag agccctaacc taacacagag gaagagaaaa aggtcagact gtgatagtga | 420 |
| ggagatggaa gctgagtctg ggacagggct ggcacctggg agcagcccca gccagtgctc | 480 |
| tgtgtcccct aagaaggaca agaatggagc caccaaaaag gaatcactgg gccactggag | 540 |
| tcaaggcttg aagatgtcta tgaaagaccc caaaatgcag gtttacaaag acgaccaggt | 600 |
| ggtggtgatt aaggataaat accccaaggc ccgtcaccac tggctggtct taccgtgggc | 660 |
| ctccatttcc agtctgaagg ttgtgaccag tgaacacctt gaacttctca acatatgca | 720 |
| cgctgtgggg gagaaggtga tagcagagtt tgctggatcc agcaaactgc gcttccgatt | 780 |
| gggctaccat gccattccca gcatgagcca cgtacatctt catgtgatca gccaggattt | 840 |
| tgattctcct tgccttaaaa acaaaaagca ttggaattct tttaatacag aatactttct | 900 |
| ggaatcacaa gctgtgatca agatggttca ggaagccggc agagtgactg ttaaagatgg | 960 |
| cacttgtgag ctcttgaagc tgcctctccg ttgccatgag tgtcagcagc tgctgccttc | 1020 |
| catcccgcag ctgaaagagc acctcaggaa gcactggggc gggtgacact cgtctcggcg | 1080 |
| accaagggca gtgctagcat ctatccgcat tgcctatgct ccattcaatc ctgaactaaa | 1140 |
| gcgtacactt cttcgaaaca aagcttattt attcttgagc ggccacacat tggttgcact | 1200 |
| ctggtgtaag aactgggaat ttgggttttg tgggtgtatt ctctggtaat ggaggctgag | 1260 |
| acatgcctgg tcacccttcc caggaccatg acaggcctga ctaatgagag ggcagagccg | 1320 |
| gcttgagact caaatgcacg atgtagaagc agaggattgg taatatattt tgtttctacc | 1380 |
| ctcaaaaaaa aaaaaaaaaa aaaaaaa | 1407 |

<210> SEQ ID NO 15
<211> LENGTH: 1646
<212> TYPE: DNA
<213> ORGANISM: Homo sapiens

<400> SEQUENCE: 15

| | |
|---|---|
| cggacgcgtg ggccctgaca aactcaaaag gatgagcaag tctgttccag catttctcca | 60 |
| agatgagagt gatgacagag aaacagatac agcatcagaa agcagttacc agctcagcag | 120 |
| acacaagaag agcccgagct cttaaccaa tcttagcagc tcctctggca tgacgtcctt | 180 |
| gtcttctgtg agtggcagtg tgatgagtgt ttatagtgga gactttggca atctggaagt | 240 |
| taaaggaaat attcagtttg caattgaata tgtggagtca ctgaaggagt tgcatgtttt | 300 |
| tgtggcccag tgtaaggact tagcagcagc ggatgtaaaa aaacagcgtt cagacccata | 360 |
| tgtaaaggcc tatttgctac cagacaaagg caaaatgggc aagaagaaaa cactcgtagt | 420 |
| gaagaaaacc ttgaatcctg tgtataacga aatactgcgg tataaaattg aaaaacaaat | 480 |
| cttaaagaca cagaaattga acctgtccat ttggcatcgg gatacattta gcgcaatag | 540 |
| tttcctaggg gaggtggaac ttgatttgga aacatgggac tgggataaca acagaataa | 600 |
| acaattgaga tggtaccctc tgaagcggaa gacagcacca gttgcccttg aagcagaaaa | 660 |
| cagaggtgaa atgaaactag ctctccagta tgtcccagag ccagtccctg gtaaaaagct | 720 |
| tcctacaact ggagaagtgc acatctgggt gaaggaatgc cttgatctac cactgctaag | 780 |
| gggaagtcat ctaaattctt ttgttaaatg taccatcctt ccagatacaa gtaggaaaag | 840 |
| tcgccagaag acaagagctg tagggaaaac caccaaccct atcttcaacc acactatggt | 900 |

```
gtatgatggg ttcaggcctg aagatctgat ggaagcctgt gtagagctta ctgtctggga    960
ccattacaaa ttaaccaacc aattttgg  aggtcttcgt attggctttg aacaggtaa     1020 aagttatggg actgaagtgg actggatgga ctctacttca gaggaagttg ctctctggga   1080
gaagatggta aactccccca atacttggat tgaagcaaca ctgcctctca gaatgctttt   1140
gattgccaag atttccaaat gagcccaaat tccactggct cctccactga aaactactaa   1200
accggtggaa tctgatcttg aaaatctgag taggtggaca aatatcctca ctttctatct   1260
attgcaccta aggaatacta cacagcatgt aaaagtcaat ctgcatgtgc ttctttgatt   1320
acaaggccca aggatttaa  atataacaaa atgtgtaatt tgtgactcta atattaaata   1380
agatatttga acaagctagg aaaattgaat ttctgctgct gcttcaaaga aaaagctgcc   1440
ccagagcatt aaacatgggg tattgttaag aagcaaaatg ttcttgtttg ccatcatgtg   1500
tttcacacca caattctgtg ccacagttaa gagggtctgg tacccttgca ggacctttgt   1560
aggttgtggg aaaagtcgc  agaaagatac tcaaagtgga gcagggaatg agacagaca    1620 tcagtgatga taaaaaaaaa aaaaaa                                        1646

<210> SEQ ID NO 16
<211> LENGTH: 1198
<212> TYPE: DNA
<213> ORGANISM: Homo sapiens

<400> SEQUENCE: 16
gagcagtgtg aagaagaggc gagaacgacc cccggaccga ccaaagcccg cgcgccgctg     60
catcccgcgt ccagcaccta cgtcccgctg ccgtcgccgc cgccaccatg cccaagagaa    120
aggctgaagg ggatgctaag ggagataaag caaggtgaa  ggacgaacca cagagaagat    180
ccgcgaggtt gtctgctaaa cctgctcctc caaagccaga gcccaagcct aaaaaggccc    240
ctgcaaagaa gggagagaag gtacccaaag ggaaaagggg aaaagctgat gctggcaagg    300
aggggaataa ccctgcagaa aatggagatg ccaaaacaga ccaggcacag aaagctgaag    360
gtgctggaga tgccaagtga agtgtgtgca ttttgataa  ctgtgtactt ctggtgactg    420
tacagtttga aatactattt tttatcaagt tttataaaa  tgcagaattt tgttttactt    480
tttttttttt tttaaaagct atgttgttag cacacagaac acttcattgt tgtttttggg    540 ggaagggca  tatgtcacta atagaatgtc tccaaagctg gattgatgtg agaaaaacac    600
ctttcccttc tagttttgag agacttcctc ttggctccca ggaggaggga ttccctgact    660
ttgacacaca tggccacctt ggcacaaaag ccttgtggta tagaaaaaca aatttgtttt    720
tatgtcctct tctcccttc  catctttcag catagactta actcccttaa gcccagacat    780
ctgttgagac ctgaccccta gtcattggtt accagtgtgt caggcaatct ggactttcca    840
gtgatgccac tgagatggca cctgtcaaaa gagcagtggt tccatttcta gattgtggat    900
cttcagataa attctgccat tttcatttca cttcctgaaa gtcagggtcg cttgtgaaa    960 agttgttaaa caacatgcta aatgtgaaat gtcaaccctc actctaaact ttccctgttc   1020
agagcatcag atgaagactt cattgggttt tatagtggct ttctgatttt tggtagtcca   1080
ttgaagaagg gagtttgaaa gttgttgtat actgttaacg attgtctgcc catgtcctgc   1140
ctgaaatacc atgattgttt atggaaagta tctttaataa agctggatac agtttggc    1198

<210> SEQ ID NO 17
<211> LENGTH: 1198
<212> TYPE: DNA
<213> ORGANISM: Homo sapiens
```

<400> SEQUENCE: 17

```
gagcagtgtg aagaagaggc gagaacgacc cccggaccga ccaaagcccg cgcgccgctg      60
catcccgcgt ccagcaccta cgtcccgctg ccgtcgccgc cgccaccatg cccaagagaa     120
aggctgaagg ggatgctaag ggagataaag caaaggtgaa ggacgaacca cagagaagat     180
ccgcgaggtt gtctgctaaa cctgctcctc caaagccaga gcccaagcct aaaaaggccc     240
ctgcaaagaa gggagagaag gtacccaaag ggaaaaaggg aaaagctgat gctggcaagg     300
aggggaataa ccctgcagaa aatggagatg ccaaaacaga ccaggcacag aaagctgaag     360
gtgctggaga tgccaagtga agtgtgtgca ttttgataa ctgtgtactt ctggtgactg      420
tacagtttga atactatt tttatcaagt tttataaaaa tgcagaattt tgttttactt      480
tttttttttt tttaaaagct atgttgttag cacacagaac acttcattgt tgtttttggg     540
ggaaggggca tatgtcacta atagaatgtc tccaaagctg gattgatgtg gagaaaacac     600
cttccccttc tagttttgag agacttcctc ttggctccca ggaggaggga ttccctgact     660
tgacacaca tggccacctt ggcacaaaag ccttgtggta tagaaaaaca aatttgtttt      720
tatgtcctct tctcccttc catcttcag catagactta actcccttaa gcccagacat       780
ctgttgagac ctgaccccta gtcattggtt accagtgtgt caggcaatct ggactttcca     840
gtgatgccac tgagatggca cctgtcaaaa gagcagtggt tccatttcta gattgtggat     900
cttcagataa attctgccat tttcatttca cttcctgaaa gtcagggtcg gcttgtgaaa     960
agttgttaaa caacatgcta aatgtgaaat gtcaaccctc actctaaact ttccctgttc    1020
agagcatcag atgaagactt cattgggttt tatagtggct ttctgatttt tggtagtcca    1080
ttgaagaagg gagtttgaaa gttgttgtat actgttaacg attgtctgcc catgtcctgc    1140
ctgaaatacc atgattgttt atggaaagta tctttaataa agctggatac agtttggc     1198
```

<210> SEQ ID NO 18
<211> LENGTH: 2653
<212> TYPE: DNA
<213> ORGANISM: Homo sapiens

<400> SEQUENCE: 18

```
gagcgcggct ggagtttgct gctgccgctg tgcagtttgt tcaggggctt gtggtggtga      60
gtccgagagg ctgcgtgtga gagacgtgag aaggatcctg cactgaggag gtggaaagaa     120
gaggattgct cgaggaggcc tggggtctgt gaggcagcgg agctgggtga aggctgcggg     180
ttccggcgag gcctgagctg tgctgtcgtc atgcctcaaa cccgatccca ggcacaggct     240
acaatcagtt ttccaaaaag gaagctgtct cgggcattga acaaagctaa aaactccagt     300
gatgccaaac tagaaccaac aaatgtccaa accgtaacct gttctcctcg tgtaaaagcc     360
ctgcctctca gccccaggaa acgtctgggc gatgacaacc tatgcaacac tccccattta     420
cctccttgtt ctccaccaaa gcaaggcaag aaagagaatg gtccccctca ctcacataca     480
cttaagggac gaagattggt atttgacaat cagctgacaa ttaagtctcc tagcaaaaga     540
gaactagcca agttcaccca aaacaaaata ctttcttcag ttagaaaaag tcaagagatc     600
acaacaaatt ctgagcagag atgtccactg aagaaagaat ctgcatgtgt gagactattc     660
aagcaagaag gcacttgcta ccagcaagca aagctggtcc tgaacacagc tgtcccagat     720
cggctgcctg ccagggaaag ggagatggat gtcatcagga atttcttgag gaacacatc     780
tgtgggaaaa aagctggaag cctttacctt tctggtgctc ctggaactgg aaaaactgcc     840
tgcttaagcc ggattctgca agacctcaag aaggaactga aaggctttaa aactatcatg     900
```

| | |
|---|---:|
| ctgaattgca tgtccttgag gactgcccag gctgtattcc cagctattgc tcaggagatt | 960 |
| tgtcaggaag aggtatccag gccagctggg aaggacatga tgaggaaatt ggaaaaacat | 1020 |
| atgactgcag agaagggccc catgattgtg ttggtattgg acgagatgga tcaactggac | 1080 |
| agcaaaggcc aggatgtatt gtacacgcta tttgaatggc catggctaag caattctcac | 1140 |
| ttggtgctga ttggtattgc taatacctg gatctcacag atagaattct acctaggctt | 1200 |
| caagctagag aaaaatgtaa gccacagctg ttgaacttcc caccttatac cagaaatcag | 1260 |
| atagtcacta ttttgcaaga tcgacttaat caggtatcta gagatcaggt tctggacaat | 1320 |
| gctgcagttc aattctgtgc ccgcaaagtc tctgctgttt caggagatgt tcgcaaagca | 1380 |
| ctggatgttt gcaggagagc tattgaaatt gtagagtcag atgtcaaaag ccagactatt | 1440 |
| ctcaaaccac tgtctgaatg taaatcacct tctgagcctc tgattcccaa gagggttggt | 1500 |
| cttattcaca tatcccaagt catctcagaa gttgatggta acaggatgac cttgagccaa | 1560 |
| gaaggagcac aagattcctt ccctcttcag cagaagatct tggtttgctc tttgatgctc | 1620 |
| ttgatcaggc agttgaaaat caaagaggtc actctgggga agttatatga agcctacagt | 1680 |
| aaagtctgtc gcaaacagca ggtggcggct gtggaccagt cagagtgttt gtcactttca | 1740 |
| gggctcttgg aagccagggg cattttagga ttaaagagaa acaaggaaac ccgtttgaca | 1800 |
| aaggtgtttt tcaagattga agagaaagaa atagaacatg ctctgaaaga taaagcttta | 1860 |
| attggaaata tcttagctac tggattgcct taaattcttc tcttacaccc cacccgaaag | 1920 |
| tattcagctg gcatttagag agctacagtc ttcattttag tgctttacac attcgggcct | 1980 |
| gaaaacaaat atgacctttt ttacttgaag ccaatgaatt ttaatctata gattctttaa | 2040 |
| tattagcaca gaataatatc tttgggtctt actatttta cccataaaag tgaccaggta | 2100 |
| gaccctttt aattacattc actacttcta ccacttgtgt atctctagcc aatgtgcttg | 2160 |
| caagtgtaca gatctgtgta gaggaatgtg tgtatattta cctcttcgtt tgctcaaaca | 2220 |
| tgagtgggta tttttttgtt tgttttttt gttgttgttg ttttgaggc gcgtctcacc | 2280 |
| ctgttgccca ggctggagtg caatggcgcg ttctctgctc actacagcac ccgcttccca | 2340 |
| ggttgaagtg attctcttgc ctcagcctcc cgagtagctg ggattacagg tgcccaccac | 2400 |
| cgcgcccagc taattttta atttttagta gagacaggt tttaccatgt tggccaggct | 2460 |
| ggtcttgaac tcctgaccct caagtgatct gcccaccttg gcctcctaa gtgctgggat | 2520 |
| tataggcgtg agccaccatg ctcagccatt aaggtatttt gttaagaact ttaagtttag | 2580 |
| ggtaagaaga atgaaaatga tccagaaaaa tgcaagcaag tccacatgga gatttggagg | 2640 |
| acactggtta aag | 2653 |

<210> SEQ ID NO 19
<211> LENGTH: 6721
<212> TYPE: DNA
<213> ORGANISM: Homo sapiens

<400> SEQUENCE: 19

| | |
|---|---:|
| gtccggtcgc cgccgccgcc gccatcgcgg aggagcgcga taaagggagc cgagccggac | 60 |
| gtgagggga ccccgcggag ccgccgcgcc agcgcagccc cccagccgca tcggagtcgc | 120 |
| cagagtccga gccgccgccg ccgccgccgc cgccccgcc gccgccgcgg ctgcccaggg | 180 |
| gccggccagc tccccagccc tgccggggg tcgccgccgc cgccccca gcgtcgcccc | 240 |
| tagcctgcct gccgcctta aatgtgacac cggcgtcgcg gagcgcgacc tgaagccgcc | 300 |
| gccggggagg ggacgagcac catgtcgaat ctgagcaaag gcacgggcag ccggaaggac | 360 |

-continued

```
accaagatgc ggatccgggc ctttccgatg accatggatg aaaaatatgt aaacagcatt    420
tgggaccttc tgaaaaatgc aattcaagaa atccagcgta agaataacag tggtcttagt    480
tttgaggagc tctatagaaa tgcatataca atggttttgc ataaacatgg agaaaagctc    540
tacactggac taagagaagt tgttaccgaa catctcataa ataaggtgcg agaagatgta    600
ctaaattcat tgaataacaa cttcttcaa acgctaaatc aagcttggaa tgatcatcaa    660
acagctatgg tgatgattag agacatacta atgtacatgg accgtgtgta tgtacaacaa    720
aataatgtgg agaacgtcta caatttggga ttaattattt ttcgagatca agttgtacgt    780
tatgggtgta ttagggatca tctacggcaa actctattgg atatgattgc aagagagcgg    840
aaaggagaag tcgtagacag aggcgcaata agaaatgctt gccagatgtt aatgatttta    900
ggtctcgaag gaagatcagt ctatgaagaa gattttgagg ctccttttt ggaaatgtct    960 gcagaatttt ttcagatgga aagccagaaa tttttagcag aaaatagtgc ttcagtatat   1020
ataagaaaag tagaagctag aattaatgaa gaaatagaac gagtgatgca ctgccttgac   1080
aaatcaacgg aagaaccaat tgtaaaggtg gttgaaaggg aactcatttc caagcacatg   1140
aagactatag tagaaatgga gaattctggg ctagtacata tgttgaaaaa tggaaagaca   1200
gaagaccttg gttgcatgta caagttattt agtcgtgtgc caaatggttt gaaaacaatg   1260
tgtgagtgta tgagttccta tttgagggag caaggtaaag ctcttgtttc tgaagaagga   1320
gaaggaaaga atcctgttga ctatatccag ggcttattgg atctgaagag taggttcgat   1380
cgcttcctcc tggaatcatt caacaatgac cgtctcttta acaaactat gcgggtgac    1440 tttgagtatt ttctcaacct caactccagg tctcctgaat acctctcatt atttattgat   1500
gataagctga aaaagggagt caagggcta acagaacaag aagtagaaac aatattggat   1560
aaagcaatgg tcctttttag gttatgcaa gaaaagatg tatttgaacg ttattataaa    1620
caacacttgg caaggagact tctcacaaat aaaagtgttt ctgatgactc tgaaaaaaac   1680
atgatatcta gttaaagac tgaatgtgga tgtcagttca cgtcaaaact ggaaggaatg    1740
tttagggata tgagcatctc aaacacaacg atggatgaat tcaggcaaca tctacaggca   1800
actggtgtat ctttaggtgg tgttgatctt acagtccggg tgctcacgac aggatattgg   1860
cccactcagt cagccacacc aaagtgcaac atcccaccag caccaagaca tgcttttgag   1920
atattcagaa ggttctactt agccaaacac agtggtcgac agctcacact ccagcatcat   1980
atgggttctg cagatctcaa tgccacattt tatggaccag ttaaaaagga agatggatct   2040
gaagttggtg ttggaggtgc acaagtaact ggctctaata cacggaagca catattgcaa   2100
gtttccactt tccagatgac catattaatg ctctttaata atagagaaaa atacacattt   2160
gaggaaattc agcaagagac agatatccct gaaagagagc ttgttagagc cctacagtcc   2220
ctcgcctgtg gtaaaccaac acagcgggtt cttacaaaag aacccaaatc aaaggaaata   2280
gaaaatggtc atatatttac agttaatgat caattcacat ccaaactaca cagagtcaag   2340
attcaaacag ttgctgccaa acaaggtgaa tccgacccag agaggaaaga aacaaggcag   2400
aaagtagacg acgacagaaa acatgagata gaagctgcta tagtgcggat aatgaaatct   2460
agaaagaaga tgcagcacaa tgttctagta gcggaggtaa ctcagcagtt gaaggcgcga   2520
ttcttaccaa gtccagttgt tattaagaaa cgtattgaag gacttattga gagagaatat   2580
ttggcacgaa cacctgagga tcgcaaagta tacacatatg tagcataaaa tgcgttcaga   2640
aatttgattt attcttggac tgtactcttc gcatggactg ggaagttctt ttaaatcatt   2700
aaatattaag acgaccatct cttctattaa attacagtac atgttctaga ccattgagat   2760
```

```
caagccttta ctcccttgga gagtttccaa catcagttga ttgagcttca ggctttacaa    2820
cgtttatccc tgtagagatc atctttacag ttcctcggga aaatgtgaat gtgctgcgtt    2880
ttgttttctt tactgtatga aaacaggaaa ataaaagaga aatttagaaa atacagctca    2940
ttacaataaa attgttggat ttcatttccc caggtcttca gtgttgatgt aaatgtgttt    3000
tgtagtgttg cttagcactt tgcgcattgt gtaagttggg taacaaaaat ggcaaaagaa    3060
atgcagattt cccagttatc ttgctctgaa gacatttctt tagctagtct tatttaattt    3120
taaaggtttg ataaatatac aaagacccaa gcatacaatt tgagcatgct gtattctacc    3180
acttgcactt actcatcttc tagccttatg accaggaacc tttgttttgg gctcaagtac    3240
acatcctgat ttggtttctc cctgttgtaa tttgagattt cccaaattaa gtcttataat    3300
gattaggttt tgttctgagt tatttctaga gaaagaaagt attttagtat gtgtaaattg    3360
tacaataatt ttttgctgt tgtactcact gctaatagtg gattgtatag ggtggtgttt    3420
ttatttcatt tattgtagac aaaaataatg aatttagtat acacataccc actaattcaa    3480
gtatgtcaga gcacaaagtt ggcagctggt tatatttaat tcagcccctc tgaaaagcac    3540
atacagtcta tactttgttt ataaatacc taggtcctcc ctgcccctaa atatatattt    3600
tggtgaagct gtggtgcact attaatttc tgtttcaaaa tgcaatctaa agatgcaata    3660
aatatgatga ccttgatagt tttaatgaaa tcttcaattc ttgcagctgt gttttggaaa    3720
gtgattaagc aatatttctc aaacctgatg attcttggat atttagctat tgtcctccaa    3780
agagtcatcg tttcacgttt tcaaacatgt gctttgtgct gaagattctt gtcagatatc    3840
ctgtgcttcc agagtatttt tatcttcaat tttattaat tttgtttcat tttgtttca    3900
taagacaatg tttcagatat gtaatgggc aaaccactat agattctgt tggatagaaa    3960
aatgaaatgt tactaataag tttaaattga cccttcgttg actatcagta ctgttgatac    4020
atttattaga atgtatgtct cagaagatgg tttctgttta aatttatggt caagttacaa    4080
caactgaatt ctaatatgga ttaaaaactc cacataaata ttttccca tgcgtcttgg    4140
gttataattt tccttttaga cttgcaaata tgcttttatt gcaattttgt ctccatctgt    4200
actgtagaat tacaagcctt gtgctcttta tctctacatt ttccacttct acatgatgca    4260
attaagatgc caatgaaaag tattgtgaac attattctca ggacactttt accatacttg    4320
agtagtacta agtcaggtgt aacatggaaa gctaagggtt tcaccttctg attttgacat    4380
aattggaaat tttctataat ggtaagatgt ttataggaaa gtaatggtag ttcatgtttg    4440
agaattttt ttattgcttt catttcccag ttaaatgata tttaacacct gggaaaacag    4500
gacagctcag attgtcgagt tagtaaacat gagcgatgta aaactttat ttgaaatctc    4560
ctaagtgaga cattaaacat tttagtgcta gtttaagcca ttaaaagtaa agtttaagtt    4620
tacgtcattg tctcaagtgt ggctgtaaaa atcagatcta gagtttagag acatacttgt    4680
taactttgga gcacaggttt gatatttatg cttctaaata cattaaaaca tttctgaatt    4740
gcagttgaat ggttggagat tgctggcgat gtgatgctgc actgaaaaaa ctggtcacac    4800
aaaatgttta tatgtttgac tgcataagta ttattttagg tcataaaggt tataacaaaa    4860
tacatttaac attgctttct ttttagcaag aggtcacaga tgctatttt tctcagtttt    4920
taatgcttta atttgaaaga aaaatgcatc ctaaccattc catcctgttg gtgcagagaa    4980
attttggtga tttattagaa gacttttaag gagggtggat acatagtttt tcaactgcaa    5040
aaatcatgtc atctcttcag taactgttaa agtgtaattc tctgccttca ttatcaagtc    5100
caggacagtg tttatttga atcgttaaca ttatttaaag actgaaaatt cattgcaatt    5160
```

```
agggaacgca cagcctcaca aaagtggttg tgattgcaag gattctttat gtcagtgaac    5220 ttaaaaggg aatgggggaa gagatgcatg cctttctaaa ggtatgctag agtcacctgt     5280
gtagcattgt aattatgtac tatcaaaccc ccaagatgct gatgataggc cttctctgta    5340
agaatccttc tcatagtgaa gcactgttga tgttttgttc accggatatg ttgggtagca    5400
gaaaaggcct agaaccagtt ttaagattat gcctacatct ctagaagact agtacactgg    5460
catcatctta ggtttctaaa tattatttaa ttccttaatt tggaaagcag ttttaatgtt    5520
tacagtttaa gatactcatt ttcagtaact agtgttaaag attttatct ttgcctgtct     5580 actgtaactt aagactttca tagaataatt ttttatagag tatatggtat attgtgtcaa    5640
tcttggaagg aaagctgttg catatcaatt gtaggtcatg tattttacta tatgttgcat    5700
agtattttgc attctgtaaa tacgaatgtt aaaacatttc aggtcagcaa aattagaagt    5760
catttctagt cctcaaagca gaaataatta gaaatgttaa catttaagtg cttatcatat    5820
gccagatact attctgaata ttttatgtat attcattcat ttagttgtca tattggcttt    5880
atgtgacata actgtcatta taccagtgtt gtccaaggtt gctagcagga aatggcagag    5940
ccaggagttg gacctaggtt taatcctatc catattccat gttacaaatt gacatgattt    6000
tccatattaa aaaattttca tttatttgt acctcattca catgaatagt aatgtgacaa     6060
actaaagtta atacatgaag cattgcaata tggaattttg cacatttttg ttagctttac    6120
attatttgct gataccaact tttggtagga aggaaaacag ggaaggtgat tgctgctatt    6180
ctggaatgtg tccattgaaa agaaaatagg cgctttgtct cctacaatct tagagaaagt    6240
tttacatact taagtgggta ccacagatag gcatgtacct taaattcaaa tctacagttt    6300
tacaaaatgt tttcctttgt gtgccttttcc tatgtcaaat tagccagaag gaagaagaga   6360
cgttaagaat ggcagataaa tttaacaggt aatgatacag agattggcca ttacgctagc    6420
tctcaggaga aaacaacta ggatgtcttg aaacccgtgc atttaatttt agaaatggca     6480
aatttgtaag cgtgtcattt aagtaatttg atgctcagtt ttagggtcta agttgacctc    6540
gagtgagcca tgcaaaaata gctttaaaat tatacatgag cagctcaaag taaacgtgta    6600 tttttttagta acaatgaaat tgtcaaattt caagatttta ataacaggac agttcaacta    6660
ataaacttta ttgcatacaa gatttattgc aatgtgggaa aattaaaatt ctcagtctca    6720
g                                                                    6721
```

<210> SEQ ID NO 20
<211> LENGTH: 831
<212> TYPE: DNA
<213> ORGANISM: Homo sapiens

<400> SEQUENCE: 20

```
cggacgcgtg gggtcgtgcc ctgcgcgtga gcagctgcag cggcagaggc agcatccagc     60
ggcggcgcca gcagttccag tccgttgctt tacttttgc ttcaccgaca tagtcattat     120
gccgaagaga aagtctccag agaatacaga gggcaaagat ggatccaaag taactaaaca    180
ggagcccaca agacggtctg ccagattgtc agcgaaacct gctccaccaa aacctgaacc    240
caaaccaaga aaaacatctg ctaagaaaga acctggagca aagattagca gaggtgctaa    300
agggaagaag gaggaaaagc aggaagctgg aaaggaaggc acagaaaact gaatctgtag    360
ataacgaggg agaatgaatt gtcatgaaaa attggggttg attttatgta tctcttggga    420
caacttttaa aagctatttt taccaagtat tttgtaaatg ctaattttt aggactctac     480 tagttggcat acgaaaatat ataaggatgg acattttatc gtctcatagt catgcttttt    540
```

-continued

```
ggaaatttac atcatcctca agtaaaataa atatcagtta aatattggaa gctgtgtgta      600
agattgattc agcattccat gcacttgctt taaaatttag tcctgtgcat actgtggtgt      660
ttttactgtg catatttgaa tttttcatgc agttttttcta gagcaataat cagtggtgct     720
tttgtaccta ggttttatgt gattttaatg aaacatggat agttgtggcc acctgctgac      780
tatttgtggt ttaaaataaa aggtttactt gtctgcaaaa aaaaaaaaa a                831
```

<210> SEQ ID NO 21
<211> LENGTH: 767
<212> TYPE: DNA
<213> ORGANISM: Homo sapiens
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (658)..(658)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t

<400> SEQUENCE: 21

```
atccagcggc ggcgccagca gttccagtcc gttgctttac ttttttgcttc accgacatag     60 tcattatgcc gaagagaaag tctccagaga atacagaggg caaagatgga tccaaagtaa     120
ctaaacagga gcccacaaga cggtctgcca gattgtcagc gaaacctgct ccaccaaaac     180
ctgaacccaa accaagaaaa acatctgcta agaaagaacc tggagcaaag attagcagag     240
gtgctaaagg gaagaaggag gaaaagcagg aagctggaaa ggaaggtact gcaccatctg     300
aaaatggtga aactaaagct gaagaggtac tttccataaa tacctcccac tgattgaatc     360
agtgtcttta aagaaatttc tcaatccttc agccggtgat agcacgttct taatgtctct     420
ttttattgcc tgtaatgtta ttgcagatcc acatctctcg ctcaactgtt aatgtctcaa     480
cctccagagg cacccacccc agcacactgt cagtaaaggg gcagattgaa acagtgagag     540
ttaagggtac agtagaaaat tctgcatgtt tgcagtgact agaatcagat agtagtgngg     600
ggggtttttt ttttaatcat tatgaagagt gggagcttgc angtaangct tctgnggngg     660
tttgaaaagc agnaaagcaa taaatggaaa caaaggggnt gggaaatat attcctggcc     720 ttggcttctt cactcaaaaa ttgaaataag gtttgcagta aagctgg                   767
```

<210> SEQ ID NO 22
<211> LENGTH: 1519
<212> TYPE: DNA
<213> ORGANISM: Homo sapiens

<400> SEQUENCE: 22

```
cagcccctgc tttccctagt tccagttcca agatggggaa atccttcgcc aacttcatgt        60
gcaagaaaga ctttcatcct gcctccaaat ccaatatcaa aaagtatgg atggcagaac        120
agaaatatc atatgataag aagaaacaag aagaattgat gcagcaatat cttaaagaac         180
aagaatcata tgataataga ttgcttatgg gagatgaacg tgtaaagaat ggccttaatt        240
tcatgtatga agccccacca ggagctaaaa aagaaaacaa agagaaagaa gaaacagaag        300
gagagaccga atacaaattt gaatggcaga aaggagcccc acgagaaaaa tatgccaaag        360
atgcacatgaa catcagagat cagcccttg gtattcaggt tcgaaatgtg aggtgcatta       420
aatgtcacaa atgggtcatg tcaacacaga tcgagaatgt cctttgtttg gtctttctgg        480
aagtcaatgc aagttcggtt cccactgatg gctcagggcc atcgatgcac ccctcggagc        540
taataggcga gatgagaaac cagtgggttt gcactgaaac gaaatgtact ggggagaaac        600
ttgaccgcaa actgatccat cacaggagta tgttgcaagt gcagggtgaa gaagatccag        660
aagttgaatt tttaaagtca ctaacaacca acaaaaaca gaaacttctc aggaaattag        720
atcgactgga gaagaaaaaa aagaaaaaag atagaaaaaa gaaaaagttt cagaagagca        780
gaagtaaaca caaaaaacat aagtcctctt cttcctatct tcctcctcct cctcctcttc        840
ctctactgag acttcagaaa gcagtagtga gagtgagagt aacaataaag aaaaaaaaac        900
tacaaaggaa gaaaagaaag aaaaacaagt gttcagggca taacaacagt gattctgaag        960
agaaggacaa gtctaagaag agaaagcttc atgaagaact ttctagcact caccataacc       1020
gggaaaaagc caaggaaaag cccaggttct taaaacacga gagttctagg gaggacagca       1080
aatggagcca ttctgattct gacaaaaagt ccagaaccca taaacatagc ccagagaaga       1140
gaggctctga agaaaggag gggagcagca gaagccacgg cagggaggaa aggagccgga       1200
gaagccagcc agaagtcctg gtagttacaa gcaaagggag acaaggaaac gggcacagcg       1260
aacatcctgg tgaagagcaa agcagaagaa atgacagcag aagccatggc acagacttgt       1320
atagaggaga aaaatgtac agagagcacc caggaggtac acatactaaa gtgcacaaaa       1380
gagaatgaag cagaagtaga aagaaagac tgtatgtgac aattacctgg gaataaaaat       1440
atctccactt ttttattgaa tacctttagc aaggggtaaa ttatatactg ttgtctttct       1500
aataaaaag ctcaatttt                                                     1519
```

<210> SEQ ID NO 23
<211> LENGTH: 1280
<212> TYPE: DNA
<213> ORGANISM: Homo sapiens

<400> SEQUENCE: 23

```
gaccgcagtc ggagtctgca gagtgttggg tctgtagcca gcaaattact tcatcatcta        60
gattatccat tcagttgatc ctaattagca aggataacaa ggtaacacaa ggcttactta       120
tattcaccca acaaaagtgt ctctgtggag ccacttccca gtgaactaca tactgagata       180
ggggttcctg gatgagaagg accaaggaca gaaccgagaa gagtttaggg gcaggttatg       240
cgagatggaa atgcgcaga taacggaggg aaggatttga gggctcaaac gtaggcgtct       300
gtgtttcgca aaagttggag acgttctagg ctgcctctcg ttgcctccat ctcgctctgc       360
gcgggttttg gaggacatta gcattctttc ttgtatctcc gttgattcca agaatcgtcc       420
gcactaaagt cccctgcagc gtgaccatgt cgagaccccg aagaggctg ctgggactt        480
ctggttcaga caagggacta tcaggaaaac gcaccaaaac tgagaactca ggtgaggcat        540
```

```
tagctaaagt ggaggactcc aaccctcaga agacttcagc cactaaaaac tgtttgaaga       600
atctaagcag ccactggctg atgaagtcag agccagagag ccgcctagag aaaggtgtag       660
atgtgaagtt cagcattgag gatctcaaag cacagcccaa acagacaaca tgctgggatg       720
gtgttcgtaa ctaccaggct cggaacttcc ttagagccat gaagctggga gaagaagcct       780
tcttctacca tagcaactgc aaagagccag gcatcgcagg actcatgaag atcgtgaaag       840
aggcttaccc agaccacaca cagtttgaga aaacaatcc ccattatgac ccatctagca        900
aagaggacaa ccctaagtgg tccatggtgg atgtacagtt tgttcggatg atgaaacgtt       960
tcattcccct ggctgagctc aaatcctatc atcaagctca caaagctact ggtggccct       1020 taaaaatat ggttctcttc actcgccaga gattatcaat ccagcccctg acccaggaag      1080
agtttgattt tgttttgagc ctggaggaaa aggaaccaag ttaactgaga tactgctgct      1140
ggaatgggcg agacattgct gcaaagaagt caagcttttt tcagacaaaa ggtgtgaggg      1200
ggcttgcttg gtatgcttac ctgggcttgt gtacctcagt ggttttttgtg tactttttc      1260 aataaaatat caaagttgaa                                                  1280

<210> SEQ ID NO 24
<211> LENGTH: 987
<212> TYPE: DNA
<213> ORGANISM: Homo sapiens

<400> SEQUENCE: 24
atgtctatgc tggctgaacg tcggcggaag cagaagtggg ctgtggatcc tcagaacact        60
gcctggagta atgacgattc caagtttggc cagcggatgc tagagaagat ggggtggtct       120
aaaggaaagg gtttagggc tcaggagcaa ggagccacag atcatattaa agttcaagtg        180
aaaaataacc acctgggact cggagctacc atcaataatg aagacaactg gattgcccat       240
caggatgatt ttaaccagct tctggccgaa ctgaacactt gccatgggca ggaaaccaca       300
gattcctcgg acaagaagga aaagaaatct tttagccttg aggaaaagtc caaatctcc       360 aaaaaccgtg ttcactatat gaaattcaca aagggaagg atctgtcatc tcggagcaaa       420
acagatcttg actgcatttt tgggaaaaga cagagtaaga agactcccga gggcgatgcc       480
agtccctcca ctccagagga gaacgaaacc acgacaacca gcgccttcac catccaggag       540
tactttgcca gcggatggc agcactgaag aacaagcccc aggttccagt tccagggtct       600
gacatttctg tgacgcaggt agaacgtaaa aggggaaga aaagaaataa agaggccaca       660
ggtaaagatg tggaaagtta cctccagcct aaggccaaga ggcacacgga gggaaagccc       720
gagagggccg aggcccagga gcgagtggcc aagaagaaga gcgcgccagc agaagagcag       780
ctcagaggcc cctgctggga ccagagttcc aaggcctctg ctcaggatgc aggggaccat       840
gtgcagccgc ctgagggccg ggacttcacc ctgaagccca aaaagaggag agggaagaaa       900
aagctgcaaa aaccagtaga gatagcgag gacgctacac tagaagaaac gctagtgaaa       960
aagaagaaga agaaagattc caaatga                                          987
```

SUBSTRATES OF N-END RULE UBIQUITYLATION AND METHODS FOR MEASURING THE UBIQUITYLATION OF THESE SUBSTRATE

1. CROSS REFERENCES TO RELATED APPLICATIONS

This application is a divisional of application Ser. No. 10/693,999, filed Oct. 28, 2003, now U.S. Pat. No. 7,608,682; which claims priority to Provisional Application No. 60/422,448, filed Oct. 30, 2002, and Provisional Application No. 60/486,529 filed Jul. 12, 2003, the entire contents of which are hereby incorporated by reference in this application.

2. FIELD OF INVENTION

The present invention relates to detecting and measuring protein ubiquitylation via the N-end rule pathway and to identifying novel targets, enzymes and modulators of N-end rule ubiquitylation.

3. BACKGROUND

The ability to degrade proteins is an essential function of all eukaryotic cells. The ubiquitin-proteasome system has evolved to play an active role in cellular quality control by selective degradation of normal or damaged proteins. The ubiquitin-proteasome system is fundamental to cell cycle control, transcriptional regulation, stress response, immune and inflammatory responses and other vital processes (Hershko and Ciechanover, 1998, *Annu. Rev. Biochem,* 67:425-479; Varshavsky, 1997, *Trends Biochem. Sci.,* 22: 383-387; Hochstrasser, 1996, *Annu. Rev. Genet,* 30: 405-439).

Ubiquitin (Ub) is a highly conserved 76-amino acid protein. Protein degradation via the ubiquitin-proteasome pathway generally involves covalent attachment of multiple molecules of ubiquitin to the protein substrate. The protein substrate is subsequently degraded by the 26S proteasome complex, and the free ubiquitin is recycled. There are also examples of proteins whose functions appear to be regulated by ubiquitylation, although ubiquitylation does not appear to target them for degradation (Hwang et al., 2003, *Mol. Cell,* 11: 261-266).

The attachment of ubiquitin to many known substrate proteins is believed to occur in a series of enzymatic reactions carried out sequentially by three classes of proteins: (1) an ubiquitin-activating enzyme (E1) activates ubiquitin in an ATP-dependent manner to form a thioester bond between the carboxy-terminal Gly of Ub and a Cys residue of E 1; (2) activated Ub is then transferred to an ubiquitin-conjugating enzyme (E2 or UBC) to form another thioester bond, (3) a ubiquitin ligase (E3) catalyzes or promotes, in a substrate specific manner, the transfer of Ub from the E2 to a Lys residue of the substrate protein to form an isopeptide bond. An internal Lys residue of Ub can also form an isopeptide bond with the C-terminus of another Ub to create a multi-Ub chain that serves as a targeting signal for proteasome.

In addition to ubiquitylation, proteins can be modified by attachment of ubiquitin-like proteins (such as Sentrin/SUMO or NEDD8) through distinct pathways that may have physiological roles distinct from the ubiquitylation pathway (Yeh et al., 2000, *Gene,* 248: 1-14). While there are at least 25 mammalian E2 family members, some poorly characterized, the number of different E3 enzymes is predicted to gross over a hundred (Weissman, 2001, *Nature Reviews,* 2: 169-178). E3 ubiquitin ligases come in a variety of different structural classes (such as HECT and RING finger) and act via a number or distinct pathways. So far, most E3 proteins that have been shown to interact with E2s and to mediate ubiquitylation in in vitro systems lack defined substrates other than themselves. The currently available information on E3 identification and specificity is insufficient to develop clear understanding of the role of many E3s in biological processes and disease.

The defective regulation of the ubiquitin-proteasome system manifests in diseases that range from developmental abnormalities and autoimmunity to neurodegenerative diseases and cancer (Weissman, 2001, *Nature Reviews,* 2: 169-178). The discovery of HECT E3s was a direct consequence of the finding that oncogenic strains of human papillomavirus (HPV) encode isoforms of a protein called E6, which specifically inactivates the tumor suppressor protein p53. E6 serves as an adaptor between p53 and an E6-associated E3 that catalyzes the ubiquitylation of p53 (Scheffner et al., 1993, *Cell,* 75:495-505). Mutations in the same HECT E3 enzyme are shown to give rise to Angelman syndrome, a severe neurologic disorder (Kishino et al., 1997, *Nature Genet.,* 15: 70-73). Prominent among RING E3s is a product of breast and ovarian cancer susceptibility gene (BRCA1). Mutations in this protein are found in familial forms of breast and ovarian cancer (Brzovic et al., 1998, *J. Biol. Chem.,* 273: 7795-7799). Among well-studied RING E3s are the oncoprotein MDM2, an E3 ligase that ubiquitylates p53 and upon overexpression may lead to cancer; the proto-oncoprotein c-Cbl which ubiquitylates growth factor receptors (Waterman et al., 1999, *J. Biol. Chem.,* 274: 22151-22154; Joazeiro et al., 1999, *Science,* 286: 309-312; Yokouchi et al., 1999, *J. Biol. Chem.,* 274: 31707-31712) and the inhibitors of apoptosis (IAP) proteins (Yang et al., 2000, *Science,* 288: 874-877; Hwang et al., 2000, *J. Biol. Chem.,* 275: 26661-96664). Mutations in Parkin, another RING finger E3, are associated with juvenile Parkinson's disease (Shimura et al., 2000, *Nature Genet.,* 25: 302-305; Chung et al., 2001, *Nature Med.,* 7(10): 1144-1150).

One specific example of an important ubiquitylation pathway is N-End rule ubiquitylation, and especially N-End rule ubiquitylation where ubiquitylation is preceded by N-terminal segment cleavage, where the N-terminal segment comprises one or more amino acid residues. The proteolysis exposes an N-degron which comprises a destabilizing N-terminal residue plus an internal Lys residue where a multi-Ub chain is later attached. The N-terminal segment is cleaved to form an activated substrate of the Ub-dependent N-end rule pathway (activated fragment) which is recognized through exposed destabilizing N-terminal residue.

The N-end rule pathway has been the subject of several review articles; see, e.g., Varshavsky, 1996, *Proc. Natl. Acad. Sci. U.S.A.,* 93: 12142. The ubiquitin ligase UBR1, an E3 ligase, has been shown to ubiquitylate N-end rule substrates and has two binding sites for primary destabilizing N-terminal residues. The type I site is specific for basic N-terminal residues Arg, Lys, His. The type II site is specific for bulky hydrophobic residues Phe, Leu, Trp, Tyr, and Ile. Dipeptides carrying type I or type II N-terminal residues can serve as inhibitors of ubiquitylation of the corresponding type I or type II N-end rule substrates (Gonda et al., 1989, *J. Biol. Chem.,* 264: 16700-16712). UBR1 from yeast contains yet another substrate-binding site, which recognizes proteins for ubiquitylation through an internal recognition site on substrates; this process can be enhanced by the presence of type I and type II dipeptides (Turner et al., 2000, *Nature,* 405: 579-583).

The degradation signal for ubiquitylation via the N-end rule pathways is termed an N-degron and comprises the primary destabilizing N-terminal residue and an internal lysine which is the site of ubiquitylation. Destabilizing N-terminal residues can be generated through proteolytic cleavages of specific proteins and other N-terminal modifications which reveal destabilizing residues at the new N-terminus. The residues that are exposed or modified to reveal an N-degron have been termed a pre-N-degron or pro-N-degron. For example, Sindbis virus RNA polymerase is produced during viral infection through site-specific cleavage of the viral polyprotein precursor and carries an N-terminal Tyr that has been shown in rabbit reticulocyte lysates to target the protein for ubiquitylation via the N-end rule pathway (deGroot et al., 1991, *Proc. Natl. Acad. Sci. U.S.A.*, 88: 8967-8971). Another example is RGS4, whose N-terminal degradation signal is generated through a series of N-terminal modifications including (i) removal of N-terminal Met and exposure of Cys-2 at the N-terminus, (ii) oxidation of Cys-2 into cysteic acid, and (iii) conjugation of Arg to the N-terminus of the protein (Kwon et al., 2002, *Science*, 297: 96-99).

Very few N-end rule substrates are characterized to date. However, recently discovered N-end rule substrates linked to disease or pathology demonstrate the biological importance of N-end rule ubiquitylation pathway. For example, a carboxy-terminal fragment of cohesin in *Saccharomyces cerevisiae* is a physiological substrate for the ubiquitin/proteasome-dependent N-end rule pathway. Overexpression of this fragment is lethal and, in cells that lack an N-end rule ubiquitylation pathway, a highly increased frequency of chromosome loss is detected (Rao et al., 2001, *Nature*, 410: 955-959). Recent studies also indicate that enhanced protein breakdown in skeletal muscle leading to muscle wasting in patients with acute diabetes results from an accelerated Ub conjugation and protein degradation via the N-end rule pathway. The same pathway is activated in cancer cachexia, sepsis and hyperthyroidism (Lecher et al., 1999, *J. Clin. Invest.*, 104: 1411-1420; Solomon et al., 1998, *Proc. Natl. Acad. Sci. USA*, 95: 12602-12607).

Aprataxin is a member of the HIT (histidine triad) protein family, named for the HφHφHφφ motif, where φ is a hydrophobic amino acid (Brenner, 2002, *Biochemistry*, 41(29): 9003-9014). HIT is a superfamily of nucleotide hydrolases and transferases, which act on the alpha-phosphate of ribonucleotides, and contain an approximately 30 kDa domain that is typically a homodimer of approximately 15 kDa polypeptides with two active sites. The superfamily is also generally said to include GalT-like proteins even though these contain a slightly different motif (HXHXQφφ), the motif being repeated twice in a single polypeptide chain that retains a single active site.

Members of the HIT superfamily of proteins have representatives in all cellular life. On the basis of sequence, substrate specificity, structure, evolution, and mechanism, HIT proteins can be classified into the Hint branch, which consists of adenosine 5'-monophosphoramide hydrolases, the Fhit branch, which consists of diadenosine polyphosphate hydrolases, and the GalT branch, which consists of specific nucleoside monophosphate transferases, including galactose-1-phosphate uridylyltransferase, diadenosine tetraphosphate phosphorylase, and adenylyl sulfate:phosphate adenylytransferase. A loss of at least one human representative of each branch is associated with a human disease (Brenner, 2002, *Biochemistry*, 41: 9003-9014). Fhit is lost early in the development of many epithelially derived tumors. GalT is deficient in galactosemia. Aprataxin, a Hint branch hydrolase, is mutated in ataxia-oculomotor apraxia syndrome (Date et al., 2001, *Nature Genetics*, 29: 184-188; Moreira et al., 2001, *Nature Genetics*, 29: 189-193), which is the most common autosomal recessive neurodegenerative disease among Europeans and people of European descent and the most frequent cause of autosomal recessive ataxia in Japan. Recent studies in patients with early-onset ataxia identified one insertion and two missense mutations in the aprataxin gene product (Shimazaki et al., 2002, *Neurology*, 59: 590-595). It has been suggested that aprataxin is involved in DNA repair and therefore its regulation is crucial for cancer predisposition and cerebellar neuron survival (Moreira et al., 2001, *Nature Genetics*, 29: 189-193; Durocher et al., 2000, *Mol. Cell*, 6: 1169-1182). The molecular targets and pathways involving aprataxin remain to be discovered. With identification of such targets and pathways, it is hoped that new light can be shed on brain development and motor coordination.

Microtubule-associated protein tau (MAPT or tau) is a protein that is believed to play a role in a variety of disease processes. The gene encoding tau undergoes complex, regulated alternative splicing, which gives rise to several mRNA species. Six tau isoforms are produced in adult human brain by alternative mRNA splicing from a single gene. The isoforms differ from each other by the presence or absence of 29-amino acid or 58-amino acid inserts located in the N-terminal half and a 31-amino repeat located in the C-terminal half. Inclusion of the latter, which is encoded by exon 10 of the tau gene, gives rise to three tau isoforms with four repeats each; the other three isoforms have three repeats each (Kosik et al., 1989, *Neuron*, 2: 1389-1397; Goedert et al., 1989, *Neuron*, 3: 519-526). The repeats and some adjoining sequences constitute the microtubule-binding domains of tau. Similar levels of 3-repeat and 4-repeat tau isoforms are found in normal cerebral cortex. The tau filaments from Alzheimer disease brain contain all six tau isoforms in a hyperphosphorylated state. At the same time, it is shown that the ratio of 3-repeat to 4-repeat tau isoforms is an important determinant of the ratio of microtubule-bound and free forms of tau (Lu et al., 2001, *Mol. Biol Cell*, 12: 171-184). It has also been demonstrated that longer 4-repeat tau isoforms have approximately 4.5 times higher affinity to microtubules and 2-3 fold faster rate of microtubule assembly than 3-repeat tau isoforms (Goedart and Jakes, 1990, *EMBO J*, 9(13): 4225-4230; Butner and Kirschner, 1991, *J. Cell Biol.*, 115(3): 717-730; Gustke et al., 1992, *FEBS Lett.*, 307(2): 199-205).

MAPT transcripts (including splice isoforms and mutations) are differentially expressed in the nervous system, depending on the stage of neuronal maturation and neuron type. The shortest of the six tau isoforms termed 3R0N is specifically abundant in a fetal brain (Goedert et al., 1989, *Neuron*, 3(4): 519-526). In fact, the human brain expresses only 3R0N isoforms that are highly phosphorylated until the postnatal period, and this may imply a specific role of this isoform during axonal growth and synaptogenesis (Kosik et al., 1989, *Neuron*, 2(4): 1389-1397).

Mutations in tau result in several neurodegenerative disorders such as Alzheimer's disease, Parkinson's disease, Pick's disease, frontotemporal dementia, cortico-basal degeneration and progressive supranuclear palsy as well as subcortical gliosis and pallido-nigro-luydian degeneration (Lu et al., 2001, *Mol. Biol. of Cell*, 12: 171-184; Golbe and Lazzarini, 2001, *Mov. Disord.*, 16(3): 442-7 and references therein).

Neurofibrillary tangles made predominantly from intracellular bundles of self-assembled hyperphosphorylated tau proteins are the hallmark features of Alzheimer's disease (Mandelkow et al., 1995, *Neurobiol Aging*, 16(3): 347-354). Studies on the microtubule-associated protein tau in Alzheimer disease have noted that, in the brains of patients with Alzheimer disease, the neuronal cytoskeleton is progressively disrupted and replaced by neurofibrillary tangles of paired helical filaments (PFs), composed mainly of hyperphosphorylated forms of tau (also called 'AD P-tau'). It has also been demonstrated that in solution normal tau associates with the hyperphosphorylated AD P-tau to form large tangles of filaments and that dephosphorylation with alkaline phosphatase abolished the ability of AD P-tau to aggregate in vitro (Johnson and Bailey, 2002, *J. Alzheimer Disease,* 4: 375-398).

It has also been shown that elevated levels of tau inhibit intracellular transport in neurons, particularly the plus-end-directed transport by kinesin motors from the center of the cell body to the neuronal processes (Ebneth et al., 1998, *J. Cell Biol.,* 143(3): 777-794). This inhibition is significant because critical organelles, such as peroxisomes, mitocnondria, and transport vesicles carrying supplies for the growth cone, are unable to penetrate the neurites, leading to stunted growth, increased susceptibility to oxidative stress, and likely pathologic aggregation of proteins such as amyloid precursor protein. It has been concluded that the tau:tubulin ratio is normally low, and that increased levels of tau become detrimental to the cell (Ebneth et al., 1998, *J. Cell Biol.,* 143(3): 777-794).

Synaptotagmin-like proteins (SLPs) are a subfamily of the C2 domain-containing family of proteins and have a high degree of homology to synaptotagmin. The proteins contain two conserved domains at the N-terminus (referred to as SLP homology domains 1 and 2 or SHD1 and 2) and two carboxyl-terminal $Ca^{2+}$-binding motifs (C2 domains) (Pallanck, 2003, *TRENDS Neurosci.,* 26(1): 2-4). The SHD has also been found in other proteins including SLP homologs lacking C2 domains (Slac2). Found in phospholipases and protein kinase C, C2 domains have also been identified in synaptotagmins, a family of proteins involved in regulating neurotransmission. The function of synaptotagmin, as a calcium sensor in SNARE-mediated exocytosis, is extremely complex and finely regulated to allow for coupling the calcium signal to the fast synaptic vesicle exocytosis, which leads to speculations that synaptotagmin evolved to aquire a function beyond calcium/phospholipids binding (Rickman and Davletov, *J. Biol. Chem.,* 2002, [epub]; Yoshihara et al., 2002, *Neuron,* 36: 897-908; O'Connor et al., 2002, *Nature Neurosci.,* 5(9): 823-824). Also the downregulation of synaptotagmin expression in cholinergic neurons of the nucleus basalis in patients with Alzheimer's disease was reported (Mufson et al., 2002, *Neurochem. Res.,* 27(10): 1035-1048), this downregulation is highly specific, as no downregulation was observed for synapsin I, synaptobrevin or SNAP-29 in the same study.

Like synaptotagmin, the SLP and Slac2 proteins are also believed to play a role in regulation of vesicular trafficking (see Strom et al., 2002, J. Biol. Chem., 277: 25423-25430 and Kuroda et al., *J. Biol. Chem.,* 277: 9212-9218 for a description of the role of SHD containing proteins and their relevance to disease states). The SHD is a binding domain for the GTP-bound form of Rab27a, one of the small GTP-binding proteins that are believed to be essential components of the membrane trafficking mechanism of eukaryotic cells (Zerial et al., 2001, *Nat. Rev. Mol. Cell. Biol.* 2, 107-117). The C-terminal domains of the SLP and Slac2 proteins are likely to play a role in the localization Rab27a to specific sites in a cell.

Rab27a is involved in the transport of melanosomes in melanocytes and lytic granules in cytotoxic T-lymphocytes. Griscelli syndrome, a disease caused by a mutation in Rab27 which leads to defects in the transport of melanosomes and lytic granules is characterized by partial albinism and severe immunodeficiency with hemophagocytic syndrome. Overexpression of the SHD sequence led to a dominant negative effect and a defect in the transport of melanosomes in melanocytes that was similar to that observed in Griscelli syndrome patients.

Alternative splicing occurs at the C2 domain locus and variants of the synaptotagmin-like proteins have been identified. Additional splice variants have been suggested but supporting sequence confirmation is not yet available. Also a gene encoding a synaptotagmin-like protein contains a region of weak similarity to murine Gph.

High Mobility Group Chromosomal Protein HMG17 (also known as HMGN2) is a member of the HMG 14/17 (also known as HMGN) family of proteins; which bind DNA with low specificity and share a common DNA-binding motif with members of the HMG 1/2 (also known as HMGB) family of proteins.

Chromosomal proteins HMG-17 and HMG-14 are among the most abundant, ubiquitous, and evolutionarily conserved nonhistone proteins found in the nuclei of higher eukaryotes (Landsman et al., 1986, *J. Biol. Chem.,* 261(16): 7479-7484). A large number of retropseudogenes are scattered over several chromosomes. It has been shown that the nonhistone chromosomal proteins HMG-14 and HMG-17 are encoded by distinct genes, each of which is part of a separate multigene family. These families may have evolved independently from similar genetic elements or from a shared ancestral gene in which the nucleotide sequence coding for the DNA-binding domain of the protein is the most conserved region. The structural differences between the molecules and the differences in their DNA-binding domains suggest that the proteins may be involved in distinguishable cellular functions. It was suggested that they may confer specific conformations to transcriptionally active regions of chromatin (Weisbrod and Weintraub, 1979, *Proc. Natl. Acad. Sci. USA,* 76: 630) thereby changing the transcriptional potential of the chromatin template (Almouzni et al., 1990, *EMBO J.,* 9: 573; Svaren and Chalkley, 1990, *Trends Genet,* 6: 52). Microinjections of antibodies to HMG-17 into human fibroblasts inhibited transcription (Einck and Bustin, 1983, *Proc. Natl. Acad. Sci. USA,* 80: 6735). Some data suggest that HMG-17 binds to chromatin in a tissue specific manner (Brotherton et al., 1990, *Nucl. Acids Res.,* 18: 2011).

The putative role of HMG-17 in chromatin structure and gene expression is supported by its differential expression during cell differentiation (reviewed in Bustin et al., 1992, *CRC Crit. Rev. Eukaryotic Gene Expression,* 2: 137). Analyses of the mRNA levels during the course of erythropoiesis (Crippa et al., 1991, *J. Biol. Chem.,* 266: 2712), myogenesis (Pash et al., 1990, *J. Biol. Chem.,* 265: 4197), osteoblast differentiation of several additional cell lines (Crippa et al., 1990, *Cancer Res.,* 50: 2022) indicate that undifferentiated cell synthesize more HMG mRNA than differentiated cells. Results suggest that myogenic differentiation may require regulated levels of HMG-14 (Pash et al., 1993, *J. Biol. Chem.,* 268: 13632) and that HMG-14 mRNA and protein levels are elevated in tissues from the individuals with Down syndrome (Pash et al., 1991, *Exp. Cell Res.,* 193: 232) and in trisomy-16 mouse (Pash et al., 1993, *J. Biol. Chem.,* 268: 13632).

A 31-amino acid synthetic peptide from HMG17, when injected intravenously, accumulates in the nuclei of tumor endothelial cells and tumor cells and can carry a "payload" such as a fluorescent label to a tumor and into the cell nuclei in the tumor. This result suggests that HMGN2, like HMGB1, may have a role as an extra-cellular signaling molecule (Porkka et al., 2002, *Proc. Natl. Acad. Sci. USA,* 99: 7444-7449).

PIN2-interacting protein 1 (PinX1) is an RNA processing protein, which contains a G-patch domain (Aravind and Koonin, 1999, *Trends Biochem Sci.*, 24: 342-344). The 328-amino acid length of PinX1 protein is predicted from a longest polynucleotide sequence of PINX1 identified in a yeast 2-hybrid assay. The protein contains no known domain structure except for a gly-rich region in its N-terminus and a telomerase (TERT) inhibitory domain (TID) in its C terminus. The prediction is confirmed by a Northern blot analysis which has detected a 1.9-kb PINX1 transcript in all tissues tested. Immunoprecipitation and immunoblot analyses indicate that PINX1 encodes a 45-kD protein in cells (Zhou and Lu, 2001, *Cell,* 107: 347-359).

PinX1 is identified as a Pin2 binding protein in a yeast 2-hybrid assay and confirmed in coimmunoprecipitation, colocalization and pull-down experiments (Zhou and Lu, 2001, *Cell,* 107: 347-359). It is also discovered that PINX1 inhibits telomerase activity and affect tumorigenicity, when the small TID domain of PinX1 binds the telomerase catalytic subunit hTERT and potently inhibits hTERT activity (Zhou and Lu, 2001, *Cell,* 107: 347-359; Kishi and Lu, 2002, *J. Biol. Chem.*, 277(9): 7420-7429).

Telomerase activity is important for normal and transformed human cells and is implicated in oncogenesis. Overexpression of PinX1 or its TID domain inhibits telomerase activity, shortens telomeres, and induces crisis, whereas depletion of endogenous PinX1 increases telomerase activity and elongates telomeres. Depletion of PinX1 also increases tumorigenicity in nude mice, consistent with its chromosome localization at 8p23, a region with frequent loss of heterozygosity in a number of human cancers. Thus, PinX1 is a potent telomerase inhibitor and a putative tumor suppressor (Zhou and Lu, 2001, *Cell,* 107: 347-359; Kishi and Lu, 2002, *J. Biol. Chem.*, 277(9): 7420-7429).

Unlike human PinX1, which inhibits telomerase activity, the putative yeast homolog of PinX1, encoded by the YGR280c open reading frame (ORF), is a component of the ribosomal RNA processing machinery involved in rRNA and small nucleolar RNA maturation (Guglielmi and Werner, 2002, *J. Biol. Chem.*, 277(38) 35712-35719). The protein has a KK(E/D) C-terminal domain typical of nucleolar proteins and a putative RNA interacting domain widespread in eukaryotes called the G-patch. The protein is hence renamed Gno1p (G-patch nucleolar protein). GNO1 deletion results in a large growth defect due to the inhibition of the pre-ribosomal RNA processing first cleavage steps at sites A(0), A(1), and A(2). Furthermore, Gno1p is involved in the final 3'-end trimming of U18 and U24 small nucleolar RNAs. Mutational analysis shows that the G-patch of Gno1p is essential for both functions, whereas the KK(E/D) repeats are only required for U18 small nucleolar RINA maturation.

Human PinX1 expression in the yeast multicopy expression vector pGen in the background of gno1-Delta (deletion of GNO1 gene) phenotype suggests that it has a dual function in telomere length regulation and ribosomal RNA maturation in agreement with its telomeric and nucleolar localization reported in human cells (Guglielmi and Werner, 2002, *J Biol Chem,* 277(38): 35712-35719). Conversely, the same study finds that a full length yeast Gno1p does not exhibit the in vivo telomerase inhibitory activity of PinX1.

CBF1-interacting corepressor (CIR) is a unique CBF1 interacting corepressor, which binds to histone deacetylase and to SAP30 and serves as a linker between CBF1 and the histone deacetylase complex (Hsieh et al., 1999, *Proc Nat Acad Sci,* 96: 23-28). CBF1 (RBPSUh) is a member of the CSL family of DNA-binding factors, which mediate transcriptional activation or repression. The family includes CBF1, 'suppressor of hairless,' and Lag1 (Schweisguth and Posakony, 1992, *Cell,* 69: 1199-1212; Christensen et al., 1996, *Development* (Cambridge, UK), 122: 1373-1383). CSL proteins play a central role in Notch signaling (Artavanis-Tsakonas et al., 1995, *Science,* 268: 225-232). Disruptions and aberrations in Notch signaling are associated with human neoplastic disease, cerebral autosomal dominant arteriopathy with subcortical infarcts and leucoencepholopathy, and Alagille syndrome. CSL proteins also play a central role in and in Epstein-Barr virus-induced immortalization (Zhou et al., 2000, *J. Virol.,* 74(4): 1939-1947; Hsieh et al., 1999, *Proc. Natl. Acad Sci. USA,* 96: 23-28 and references therein), the process associated with human malignancies such as Burkitt's lymphoma, nasopharyngeal carcinoma, Hodgkin's disease and lymphoproliferative disease in immunosuppressed patients. CIR is believed to play an important role in the gene regulation activity of CBF1 by targeting CBF1 recognition sequences for histone deacetylation, an activity which is linked to gene suppression.

Human CIR is a 450-amino acid protein (560-amino acid C. elegans homolog) with a highly charged, serine-rich C-terminus predicted from a polynucleotide sequence identified using a yeast 2-hybrid screen of a B-cell cDNA library with CBF1 as bait (Hsieh et al., 1999, *Proc. Natl. Acad Sci. USA,* 96: 23-28). The widespread expression of CIR is revealed by Northern blot analysis, with strongest expression detected in heart, skeletal muscle, and pancreas. Immunofluorescence analysis shows that CIR is a nuclear protein like CBF1, although CIR does not bind to the nucleolus. It is determined that the N-terminal 121 amino acids of CIR interact with amino acids 233 to 249 of CBF1 and repress transcriptional activity. Yeast two-hybrid assay and immunofluorescence analysis indicate that CIR also interacts with HDAC2 and SAP30, important mediators of transcriptional repression.

Cullin 3, a member of the cullin/Cdc53 family of proteins, is a putative E3 ubiquitin ligase which regulates abundance of other proteins, such as Ci (Ou et al., 2002, *Genes Dev.,* 16(18): 2413-2414), cyclins E and D1 (Singer et al., 1999, *Genes Dev.,* 13: 2375-2387; Winston et al., 1999, *Genes Dev.,* 13: 2351-2357; Maeda et al., 2001, *FEBS Lett.,* 494: 181-185) and katanin (Kurtz et al., 2002, *Science,* 295: 1294-1298) by targeting them for ubiquitin-dependent proteolysis, potentially as a part of a larger complex.

Ci protein is required for cell's ability to sense and interpret graded spatial information and therefore ultimately responsible for cell's fate (Ou et al., 2002, *Genes Dev.,* 16(18): 2413-2414; Jiang J, 2002, *Genes Dev.,* 16: 2315-2321). Overexpression of cyclin D1 has been implicated in a variety of tumors such as breast cancers, gastrointestinal cancers and lymphomas (Maeda et al., 2001, *FEBS Lett.,* 494: 181-185). Cyclin E is an evolutionary conserved protein whose essential function is to promote cell cycle transition from G1 to S thereby coordinating crucial events in the organism (Knoblich et al., 1994, *Cell,* 77: 107-120; Ohtsubo et al., 1995, *Mol. Cell. Biol.,* 15: 2612-2624). Katanin, which has documented microtubule-severing activity, regulates microtubule instability and the loss of katanin completely suppresses all signs of instability (Han et al, 1997, *Nature,* 386: 296; Kurtz et al., 2002, *Science,* 295: 1294-1298) in *C. elegans.*

The cullins represent a conserved gene family, with at least five members in nematodes, six in humans, and three in *S. cerevisiae.* Human CUL3 is an ortholog of nematode cul3 (Winston et al., 1999, *Genes Dev.,* 13: 2351-2357) which is expressed in several tissues as major 2.8- and minor 4.3-kb transcripts in various tissues, with the highest levels in skeletal muscle and heart. CUL3 has been identified as a gene whose expression in human fibroblasts is induced by phorbol 12-myristate 13-acetate (PMA) and suppressed by salicylate.

Homozygous deletion of the Cul-3 gene is shown to cause embryonic lethal phenotype (Singer et al., 1999, *Genes Dev.*, 13: 2375-2387).

The methods developed for monitoring the ubiquitylation activity of cullins, or modulating such activity are described in U.S. Pat. No. 6,426,205 to Tyers et al., and U.S. Pat. Nos. 6,165,731 and 6,413,725 to Deshaies et al., hereby incorporated by reference.

High-mobility group protein HMGN3, also known as a thyroid hormone receptor interacting protein 7 (Trip7), is a member of a class of relatively abundant non-histone nuclear proteins, which function as architectural elements (Bustin and Reeves, 1996, In Cohn, Moldave eds., Progress in Nucleic Acid Research and Molecular Biology, Vol. 54, San Diego, Academic Press, 35-100). HMGN3 (Trip7) is closely related to the small nonhistone chromatin proteins HMG14 and HMG17 (HMGN2), which bind specifically to nucleosomes, reduce the compactness of chromatin fiber and enhance transcription from chromatin templates (Bustin, 2001, *Trends Biochem. Sci.*, 26: 431-437). In addition, a yeast two-hybrid screen in a HeLa cell library indicated that HMGN3 interacts with the ligand binding domain of thyroid hormone receptor beta (TR$\beta_1$), but only in the presence of thyroid hormone (Lee et al., 1995, *Mol. Endocrinol.*, 9: 243-254).

The thyroid hormone receptors (TRs) are hormone-dependent transcription factors that regulate expression of a variety of specific target genes. It is suggested that they are regulated by a number of proteins as they progress from their initial translation and nuclear translocation to heterodimerization with retinoid X receptors (PXRs) and further to functional interactions with other transcription factors and the basic transcriptional apparatus, and eventually, degradation (Collingwood et al., 1999, *J. Mol. Endocrinol.*, 23: 255-275). Interestingly, all Trips (including HMGN3) interact with RXR-alpha (RXRA) in a ligand-dependent manner, but HMGN3 does not interact with the glucocorticoid receptor (NR3C1) under any conditions (Lee et al., 1995, *Mol. Endocrinol.*, 9: 243-254).

Northern blot analysis detects a 1.1-kb TRIP7 transcript in several tissues, with highest expression in heart and kidney (Lee et al., 1995, *Mol. Endocrinol.*, 9: 243-254). Both Northern and Western analysis demonstrate a tissue specific expression pattern in mice with the highest level of expression in whole mouse brain extracts (West et al., 2001, *J. Biol. Chem.*, 276: 25959-25969). The additional immunohistochemical data reveals that the expression of HMGN3 is enriched in specific regions of the mouse brain with relatively high expression in lateral olfactory tract, anterior commissure, corpus callosum, internal capsule, fornix, stria medullans, optic tract and axon bundles (Ito and Bustin, 2002, *J. Histochem. Cytochem.*, 50(9): 1273-1275). The expression pattern most closely resembles the expression pattern of GFAP (glial fibrillary acidic protein) which is considered an important factor in astrocyte differentiation and is part of the reactive response of the CNS to injury (Eng et al., 2000, *Neurochem. Res.*, 25: 1439-1451). The results raise the possibility that HMGN3 protein plays a functional role in the astrocytes of mouse brain (Ito and Bustin, 2002, *J. Histochem. Cytochem.*, 50(9): 1273-1275).

A separate study of an HMGN3 (Trip7) homolog in *Xenopus laevis* implicated the protein in tissue remodeling during the metamorphosis. The study shows that HMGN3 influences basal transcription in a chromatin structure-dependent manner, but enhances the function of liganded TR regardless of the chromatin structure of the promoter (Amano et al., 2002, *Developmental Dynamics*, 223: 526-535).

HSPC144 protein is a homolog of the chicken thymocyte protein (cThy28), a protein that is suggested to mediate avian lymphocyte apoptosis (Compton et al., 2001, *Apoptosis*, 6: 299-314). Avian cThy28 gene is a 1070 bp cDNA encoding a 242 amino acid conserved protein, cThy28 (GenBank accession number U34350) that shares greater than 90% amino acid similarity with several putative mammalian homologues such as mouse mThy28 (226 aa) (Miyaji et al., 2002, *Gene*, 297: 189-196) and a human HSPC144 (225 aa) obtained from a human CD34$^+$ stem cell library. A structural analysis of the protein suggests that it is a nuclear-localized phosphoprotein with potential glycosylation and myristolation sites. Compared to other non-lymphoid tissues, the avian cThy28 protein and its transcript are present in immune organs at elevated levels. The mouse homolog is expressed in testis, liver, brain and kidney with the lower levels of expression in thymus spleen, heart and stomach (Miyaji et al., 2002, *Gene*, 297: 189-196). The high degree of conservation in amino acid sequences among various species including bacteria, yeast and plants as well as vertebrate suggests an indispensable role of the protein in living cells.

Human Cell Cycle Controller CDC6 protein, a protein that is highly similar to *Saccharomyces cerevisiae* Cdc6 protein, is essential for the initiation of DNA replication (for review see, Bell and Dutta, 2002, *Annu. Rev. Biochem.*, 71: 333-374; Lee and Bell, 2000, *Curr. Opin. Cell Biol.*, 12: 280-285; Lei and Tye, 2001, *J. Cell Sci.*, 114: 1447-1454; Coleman, 2002, *Curr. Biol.*, 12(22): R759). Cdc6 is part of a macromolecular machine that assembles on chromatin to target the DNA for a single round of replication. Cdc6 (*Saccharomyces cerevisiae*) and Cdc18 (Schizosaccharomyces pombe) collaborate with the six-subunit origin recognition complex (ORC, Orc1) (Cocker et al., 1996, *Nature*, 379: 180-182; Tanaka et al., 1997, *Cell*, 90: 649-660), Cdt1 (Maiorano et al., 2000, *Nature*, 404: 622-625; Nishitani et al., 2000, *Nature*, 404: 625-628) and with the DNA replication proteins (PCNA, RPA) to recruit minichromosome maintenance (MCM) family of proteins to DNA, thereby forming the pre-replication complex.

Human CDC6 localizes in cell nucleus during cell cycle G1, but translocates to the cytoplasm at the start of S phase, suggesting that DNA replication may be regulated by either the translocation of this protein between the nucleus and cytoplasm or by selective degradation of the protein in the nucleus, as revealed by immunofluorescent analysis of epitope-tagged protein (Delmolino et al., 2001, *J. Biol. Chem.*, 276(29): 26947-26954). The subcellular translocation of Cdc6 during cell cycle is also regulated through its phosphorylation by Cdks at nuclear localization signals or at nuclear export signals or at sites adjacent to these (Delmolino et al., 2001, *J. Biol. Chem.*, 276(29): 26947-26954).

There is evidence that human Cdc6 regulates the onset of mitosis, as overexpression of human Cdc6 in G2 phase cells prevents entry into mitosis by blocking cells in G2 phase via a checkpoint pathway involving Chk1 (Clay-Farrace et al., 2003, *EMBO J.*, 22(3): 704-712). Transcription of human Cdc6 is regulated in response to mitogenic signals through transcriptional control mechanism involving E2F proteins, as revealed by a functional analysis of the human Cdc6 promoter and by the ability of exogenously expressed E2F proteins to stimulate the endogenous Cdc6 gene (Ohtani et al., 1998, *Oncogene*, 17: 1777-1785; Hateboer et al., 1998, *Mol. Cell. Biol.*, 18(11): 6679-6697).

Northern blots indicate that CDC6/Cdc18 mRNA levels peak at the onset of S phase and diminish at the onset of mitosis in HeLa cells, but total CDC6/Cdc18 protein level is unchanged throughout the cell cycle. Immunoprecipitation studies show that human CDC6/Cdc18 associates in vivo with cyclins (such as cyclin A and B), CDK1 and/or CDK2, and ORC1 (Clay-Farrace et al., 2003, *EMBO J.*, 22(3): 704-712; Yam et al., 2002, *Cell Mol. Life Sci.*, 59: 1317-1326). The association of cyclin-CDK2 with CDC6/Cdc18 is specifically inhibited by a factor present in mitotic cell extracts. It has been suggested that if the interaction between CDC6/Cdc18 with the S phase-promoting factor cyclin-CDK2 is essential for the initiation of DNA replication, the mitotic inhibitor of this interaction could prevent a premature interaction until the appropriate time in G1 (for review see, Yam et al., 2002, *Cell Mol. Life. Sci.*, 591317-1326).

Cdc6 is expressed selectively in proliferating but not quiescent mammalian cells, both in culture and within tissues in intact animals. For example, nuclear human Cdc6 is detected by immunofluorescence in 90% of nuclei in premalignant human cervical tissue (Williams et al., 1998, *Proc. Natl. Acad. Sci. USA*, 95: 14932-14937). Most studies agree that markers of proliferation correlate with patient prognosis (Gerdes et al., 1983, *Intl. J. Cancer*, 31: 13-20; Thapar et al., 1996, *Neurosurgery*, 38: 99-106). The expression of Cdc6 may be used as marker of proliferating cells in various types of tumors (Freeman et al., 1999, *Clin. Cancer. Res.*, 5: 2121-2132; Ohta et al., 2001, *Oncology Reports*, 8: 1063-1066). During the transition from a growth-arrested to a proliferative state, transcription of mammalian Cdc6 is regulated by E2F proteins (Ohtani et al., 1998, *Oncogene*, 17: 1777-1785). For example, a significant downregulation of Cdc6 expression found in prostate cancer is attributed to E2F and October1 transcription factors (Robles et al., 2002, *J. Biol. Chem.*, 277(28): 25431-25438). Immunodepletion of Cdc6 by microinjection of anti-Cdc6 antibody blocks initiation of DNA replication in human tumors including tumors of neuroepithelial tissue, vestibular schwannomas, meningiomas and plurality adenomas, or human tumor cell lines (Ohta et al., 2001, *Oncology Reports*, 8: 1063-1066).

The additional regulatory event controlling initiation of DNA replication in mammalian cells is hypothesized to be dephosphorylation of CDC6 by PP2A, mediated by a specific interaction with PR48 or a related B" protein (Yan et al., 2000, *Mol. Cell Biol.*, 20(3): 1021-1029). The study demonstrates that an N-terminal segment of CDC6 binds specifically to PR48, a regulatory subunit of protein phosphatase 2A (PP2A).

4. SUMMARY OF THE INVENTION

Controlling the levels of apraxatin, tau, SLP, HMG17, PinX1, CIR, Cullin 3, HMGN3, HSPC144 and CDC6 is important in maintaining proper health and improper control of these levels is cause for disease. Applicants have discovered that these proteins are targets for degradation via the N-end rule ubiquitylation pathway. Controlling the rate of this degradation pathway provides an important mechanism for modulating the levels of these proteins and, thus, controlling disease states that are affected by the levels of these proteins.

One embodiment of the invention is a complex comprising at least one ubiquitin, or a derivative thereof, and a protein, wherein said protein is selected from the group consisting of apraxatin, tau, SLP, HMG17, PinX1, CIR, Cullin 3, HMGN3, HSPC144 and CDC6 and fragments and derivatives thereof. The complex is formed via the N-end rule ubiquitylation. Preferably, the complex is present in vitro and/or has been prepared via an in vitro ubiquitylation reaction. Preferably the complex is enriched or isolated relative to the conditions in which it is found in vivo. More preferably, the complex has a specific activity that is at least five-fold greater than the specific activity of an unenriched complex in solubilized cell lysates, cells or tissues. The complex may be immobilized on a solid support and/or linked to a label.

The invention also includes methods for producing these complexes, the methods comprising forming a mixture comprising i) a vector containing an insert coding for a protein selected from the group consisting of apraxatin, tau, SLP, HMG17, PinX1, CIR, Cullin 3, HMGN3, HSPC144 and CDC6; ii) an in vitro translation system and iii) an N-end rule ubiquitylation system and incubating the mixture to allow formation of the complex. Preferably, the in vitro translation system is also capable of carrying out in vitro transcription. Especially preferred in vitro translation systems comprise eucaryotic cell lysate, more preferably reticulocyte lysate, most preferably rabbit reticulocyte lysate. The lysates may be supplemented with, e.g., RNA polymerases to catalyze transcription and substrates and/or regulators of the transcription/translation reactions such as amino acids, tRNAs, ATP, etc. Preferably, the mixture includes a proteosome inhibitor. The method may further comprise the step of isolating the complex, preferably by binding the complex to an antibody specific for the protein or an antibody specific for poly-ubiquitin chains. Most preferably, the production of the complex is inhibited by the addition of an inhibitor of the N-end rule pathway.

The invention also includes an isolated activated fragment of a protein having an exposed N-degron, wherein said protein is selected from the group consisting of apraxatin, tau, SLP, HMG17, PinX1, CIR, Cullin 3, HMGN3, HSPC144 and CDC6, fragments and derivatives thereof. Preferably, the activated fragment is present in vitro and/or has been prepared via an in vitro reaction. Preferably the activated fragment is enriched or isolated relative to the conditions in which it is found in vivo. Most preferably, the activated fragment has an activity as a substrate for N-end rule ubiquitinylation, e.g., as measured in a ubiquitylation assay, that is at least five-fold greater than the activity of an equivalent concentration of the corresponding whole protein. The activated fragment may be immobilized on a solid support and/or linked to a label.

The invention also includes a method of producing these activated fragments, the method comprising forming a mixture comprising i) a, preferably isolated and/or enriched, protein selected from the group consisting of apraxatin, tau, SLP, HMG17, PinX1, CIR, Cullin 3, HMGN3, HSPC144 and CDC6; and ii) one or more enzymes (preferably, a protease) that modify said protein to form an N-degron; and incubating the mixture to allow production of the activated fragment. Optionally, the protein is prepared by in vitro translation or transcription/translation. In one exemplary embodiment, the method comprises forming a mixture comprising i) a vector containing a clone coding for a protein selected from the group consisting of apraxatin, tau, SLP, HMG17, PinX1, CIR, Cullin 3, HMGN3, HSPC144 and CDC6; ii) an in vitro translation system that comprises or is supplemented with one or more enzymes that modify the protein to expose an N-degron and incubating the mixture to form the activated fragment. Preferably, the in vitro translation system is also capable of carrying out in vitro transcription. Especially preferred in vitro translation systems comprise eucaryotic cell lysate, more preferably reticulocyte lysate, most preferably rabbit reticulocyte lysate. The lysates may be supplemented with, e.g., RNA polymerases to catalyze transcription and substrates and/or regulators of the transcription/translation reactions such as amino acids, tRNAs, ATP, etc. Preferably, the mixture includes an inhibitor of N-end rule ubiquitylation and/or a protease inhibitor. The method may further comprise the step of isolating the activated fragment.

In an alternate embodiment, the activated fragment is formed by a method comprising forming a mixture comprising i) a complex comprising at least one ubiquitin or a derivative thereof, and a protein selected from the group consisting of apataxin, tau, SLP, HMG17, PinX1, CIR, Cullin 3, HMGN3, HSPC144 and CDC6 and fragments and derivatives thereof and ii) a deubiquitylation system and incubating the mixture to allow production of said activated fragment. Preferably, the complex is formed by in vitro translation (and, optionally, transcription) as described above. The method may further comprise the step of isolating the activated fragment.

The invention also includes an assay composition comprising at least one ubiquitin or a derivative thereof and a protein, wherein said protein is selected from the group consisting of apataxin, tau, SLP, HMG17, PinX1, CIR, Cullin 3, HMGN3, HSPC144 and CDC6 and fragments and derivatives thereof. Preferably, the ubiquitin and/or the protein is immobilized on a support and/or linked to a label. Most preferably one of the ubiquitin or the protein is immobilized on a support and the other is linked to a label.

The invention also includes a method for identifying peptides having an exposed N-degron which are formed by the action of a protease on a protein, preferably a protein selected from the group consisting of apataxin, tau, SLP, HMG1G17, PinX1, CIR, Cullin 3, HMGN3, HSPC144 and CDC6 and fragments and derivatives thereof. The method comprises i) forming a first mixture comprising the protein and a protease that cleaves the protein to form a peptide having an exposed N-degron, and incubating the mixture so as to allow the protease to cleave the peptide to expose the N-degron; ii) forming a second mixture comprising the protein, the protease, and an N-end rule ubiquitylation system, and incubating the mixture so as to allow the protease to cleave the peptide to expose the N-degron and the N-end rule ubiquitylation system to ubiquitylate the peptide and iii) comparing the peptides present in the first and second mixtures to identify the peptides (e.g., by binding assays for ubiquitylated materials, electrophoresis, chromatography, mass spectrometry and/or peptide sequencing) that are non-ubiquitylated in the first mixture and ubiquitylated in the second mixture. Optionally, the N-end rule ubiquitylation system is present in both mixtures but an inhibitor of the system is present in the first mixture to inhibit the system. Optionally, the protein is generated in situ by in vitro translation (and, optionally, transcription) as described above. Preferably, the translation system also comprises the N-end rule ubiquitylation machinery and/or the protease.

The invention also includes an alternative method for identifying peptides having an exposed N-degron which are formed by the action of a protease on a protein, preferably a protein selected from the group consisting of apataxin, tau, SLP, HMG17, PinX1, CIR, Cullin 3, HMGN3, HSPC144 and CDC6 and fragments and derivatives thereof. The method comprises i) forming a first mixture comprising the protein and a protease that cleaves the protein to form a peptide having an exposed N-degron, and incubating the mixture so as to allow the protease to cleave the peptide to expose the N-degron; ii) forming a second mixture comprising the protein, the protease, an N-end rule ubiquitylation system and a proteosome system, and incubating the mixture so as to allow the protease to cleave the peptide to expose the N-degron, the N-end rule ubiquitylation system to ubiquitylate the peptide and the proteosome system to degrade the peptide and iii) comparing the peptides present in the first and second mixtures to identify the peptides (e.g., by electrophoresis, chromatography, mass spectrometry and/or peptide sequencing) that are present in the first mixture and degraded in the second mixture. Optionally, the N-end rule ubiquitylation system and/or proteome systems are present in both mixtures but an inhibitor of one or both systems is present in the first mixture to inhibit ubiquitylation and/or degradation. Optionally, the protein is generated in situ by in vitro translation (and, optionally, transcription) as described above. Preferably, the translation system also comprises the protease, N-end rule ubiquitylation system and/or the proteosome system.

The invention also includes a method for identifying a protease cleavage site which exposes an N-degron in a protein, preferably a protein selected from the group consisting of apataxin, tau, SLP, HMG17, PinX1, CIR, Cullin 3, HMGN3, HSPC144 and CDC6 and fragments and derivatives thereof. The method comprises forming a mixture comprising the protein and a protease which cleaves the protein at said cleavage site, incubating the mixture to allow the protease to cleave at the cleavage site and analyzing the cleavage products to determine the location of the cleavage site. The protein is, preferably, labeled, most preferably with a radioisotope. The location of the cleavage site is, preferably, determined by electrophoretic analysis, chromatography, protein sequencing and/or mass spectrometry. Optionally, the protein is generated in situ by in vitro translation (and, optionally, transcription) as described above. Preferably, the mixture comprises an inhibitor of N-end rule ubiquitylation and/or a proteosome inhibitor, most preferably an E3 ligase inhibitor. The inclusion of the N-end rule inhibitor is particularly advantageous when one component of the mixture comprises N-end rule ubiquitylation machinery, e.g., if the protease is present in a complex biological sample such as a cell lysate that comprises N-end ubiquitylation machinery.

The invention also includes a method for identifying proteases which cleave a protein so as to expose an N-degron, the protein preferably selected from the group consisting of apataxin, tau, SLP, HMG17, PinX1, CIR, Cullin 3, HMGN3, HSPC144 and CDC6 and fragments and derivatives thereof. The method comprises i) forming a mixture comprising said protein and a putative protease and ii) incubating the mixture and iii) determining if the protein has been cleaved to form an activated fragment with an exposed N-degron. Preferably, the method further comprises repeating the method with one or more other putative proteases. Even more preferably, a library of putative proteases is screened using the steps of the method. The putative proteases are, optionally, generated by in vitro translation and/or transcription.

In one preferred embodiment, determining if the protein has been cleaved comprises assaying for a previously identified activated fragment. In another preferred embodiment, the determining if the protein has been cleaved comprises treating the products of the incubation with an N-end rule ubiquitinylation system and/or a proteome system and identifying proteolytic products that are ubiquitinylated by the ubiquitinylation system and/or degraded by the proteosome system (see, e.g., the methods for identifying for identifying peptides having an exposed N-degron above).

The invention also includes a method for identifying E3 ligases comprising combining a putative E3 with an N-end rule substrate; and measuring the binding of the putative E3 to said N-end rule substrate. In one embodiment, the steps of the method are repeated with one or more additional putative E3 ligases to screen a library of putative E3 ligases. Optionally, the putative E3 ligase(s) are produced by in vitro translation and/or transcription. Preferably, the N-end rule substrate is a protein selected from the group consisting of apataxin, tau, SLP, HMG17, PinX1, CIR, Cullin 3, HMGN3, HSPC144 and CDC6 and fragments and derivatives thereof. More preferably, the N-end rule is an activated fragment of a protein selected from the croup consisting of aprataxin, tau, SLP, HMG17, PinX1, CIR, Cullin 3, HMGN3, HSPC144 and CDC6 having an exposed N-degron.

The invention also includes a method for identifying E3 ligases comprising combining a putative E3 with an N-end rule substrate and active ubiqutylation system, preferably in the presence of a proteosome inhibitor and measuring ubiquitylation and/or Ub-dependent degradation of said N-end rule substrate. Optionally, the putative E3 ligase(s) are produced by in vitro translation and/or transcription. Preferably, the activity of endogenous E3 ligases in said ubiquitylation system is at least two fold less than the activity of the E3 activity of a putative E3 ligase; more preferably, the ubiquitylation system lacks an active endogenous E3 ligase or is supplemented with inhibitors of the endogenous E3 activity. Preferably, the N-end rule substrate is a protein selected from the group consisting of aprataxin, tau, SLP, HMG17, PinX1, CIR, Cullin 3, HMGN3, HSPC144 and CDC6 and fragments and derivatives thereof. More preferably, the N-end rule is an activated fragment of a protein selected from the group consisting of aprataxin, tau, SLP, HMG17, PinX1, CIR, Cullin 3, HMGN3, HSPC144 and CDC6 and fragments and derivatives thereof having an exposed N-degron.

The invention also includes a method for identifying one or more active compounds that modulate (promote or inhibit) N-end rule dependent ubiquitylation of a N-end rule substrate, preferably a protein selected from the group consisting of aprataxin, tau, SLP, HMG17, PinX1, CIR, Cullin 3, HMGN3, HSPC144 and CDC6 and fragments and derivatives thereof. The method comprises i) forming a mixture comprising the substrate, an N-rule ubiquitylation system and one or more candidate compounds (e.g., compounds selected from a natural product library, a synthetic compound library, a combinatorial compound library and/or a library of FDA approved drugs, etc.); ii) measuring the ubiquitylation and/or degradation of said substrate; and iii) identifying active compounds that modulate the N-end rule dependent ubiquitylation of the N-end rule substrate. Preferably, the active compounds modulate E1 activity, E2 activity, E3 activity and/or the activity of a protease that exposes an N-degron. In one embodiment, said substrate is an activated fragment of the protein that comprises an exposed N-degron. In an alternative embodiment, the substrate includes a hidden N-degron and the mixture of step a) further includes a protease which exposes the N-degron. In another embodiment, the method is conducted with a substrate having a hidden N-degron and repeated with the corresponding substrate having an exposed N-degron to determine if an active compound inhibits ubiquitylation or a protease that exposes the N-degron. In yet another embodiment, the method is repeated in the presence of inhibitors of Type I, Type II and/or Type III N-end rule ubiquitylation to determine if an active compound is specific for one of those activities.

The invention also includes a method of making a pharmaceutical formulation containing one or more active compounds which modulate an N-end rule ubiquitylation, preferably of a protein selected from the group consisting of aprataxin, tau, SLP, HMG17, PinX1, CIR, Cullin 3, HMGN3, HSPC144 and CDC6. The method comprises the steps of identifying the one or more active compounds as described above and incorporating the one or more compounds into a pharmaceutical formulation comprising the at least one active compounds and a suitable carrier.

The invention also includes a method for modulating N-end rule ubiqutilation of a protein, preferably of a protein selected from the group consisting of aprataxin, tau, SLP, HMG17, PinX1, CIR, Cullin 3, HMGN3, HSPC144 and CDC6, comprising administering one or more of an active compounds that modulates the N-end rule ubiquitylation. Preferably, the active compound is selected as described above.

The invention also includes a method for modulating the in vivo level of a protein, preferably of a protein selected from the group consisting of aprataxin, tau, SLP, HMG17, PinX1, CIR, Cullin 3, HMGN3, HSPC144 and CDC6, comprising administering one or more active compounds that modulates the N-end rule ubiquitylation. Preferably, the active compound is selected as described above.

The invention also includes a method for modulating the in vitro or ex vivo level of a protein, preferably of a protein selected from the group consisting of aprataxin, tau, SLP, HMG17, PinX1, CIR, Cullin 3, HMGN3, HSPC144 and CDC6, comprising administering one or more of an active compounds that modulates the N-end rule ubiquitylation. Preferably, the active compound is selected as described above.

The invention also includes a method for treating a disease comprising administering one or more of an active compounds that modulates the N-end rule ubiquitylation of a protein, preferably of a protein selected from the group consisting of aprataxin, tau, SLP, HMG17, PinX1, CIR, Cullin 3, HMGN3, HSPC144 and CDC6. Preferably, the active compound is selected as described above.

The invention also includes a method of changing the susceptibility of a protein to N-end rule ubiquitylation by modifying the protein (e.g., by mutating the gene encoding the protein). The method may comprise i) modifying a protein having a protease cleavage site whose cleavage exposes an N-degron so as to form a modified protein that does not comprise the cleavage site (e.g. by modifying the amino acid sequence so it is no longer recognized by a protease which cleaves the unmodified protein at the cleavage site); ii) modifying a protein to introduce a protease cleavage site for a known protease, the cleavage of which exposes an N-degron, so as to form a modified protein that is cleaved by the protease to expose an N-degron; or iii) modifying a protein to alter an exposed N-degron or a hidden N-degron so as to form a modified protein that is not recognized by an N-end rule E3 ligase (in the case of hidden N-degrons, this method includes changing the identity of internal amino acids which are recognized in the unaltered protein by the E3 ligase after proteolytic processing of the protein). The modified protein may be expressed in a cell. Preferably, the cell does not express the wild type protein or the gene for the wild type protein is replaced with the gene for the modified protein. By introducing the modified protein, the level of the protein in the cell is modulated relative to the level of the protein in an analogous cell expressing the wild type protein.

The invention also includes a method of modulating the abundance of an N-end rule substrate in a cell by i) mutating the substrate to remove a protease cleavage site that is cleaved to introduce an N-degron; ii) mutating the substrate to introduce a protease cleavage site for a known protease, the cleavage of which exposes an N-degron, or iii) mutating the substrate to alter an N-degron so that it is not recognized by an E3 recognition after protease cleavage. Preferably, the substrate is a protein selected from the group consisting of aprataxin, tau, SLP, HMG17, PinX1, CIR, Cullin 3, HMGN3, HSPC144 and CDC6.

The invention also includes a method of generating a phenotypic cell line, or an animal, comprising the steps of i) generating a transfection vector, comprising a clone coding for a mutated form of a protein selected from the group consisting of aprataxin, tau, SLP, HMG17, PinX1, CIR, Cullin 3, HMGN3, HSPC144 and CDC6 and fragments and derivatives thereof, the mutated protein having a mutated protease cleavage site and/or N-degron and thereby modulating the susceptibility of the protein to the N-end rule ubiquitylation; ii) using said vector to transfect a cell line or generate a transgenic animal by homologous or non-homologous recombination, optionally via in vitro fertilization. The mutation is selected to modulate the rate at which the protein is cleaved by a, preferably endogenous, protease that exposes an N-degron and/or to modulate the rate of N-end rule ubiquitylation of a, preferably hidden, N-degron. The method, preferably, further comprises the step of detecting phenotypic changes in the cell line or animal relative to a control cell line or animal expressing the non-mutated form of the protein.

The invention also includes a kit for producing an N-end rule ubiquitylated protein, the protein selected from the group consisting of aprataxin, tau, SLP, HMG17, PinX1, CIR, Cullin 3, HMGN3, HSPC144 and CDC6 and fragments and derivatives thereof. The kit comprises, in one or more containers, one or more DNA sequences coding for the protein and one or more assay components selected from the group consisting of: (a) RRL; (b) plates; (c) one or more binding reagents; (d) a pH buffer; (e) one or more blocking reagents; (f) antibodies; (g) luminescent label; (h) luminescence co-reactant; (i) preservatives; (j) stabilizing agents; (k) enzymes; (l) detergents; (m) inhibitors and (n) desiccants.

The invention also includes a library of N-end rule ubiquitylation substrates. The library includes at least one, preferably a plurality, more preferably all, of the proteins in the group consisting of aprataxin, tau, SLP, HMG17, PinX1, CIR, Cullin 3, HMGN3, HSPC144 and CDC6 and fragments and derivatives thereof.

5. BRIEF DESCRIPTION OF THE DRAWINGS

FIG. 3 shows (A) the time course for an ECL assay for N-end rule ubiquitylation of tau; (B) the % inhibition of the ECL signal in the presence of N-end rule inhibitors; (C) gel electrophoretic analysis of the products of the ubiquitylation reactions; and (D) an overexposed image of the gel of FIG. 3(C).

FIG. 4 shows (A) the time course for an ECL assay for N-end rule ubiquitylation of aprataxin; (B) the % inhibition of the ECL signal in the presence of N-end rule inhibitors, and (C) gel electrophoretic analysis of the products of the ubiquitylation reactions.

FIG. 5 shows (A) the time course for an ECL assay for N-end rule ubiquitylation of synaptotagmin-like protein 2; (B) the % inhibition of the ECL signal in the presence of N-end rule inhibitors; and (C) gel electrophoretic analysis of the products of the ubiquitylation reactions.

6. DETAILED DESCRIPTION

Figures 1A, 1B, 1C:
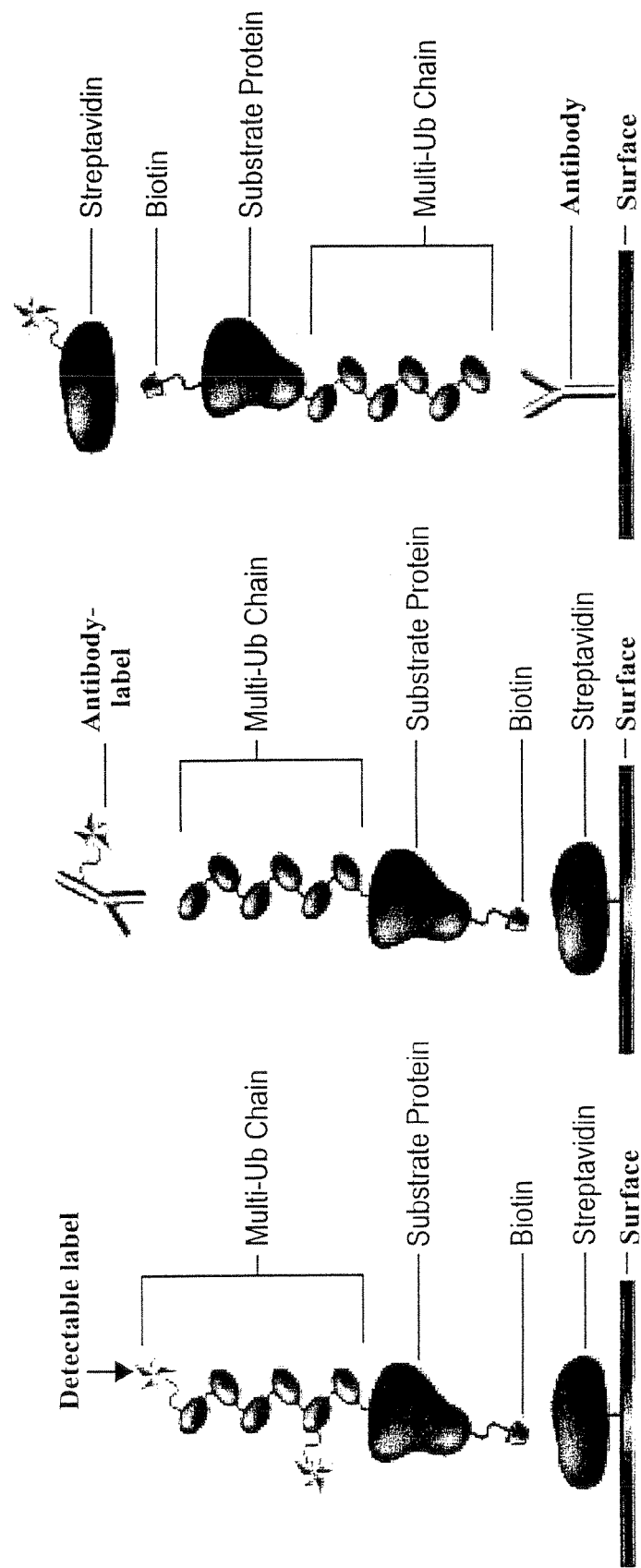
FIG. 1 shows a schematic representation of three binding assay formats used to measure ubiquitylation of a protein.

The invention relates to methods for identifying biologically significant proteins, protein interactions, interaction loci and pathways. The terms "protein", "polypeptide" and "peptide" are used interchangeably herein. The invention also relates to the proteins identified by these methods and variants thereof. The invention also relates to products of interactions of these proteins (or variants thereof) with other components of a biological pathway. The invention also relates to methods of identifying biologically active substances that modulate the activity of these proteins and the use of these in pharmaceutical compositions. The invention also relates to diagnostic methods that involve measuring these proteins or their associated biological activity. Furthermore the invention is related to reagents, kits and assay compositions, which assist in carrying out the methods of the instant invention.

Applicants have identified novel substrates of N-end rule ubiquitylation. These substrates include MAPT (tau) (e.g., SEQ ID NO: 1 encoded by polynucleotide sequence SEQ ID NO: 13 or the protein encoded by IMAGE clone #4448167), aprataxin (e.g., SEQ ID NO: 2 encoded by polynucleotide sequence SEQ ID NO: 14 or the protein encoded by IMAGE clone #3994375), synaptotagmin-like protein 2 (SLP2) (e.g., SEQ ID NO: 3 encoded by polynucleotide sequence SEQ ID NO: 15 or the protein encoded by IMAGE clone #3887570), HMG17 (HMGN2) (e.g., SEQ ID NO: 4 encoded by polynucleotide sequence SEQ ID NO: 16 or the protein encoded by IMAGE clone #s 3447081 or 3455121), CDC6 cell cycle controller protein (CDC6) (e.g., SEQ ID NO: 6 encoded by polynucleotide sequence SEQ ID NO 18 or the protein encoded by IMAGE clone #3867414), cullin 3 (e.g., SEQ ID NO: 7 encoded by polynucleotide sequence SEQ ID NO: 19 or the protein encoded by IMAGE clone 44426807), HMGN3 (e SEQ ID NO: 8 encoded by polynucleotide sequence SEQ ID NO: 20 or SEQ ID NO: 9 encoded by polynucleotide sequence SEQ ID NO: 21 or the protein encoded by IMAGE clone #s 3890883 or 4749335), CIR (e.g., SEQ ID NO: 10 encoded by polynucleotide sequence SEQ ID NO: 22 or the protein encoded by IMAGE clone #3910222), HSPC144 (e.g., SEQ ID NO: 11 encoded by polynucleotide sequence SEQ ID NO: 23 or the protein encoded by IMAGE clone #3907737) and PIN2-interacting protein I (PinX1) (e.g., SEQ ID NO: 12 encoded by polynucleotide sequence SEQ ID NO: 24 or the protein encoded by IMAGE clone #3911679) (Table 1). The definition of an N-end rule ubiquitylation substrate includes: (i) proteins which are ubiquitylated via N-end rule pathway, (ii) proteins which can be modified to form a fragment having an exposed N-degron, for example, by cleaving an N-terminal portion of a protein and (iii) a fragment of a protein having an exposed N-degron.

TABLE 1

| | Protein | Seq IDs for Protein | Seq IDs for Gene | Image Clone # |
|---|---|---|---|---|
| 1 | Microtubule Associated Protein Tau (MAPT, tau) | 1 | 13 | 4448167 |
| 2 | Aprataxin | 2 | 14 | 3994375 |
| 3 | Synaptotagmin-like protein 2 (SLP2) | 3 | 15 | 3887570 |
| 4 | HMG17 (HMGN2) | 4 | 16 | 3447081 or 3455121 |
| 5 | CDC6 Cell Cycle Control | 6 | 18 | 3867414 |
| 6 | Cullin 3 | 7 | 19 | 4426807 |
| 7 | HMGN3 | 8, 9 | 20, 21 | 3890883 or 4749335 |
| 8 | CBF1 Interacting Protein | 10 | 22 | 3910222 |
| 9 | HSPC144 | 11 | 23 | 3907737 |
| 10 | PIN2-interacting protein 1 | 12 | 24 | 3911679 |

As is well known, genes may exist in single or multiple copies within the genome of an individual. Such duplicate genes may be identical or may have certain modifications, including splice variants, nucleotide substitutions, additions or deletions, which all still code for polypeptides having substantially the same activity. The term "sequence encoding an N-end substrate protein" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a polypeptide with the same biological activity.

The present invention preferably relates to an isolated protein selected from a group listed in Table 1 and/or a protein selected from a group listed in Table 1 produced in vitro. The term "isolated" as used herein refers to material that is removed from its natural environment. For example, recombinant proteins produced in vitro, preferably in an in vitro protein expression system; recombinant proteins expressed in genetically modified cells; and/or proteins extracted and/or enriched from natural sources. The term isolated as used herein also includes purified material, for example, material that is substantially free of additional cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" as used herein also includes polypeptides purified by means available to a skilled artisan (for example, by means of chromatography, centrifugation, continuous flow separation, filtration and/or electrophoresis). The term "isolated" as used herein also refers to molecules enriched in their environment by means of stimulation or overexpression in native or non-native in vitro expression systems, cell extracts, cell lines and/or tissues, preferably enriched relative to other proteins in the environment by at least 2-fold, more preferably enriched by at least 5-fold, more preferably enriched by at least 10-fold.

One aspect of proteins listed in Table 1 is their ability to act as substrates for N-end rule ubiquitylation. The activity of these proteins as ubiquitylation substrates can be determined by measuring the accumulation of ubiquitinated products, for example, by the ability of the products to bind antibodies directed against ubiquitin.

Therefore the present invention relates, in part, to a protein selected from a group listed in Table 1, wherein the specific activity of the protein in a test solution relative to the specific activity of the same protein in an unenriched test solution from a natural source (such as solubilized cell lysates, cells or tissues) is greater preferably by at least five-fold, more preferably by at least 10-fold, more preferably by at least 100-fold, most preferably by at least 1000-fold. The term "specific activity" as used herein is a ratio of the activity to the total protein concentration in a sample and can be presented in terms of concentration or, alternatively, in the case of reactive species such as enzymes or enzymatic substrates in terms of signal in a functional assay such as an enzymatic assay. The present invention also relates to a protein selected from a group listed in Table 1, wherein the concentration of a protein in a solution provided is greater than the concentration of the same protein in an unenriched test solution from a natural source (such as solubilized cell lysates, cells or tissues) by at least 2-fold, preferably by at least five-fold, more preferably by at least 10-fold, more preferably by at least 100-fold, most preferably by at least 1000-fold. In one specific embodiment of the invention, the concentration of a protein selected from a group listed in Table 1 in a test solution is greater than 2%, preferably greater than 5%, more preferably greater than 10%, more preferably greater than 25%, more preferably greater than 50%, more preferably greater than 75%, more preferably greater than 90%, more preferably greater than 95%, most preferably greater than 98% of the total protein in a test solution.

The term "activated fragment" refers herein to a fragment of a protein, the fragment having an exposed N-degron that is hidden in the whole protein. The present invention also relates to an activated fragment of an N-end rule ubiquitylation substrate and/or variants thereof preferably an isolated activated fragment of an N-end rule ubiquitylation substrate and/or variants thereof, having exposed N-degron, wherein the N-end rule ubiquitylation substrate is selected from the group listed in Table 1. Preferably, the fragment of the present invention is a C-terminal fragment of protein which is the result of a specific proteolytic cleavage at a site which exposes a destabilized N-terminal residue, preferably a destabilizing Ile, Glu, His, Tyr, Gln, Asp, Asn, Phe, Leu, Trp, Lys, Arg, Ala, Ser, Thr or Cys, more preferably a destabilizing Glu, Gln, Cys, Arg, Lys, His specific to Type I N-end rule substrate, Leu, Ile, Tyr, Phe, Trp specific for Type II substrate and Ala, Ser and Thr specific for Type III substrate. The activated fragment may be subjected to an additional proteolysis from the C-terminus either preceding or following a cleavage event which exposes an N-degron.

Activated fragments of aprataxin include a ~20-21.5 kDa C-terminal fragment of the protein with an exposed destabilized N-terminal residue, preferably a destabilizing Ile, Glu, His, Tyr, Gin, Asp, Asn, Phe, Leu Trp, Lys, Arg, Ala, Ser, Thr or Cys, more preferably a destabilizing Type I residue selected from Glu, Gin, Cys, Arg, Lys, and His. Preferably, the fragment is the product of a specific proteolytic cleavage at a site between residues 150-160 of aprataxin which also forms a ~16.5-18 kDa N-terminal fragment.

Activated fragments of synaptotagmin-like protein 2 include a C-terminal fragment of the protein with an exposed destabilized N-terminal residue, preferably a destabilizing Ile, Glu, His, Tyr, Gin, Asp, Asn, Phe, Leu Trp, Lys, Arg, Ala, Ser, Thr or Cys, more preferably a destabilizing Type II residue selected from Leu, Ile, Tyr, Phe, and Trp. Preferably, the fragment is the product of a specific proteolytic cleavage at a site between residues 1-50 which also forms a ~0.5-5 kDa N-terminal fragment.

Activated fragments of MAPT (tau) include a ~15-20 kDa fragment of the protein with an exposed destabilized N-terminal residue, preferably a destabilizing Ile, Glu, His, Tyr, Gin, Asp, Asn, Phe, Leu Trp, Lys, Arg, Ala, Ser, Thr or Cys, more preferably a destabilizing Type I residue selected from Glu, Gin, Cys, Arg, Lys, and His. The fragment is the product of multi-site proteolytic cleavages.

Activated fragments of cdc6 include two protein fragments starting with exposed destabilized N-terminal residues, preferably destabilizing Ile, Glu, His, Tyr, Gin, Asp, Asn, Phe, Leu Trp, Lys, Arg, Ala, Ser, Thr or Cys, more preferably destabilizing Type I residues selected from Glu, Gin, Cys, Arg, Lys, and His. The fragments are the product of multi-site proteolytic cleavages. One of the activated fragments is a peptide with a molecular weight of ~40-45 kDa.

A person of ordinary skill in the art will recognize that the present invention relates not only to the specific protein sequences disclosed in the specification, but also to protein variants thereof such as fragments, analogs and/or derivatives. A protein variant of a specific protein sequence preferably retains at least one biological function or activity of the specific protein sequence, for example the ability to be ubiquitylated via the N-end rule pathway or the ability to act as a substrate for a protease that exposes an N-degron, etc.

The variants of the polypeptides according to the present invention may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) one in which the polypeptide is an alternative splice variant of the polypeptide of the present invention, (iv) fragments of the polypeptides and/or (iv) one in which the polypeptide is fused with another polypeptide, such as a leader or secretory sequence or a sequence which is employed for purification (for example, His-tag) or visualization (for example GFP). The fragments include polypeptides generated via proteolytic cleavage (including multi-site proteolysis) of an original sequence. Variants may be post-translationally, or chemically modified. Such variants are deemed to be within the scope of those skilled in the art from the teaching herein.

As known in the art "similarity" between two polypeptides is determined by comparing the amino acid sequence and its conserved amino acid substitutes of one polypeptide to a sequence of a second polypeptide. Variants are defined to include polypeptide sequences different from the original sequence, preferably different from the original sequence in less than 40% of residues per segment of interest, more preferably different from the original sequence in less than 25% of residues per segment of interest, more preferably different by less than 10% of residues per segment of interest, most preferably different from the original protein sequence in just a few residues per segment of interest and at the same time sufficiently homologous to the original sequence to preserve the functionality of the original sequence and/or the ability to ubiquitylate via N-end rule pathway. The present invention includes protein sequences that are at least 60%, 65%, 70%, 72%, 74%, 76%, 78%, 80%, 90%, or 95% similar or identical to an amino acid sequence selected from a group listed in Table 1. Still within the scope of the invention are preferred segments of interest of the sequences of the present invention which are comprised of at least 10, 25, 50, 100, 150 or 200 amino acid residues.

The proteins of the invention can be post-translationally modified. For example, post-translational modifications that fall within the scope of the present invention have been observed in rabbit reticulocyte lysate or wheat germ extract include signal peptide cleavage, glycosylation, acetylation, isoprenylation, proteolysis myristoylation, protein folding and proteolytic processing (Glass and Pollard, 1990, Promega Notes 26). Some modifications or processing events require introduction of additional biological machinery. For example, processing events, such as signal peptide cleavage and core glycosylation, are examined by adding canine microsomal membranes (Walter and Blobel, 1983, *Meth. Enzymol*, 96: 84) or Xenopus egg extracts (Zhou, et al. U.S. Pat. No. 6,103,489) to a standard translation reaction.

The proteins of the invention may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR) (Noren et al., 1989, *Science* 244:182-188). In SNAAR, a unique codon is required on the MnRNA and the suppressor tRNA, acting to target a non-native amino acid to a unique site during the protein synthesis (WO90/05785). However, the suppressor tRNA must not be recognizable by the aminoacyl TRNA synthetases present in the protein translation system (Bain et al., 1991, *Biochemistry* 30:5411-5421).

In certain cases, a non-native amino acid can be formed after the tRNA molecule is aminoacylated using chemical reactions which specifically modify the native amino acid and do not significantly alter the functional activity of the aminoacylated tRNA (Promega Technical Bulletin No. 182; tRN-$A^{nscend}$™: Non-radioactive Translation Detection System, September 1993). These reactions are referred to as post-aminoacylation modifications. For example, the epsilon-amino group of the lysine linked to its cognate tRNA (tR-$NA^{LYS}$), could be modified with an amine specific photoaffinity label (Krieg et al., 1986, *Proc. Natl. Acad. Sci. USA*, 83:8604-8608).

One embodiment of the present invention relates to a complex of an N-end rule substrate and at least one ubiquitin formed via N-end rule pathway, wherein a substrate protein is selected from proteins listed in Table 1 and/or variants thereof. Preferably this complex is isolated. For example the isolated complex may be produced in vitro, preferably in an in vitro protein expression system, in vivo by expressing recombinant proteins in genetically modified cells; by extracting and/or enriching from natural sources; and/or by chemical synthesis. More preferably the complex has a specific activity or concentration enrichment of at least two-fold greater than the specific activity and/or concentration of an unenriched complex in a natural source such as solubilized cell lysate, cell or tissue, more preferably of at least 5-fold, most preferably of at least 10-fold.

Another preferred embodiment of the instant invention is an assay composition comprising an N-end rule substrate protein selected from proteins listed in Table 1 or an activated fragment thereof, and/or variants thereof and an ubiquitin. Furthermore, in one preferred embodiment of the present invention the complex, or protein, and/or variants thereof or ubiquitin constituents of the complex, or assay composition are immobilized on a support. Suitable supports include supports known in the art of solid phase binding assays and include surfaces of tubes, multi-well plates, particles (e.g., magnetizable particles), filters, porous membranes, electrodes, slides and chips. One especially preferred solid phase support is a carbon electrode surface, more preferably a surface of a carbon ink electrode, most preferably a surface of a plasma-treated patterned carbon ink electrode. Carbon electrodes are described in U.S. Pat. No. 6,207,369 and multi-well multi-array plates having integrated carbon electrodes are described in a U.S. patent application Ser. Nos. 10/185,274 and 10/185,363, each of which is incorporated herein by this reference.

Yet in another specific embodiment of the present invention the protein and/or variants thereof or ubiquitin constituents of the complex or assay composition are linked to a detectable label. Detectable labels utilized herein may comprise a radioisotope, a fluorescent (including fluorescence polarization), phosphorescent, luminescent, chemiluminescent and/or electrochemiluminescent compound, an enzyme, or an enzyme co-factor as a label moiety, including binding species recognized by preferably labeled binding partner (e.g biotin, streptavidin, epitope tags, affinity tags (e.g., $His_6$), fluorescein, hapten, immunogen, GST and/or GFP), preferably an ECL label. Examples of ECL technology, ECL labels, ECL assays and instrumentation for conducting ECL assays are described in U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369 and 5,589,136 and published PCT applications WO99/63347; WO00/03233; WO99/58962; WO99/32662; WO99/14599; WO98/12539; WO97/36931 and WO98/57154.

Advantageously, the immobilized or labeled proteins of the invention may be used in binding assays, preferably immunoassays, for measuring the proteins themselves or for measuring the extent of modification of these proteins, e.g., the extent of ubiquitylation, proteolytic cleavage or degradation, see, e.g., the assay techniques described in U.S. patent application Ser. No. 10/238,960, entitled "Methods, Reagents, Kits and Apparatus for Protein Function", hereby incorporated by reference.

The invention provides advantageous formats for production, accumulation and measurement of ubiquitylated target proteins, preferably proteins ubiquitylated via the N-end rule pathway, more preferably proteins selected from the group listed in Table 1 and variants thereof. Another preferred embodiment of the present invention is the method to produce and isolate an activated fragment of an N-rule ubiquitylation substrate having exposed N-degron and/or variants thereof.

According to one embodiment of the present invention the molecules are produced by forming a mixture of a target protein (or a protein synthesis system that produces, in situ, the target molecule) and an ubiquitylation system, preferably an N-end rule ubiquitylation system. The systems preferably produce target molecules in vitro, preferably in an in vitro protein expression system, preferably a eukaryotic cell lysate (such as a reticulocyte lysate, most preferably a rabbit reticulocyte lysate). These lysates may be supplemented with, e.g., RNA polymerases to catalyze transcription and substrates and/or regulators of the transcription/translation reactions such as amino acids, tRNAs, ATP, etc. A suitable in vitro transcription/translation system based on rabbit reticulocyte lysate is commercially available from Promega. The cell lysate not only provides the machinery for protein synthesis but also provides the enzymes necessary for ubiquitylation and the proteases necessary to expose N-degrons for an N-end rule ubiquitylation. In alternative embodiments, the target proteins are produced in vivo by expressing recombinant proteins in genetically modified cells; by extracting and/or enriching from natural sources; and/or by chemical synthesis.

In one preferred embodiment the method involves inserting a clone into an expression vector, preferably a clone selected from the group of polynucleotide molecules encoding proteins listed in Table 1, activated fragments having exposed N-degron, or variants thereof. A plurality of suitable expression vectors are well known to a person of ordinary skill in the art.

The method further comprises culturing the expression vectors in (i) an in vitro protein expression system, preferably cell lysate, most preferably in reticulocyte lysate, or (ii) in transformed host-cells or cell-free systems under conditions such that the encoded sequence is expressed and the protein is produced, preferably in the transformed host-cells containing all components necessary to support ubiquitylation, preferably N-end rule ubiquitylation, preferably further containing one or more proteasome inhibitors. Yet in another specific embodiment of the invention, the protein expression system is supplemented with additional enzymes of the ubiquitylation system, preferably E3 ligases, most preferably an UBR1 E3 ligase.

In one embodiment of the invention, in order to produce an activated fragment of a protein, preferably a protein listed in Table 1, and/or variant thereof having exposed N-degron, the system is further supplemented with one or more inhibitors of ubiquitinylation, preferably E3 ligase inhibitors.

Yet in another preferred embodiment of the present invention proteins ubiquitylated via N-end rule pathway are treated with deubiquitylating, enzymes, preferably UBC enzymes, simultaneously and/or at a later time to produce activated fragments having exposed N-degron. The method includes forming a mixture comprising either ubiquitylated protein, or a vector encoding an N-end rule ubiquitylation substrate, a system containing all components necessary to support an expression of an encoded polypeptide and a proteolytic cleavage necessary to expose N-degron and one or more deubiquitylating enzymes sufficient to remove polyubiquitin chains from an activated fragment of an N-end rule substrate protein, fragment, analog or derivative thereof and incubating it for a time sufficient to produce a desired product.

Yet in another preferred embodiment the protein or variant thereof, ubiquitylated via N-end rule pathway, is produced alone or as a fusion product, preferably a fusion product which incorporates a tag or a marker, preferably an affinity purification tag, most preferably a biotinylated Lys into polypeptides. The coding sequence can be cloned in frame with the sequence encoding a tag, preferably a His-tag, GST-fusion or GFP-fusion or an expression system can be supplemented with biotinylated Lys-tRNA. In one specific embodiment of the invention, the portion fused to an N-end rule ubiquitylation substrate can be cleaved by proteolytic enzymes available to skilled artisan.

The proteins ubiquitylated via N-end rule pathway and/or their activated fragment are further isolated by one or more of the isolation protocols, such as chromatography, centrifugation, continuous flow separation, filtration and/or electrophoresis. The preferred protocols include affinity chromatography using affinity tags incorporated into polypeptides and/or antibodies specific for polyubiquitin chains, streptavidin binding to a product having biotinylated lysines or antibodies specific for N-end rule substrates or their activated fragments.

Measurement of the degree of modification of the protein can be achieved in a binding assay format, preferably an ubiquitin specific format, available to a skilled artisan.

Examples of techniques that can be used for detecting or measuring the degree of protein modification include mass spectrometry, chromatography, electrophoresis, agglutination, western blot, specific binding assays, immunoassay, immunofluorescence and immunochromatographic assays detected via surface plasmon resonance, radioactivity measurement, fluorescence, fluorescence polarization, phosphorescence, luminescence, chemiluminescence and electrochemiluminescence (ECL). The preferred method of the present invention is the specific binding assay with electrochemiluminescence detection system, preferably using the SectorHTS Reader and Multi-Spot Multi-Array plates (MSD).

The immunoassay or specific binding assay according to the preferred embodiments of the invention can involve a number of formats available in the art. The antibodies and/or specific binding partners can be labeled with a detectable label or immobilized on a surface. The term "antibody" includes intact antibody molecules (including hybrid antibodies assembled by in vitro re-association of antibody subunits), antibody fragments and recombinant protein constructs comprising an antigen binding domain of an antibody (as described, e.g., in Porter and Weir, 1966, *J. Cell Physiol.*, 67 (Suppl 1); 51-64 and Hochman, Inbar and Givol, 1973, *Biochemistry* 12: 1130; hereby incorporated by reference). The term also includes intact antibody molecules, antibody fragments and antibody constructs that have been genetically altered or chemically modified, e.g., by the introduction of a label.

Preferably, the detection is performed by contacting an assay composition with one or more detection molecules capable of specifically binding with the marker(s) of interest. More preferably, the assay uses a sandwich or competitive binding assays format. Examples of sandwich immunoassays performed on test strips are described by U.S. Pat. No. 4,168,146 to Grubb et al. and U.S. Pat. No. 4,366,241 to Tom et al. Examples of competitive immunoassay devices suitable for use with the present invention include those disclosed by U.S. Pat. No. 4,235,601 to Deutsch et al., U.S. Pat. No. 4,442,204 to Liotta, and U.S. Pat. No. 5,208,535 to Buechler et al. Most preferably, at least one of the binding reagents employed in such an assay is immobilized on a solid phase support, preferably on a surface of a tubes, multi-well plate, particle (e.g. magnetizable particles), filter, porous membrane, electrode, slide and/or chip.

Examples of suitable experimental designs to measure ubiquitylation of a given protein and/or variant thereof schematically are depicted in FIG. 1.

In one preferred embodiment of the invention depicted in FIG. 1(A), a labeled ubiquitin, preferably labeled with a detectable label, more preferably labeled with a radioactivity, fluorescence, fluorescence polarization, phosphorescence, luminescence, chemiluminescence or electrochemiluminescence label, more preferably labeled with ECL label, most preferably MSD TAG™, is combined with the protein, a ubiquitylation system and, optionally, additional unlabeled ubiquitin so that the labeled ubiquitin is incorporated into poly-Ub chains linked to the protein. The ubiquitylated products are captured on a surface, preferably on a surface of a tube, multi-well plate, particle (e.g. magnetizable particle), filter, porous membrane, electrode, slide and/or chip, most preferably a surface of a SectorHTS plate, via binding interaction of a labeled protein and a binding partner immobilized on a surface. The extent of ubiquitylation is determined by measuring the amount of the ubiquitylated product, e.g., by measuring the amount of the detectable label on the surface. As shown, in the figure, the protein is labeled with a binding reagent (biotin) that binds to the immobilized binding partner (streptavidin, or alternatively avidin). Alternatively, the binding reagent is omitted and a binding partner (e.g., an antibody) is employed that binds directly to the protein of interest. In another alternative embodiment, the protein of interest is directly immobilized on the surface (e.g., by passive adsorption or through covalent bonds).

A variant of the embodiment depicted in FIG. 1 (A) and described above is shown in FIG. 1 (B). This embodiment differs in that the ubiquitylated product is detected using a labeled ubiquitin specific binding reagent (preferably an antibody), preferably labeled with a detectable label, more preferably labeled with a radioactivity, fluorescence, fluorescence polarization, phosphorescence, luminescence, chemiluminescence or electrocmemiluminescence label, more preferably labeled with ECL label, most preferably an MSD TAG™ labeled antibody. The ubiquitin specific binding reagent is, preferably, selective for poly-ubiquitin chains or ubiquitin-protein conjugates relative to free monomeric ubiquitin.

In yet another preferred embodiment of the invention depicted in FIG. 1 (C) a target protein, preferably labeled with a detectable label, is combined with ubiquitin and an ubiquitylation system so that the target protein is ubiquitylated. The ubiquitylated product is captured on a surface, preferably on a surface of or a multiwell plate or an electrode, most preferably on a surface of a Sector HTS™ plate, via an ubiquitin-specific binding reagent (preferably, an antibody). The ubiquitin specific binding reagent is, preferably, selective for poly-ubiquitin chains or ubiquitin-protein conjugates relative to free monomeric ubiquitin. The ubiquitylation product is detected using the detectable label as a reporter so as to measure the extent of ubiquitylation.

The target protein is labeled with a binding reagent (shown as biotin) that binds to a labeled binding partner (shown as streptavidin) having a second detectable label, preferably a radioactivity, fluorescence, fluorescence polarization, phosphorescence, luminescence, chemiluminescence or electrochemiluminescence label, more preferably an ECL label, most preferably MSD TAG™. The binding partner is combined with the ubiquitylation product and the second label is measured to determine the extent of ubiquitylation. In a variation of this embodiment, the target protein is unlabeled and the labeled binding partner (preferably, an antibody) is specific for the target protein. In another variation of the embodiment, the binding partner is omitted and the target protein is directly labeled with a radioactivity, fluorescence, fluorescence polarization, phosphorescence, luminescence, chemiluminescence or electrochemiluminescence label, more preferably labeled with ECL label, most preferably MSD TAG™.

According to a preferred embodiment of the invention the ubiquitylation assays are then repeated in the presence of inhibitors of the N-end rule pathway, preferably in the presence of Arg-β-Ala and/or Trp-Ala dipeptide inhibitors of the N-end rule pathway. Comparison of the extent of the ubiquitylation of a target protein in the presence or absence of the inhibitors allows for the classification of ubiquitylation substrates as N-end rule substrates or, more specifically, as Type I, Type II or Type III substrates.

The invention further provides for measuring the time course of a ubiquitylation reaction both in the presence and absence of dipeptide inhibitors, preferably by binding assay and/or by denaturing gel electrophoresis radiography detection system. The time course identifies Type I vs. II vs. III substrates and identifies substrates which undergo rapid or slow ubiquitylation. The bands on the denaturing gel electrophoresis radiograph for samples collected at different times during an ubiquitylation reaction allow the measurement of, e.g., (1) the time course of the production and degradation of a full length protein; (2) the time course of the accumulation of N-terminal fragments cleaved by specific proteases, the accumulation of which has no dependence on the presence or absence of dipeptide inhibitors; (3) the size of such N-terminal fragments; (4) the time course for the accumulation of C-terminal fragments having exposed N-degrons, the accumulation of which are dependent on the presence or absence of the N-end rule pathway inhibitors; (5) the size of such C-terminal fragments and (6) the time course for the accumulation of multi-site proteolysis products for some protein substrates.

One preferred embodiment of the invention is directed to identification of a protease cleavage site that is cleaved to form a fragment having a destabilizing N-terminal residue which is processed via the N-end rule pathway. A protease cleavage site is identified by (i) forming a mixture of an N-end rule ubiquitylation substrate and a protease necessary to activate a substrate, preferably the mixture contains one or more E3 ligase inhibitors and/or one or more proteasome inhibitors and (ii) identifying a protease cleavage site. In yet another embodiment, the mixture is enriched and/or treated with deubiquitylating enzymes prior to analysis. The method may also include repeating the experiment in the presence and absence of proteosome inhibitors. Comparison of the peptides formed under the two conditions allows for the identification of those fragments that possess an N-degron (i.e., the fragments that are only observed in the presence of the inhibitor).

The protease may be supplied, e.g., (i) in purified form; (ii) by in vitro protein expression system, preferably cell lysate, most preferably in reticulocyte lysate, or (iii) by transformed host-cells or cell-free systems under conditions such that the encoded sequence is expressed and the protein is produced.

According to one preferred embodiment the cleavage products are analyzed to determine the sizes of proteolytic fragments and thereby to determine the location of the cleavage site by techniques available to a skilled artisan. The examples of such techniques include but are not limited to gel electrophoresis using radiographic or calorimetric detection systems, chromatography (e.g. size exclusion chromatography), centrifugation, mass spectroscopy (preferably on fragment isolated and purified, preferably isolated and/or purified by chromatographic techniques, such as size exclusion, affinity or ion exchange chromatography) and/or filtration. These techniques may be further supplemented by peptide sequencing techniques, e.g., sequencing techniques based on chemical or enzymatic degradation or sequencing techniques based on mass spectrometric analysis. Preferably the location of the cleavage site is refined based on the knowledge of the destabilizing residues, sequence and fragment size information, preferably computationally.

Yet in another preferred embodiment labeled amino acids, preferably radiolabeled amino acids, are incorporated into N- and C-terminal fragments of the protein and the fragments are subjected to sequencing to identify a protease cleavage site.

Yet in another embodiment of the present invention, the protease cleavage site is identified via mutagenesis, preferably scanning mutagenesis. Mutations are introduced into protein sequence, preferably in a vicinity of a putative cleavage site, more preferably at the cleavage site, preferably a putative site identified by the above described techniques. Mutations that deactivate N-end rule ubiquitylation pathway identify the cleavage site.

One embodiment of the invention is a method for identifying proteases which expose a destabilizing N-terminal amino acid residue in a target protein (preferably, a protein selected from the list of proteins in Table 1). Proteases are identified by either (i) measuring a binding of a putative protease to an N-end rule substrate or an activated fragment thereof, preferably to an N-end rule substrate protein having a mutation at or in close proximity to a cleavage site which prevents proteolysis, more preferably to an N-end rule substrate having a transition-state analog in place of a cleavable bond, most preferably selected from proteins listed in Table 1, and/or variants thereof; or (ii) by measuring proteolytic cleavage of an N-end rule substrate, most preferably selected from proteins listed in Table 1, and/or variants thereof.

Therefore, one embodiment of the present invention involves screening putative proteases, preferably protease libraries, by (i) contacting a putative protease with an N-end rule substrate, preferably protein selected from a group listed in Table 1 and/or variant thereof and (ii) identifying proteases which bind to an N-end rule substrate. Another embodiment of the present invention involves screening putative proteases, preferably protease libraries, for proteases which bind to an activated fragment of an N-end rule substrate, preferably a protein selected from a group listed in Table 1 and/or variants thereof. The techniques available to a skilled artisan include, but are not limited to affinity chromatography, preferably an affinity chromatography resin having immobilized one or more N-end rule substrates, activated fragments and/or variants thereof, preferably where N-end rule substrates have a mutation at or in close proximity to a cleavage site which prevents proteolysis, more preferably an N-end rule substrate having a transition-state analog in place of a cleavable bond, most preferably selected from proteins listed in Table 1, and/or variants thereof.

Yet in another embodiment of the invention N-end rule substrates or activated fragments thereof, preferably to an N-end rule substrate protein having a mutation at or in close proximity to a cleavage site which prevents proteolysis, more preferably to an N-end rule substrate having a transition-state analog in place of a cleavable bond, most preferably selected from proteins listed in Table 1, and/or variants thereof are immobilized on supports known in the art of solid phase binding assays and include surfaces of tubes, multi-well plates, particles (e.g., magnetizable particles), filters, porous membranes, electrodes, slides and chips. One especially preferred solid phase support is a carbon electrode surface, more preferably a surface of a carbon ink electrode, most preferably a surface of a plasma-treated patterned carbon ink electrode. Putative proteases are linked to a detectable label, selected from a radioisotope, a fluorescent (including fluorescence polarization), phosphorescent, luminescent, chemiluminescent and/or electrochemiluminescent compound, an enzyme, or an enzyme co-factor as a label moiety, including binding species recognized by preferably labeled binding partner (e.g., biotin, streptavidin, epitope tags, His6, fluorescin, hapten, immunogen, GST and/or GFP), preferably an ECL label. Yet in another embodiment the binding is measured in the ELISA format available to a skilled artisan. Another suitable binding assay format is described in a European Patent Application EP 1182458A1.

Yet another embodiment of the present invention involves screening putative proteases, preferably protease libraries, for proteases which cleave an N-terminal fragment of an N-end rule substrate, preferably a protein selected from a group listed in Table 1 and/or variants thereof, preferably having blocked (or internal) N-degron, to expose destabilizing N-terminal residue. The proteases are identified in a protease activity assay that comprises combining the putative protease with the substrate and measuring the extent of cleavage of the substrate, e.g., by measuring the loss of substrate or production of cleavage products. The method may use, e.g., one of the many formats for measuring protease activity that are available to a skilled artisan.

In one specific embodiment, the present invention involves screening protease libraries for proteases which expose N-degron thereby activating N-end rule ubiquitylation. The method comprises combining a putative protease with a substrate having an internal N-degron and measuring the production of cleavage products having an exposed N-degron. Preferably, the assay further comprises contacting the products with an N-end rule ubiquitylation system and, optionally, a proteosome system and measuring the production of ubiquitylated or proteosome-degraded peptide fragments, e.g., by the detection techniques described above. The ubiquitylation and/or proteosome systems may be provided by a eukaryotic cell lysate, preferably a reticulocyte lysate, preferably a rabbit reticulocyte lysate. Optionally, the protein is prepared in such a lysate to provide a composition comprising the protein, ubiquitylation system and proteosome system. Proteosome inhibitors may be added to allow measurement of ubiquitylated fragments without interference from proteosome degradation of the fragments.

The invention further provides a method of identifying E3 ligases by screening libraries of proteins for proteins that promote the ubiquitylation of an ubiquitylation substrate. The ubiquitylation activity can be measured, e.g., by any of the techniques described above.

In one embodiment, the method comprises (i) contacting putative E3 ligases, preferably libraries of putative E3 ligases with N-end rule substrates (preferably, a protein listed in Table 1 or a fragment or variant thereof) and a ubiquitylation system and (ii) identifying E3 ligases, preferably E3 ligases with N-end rule activity. The activity measurement is done as described above, where the ubiquitylation of an N-end rule substrate protein and/or variant thereof, preferably a protein selected from a group listed in Table 1 and/or variants thereof, is detected. Preferably, the ubiquitylation system is deficient in E3 activity, e.g., activity of endogenous E3 ligases is detectably lower that the activity of a putative ligase, preferably by at least two-fold, more preferably by at least five-fold, more preferably by at least 10-fold. Most preferably the N-end rule degradation system lacks endogenous E3 ligases. In one embodiment, the activity of endogenous E3 ligases is inhibited by an inhibitor specific for the endogenous E3 ligase.

In one preferred embodiment, the E3 ligases are identified by their ability to bind N-end rule substrates, or activated fragments of N-end rule substrates (preferably, a protein listed in Table 1 or a fragment or variant thereof). The method comprises combining a putative E3 ligase with a substrate and measuring the formation of binding complexes comprising the substrate and the putative E3 ligase. The formation of the binding complex may be measured by binding assay methods known to one skilled in the art. In one example, the substrate is immobilized on a solid supports known in the art of solid phase binding assays and include surfaces of tubes, multiwell plates, particles (e.g., magnetizable particles), filters, porous membranes, electrodes, slides and chips, more preferably on a surface of a well in a multiwell plate, or on a chromatographic resin. One especially preferred solid phase support is a carbon electrode surface, more preferably a surface of a carbon ink electrode, most preferably a surface of a plasma-treated patterned carbon ink electrode.

In one specific embodiment of the invention, the retardation in the retention time of a putative E3 ligase by a chromatographic support having immobilized substrates of N-end rule ubiquitylation, or activated fragments thereof, preferably selected from a group of proteins listed in Table 1, identifies E3 ligases.

In yet another embodiment, the method further comprises contacting the ubiquitylation reaction products with a proteosome system and monitoring the degradation of the N-end substrate and/or variant thereof. For example in one specific embodiment of the invention a disappearance of a substrate labeled with a detectable label, preferably an ECL label is detected.

Another aspect of the invention relates to improved methods and systems for selecting or identifying active compounds, preferably biologically active compounds in vitro, ex vivo, in vivo and/or in silico, and, optionally, incorporating such compounds into suitable carrier compositions in appropriate dosages to form pharmaceutical compositions.

According to one embodiment of the present invention, active compounds are identified by screening one or more candidate compounds by a screening assay comprising (i) combining a candidate compound, an N-end rule substrate (preferably a protein listed in Table 1 or an activated fragment thereof, an N-end rule ubiquitylation system and, optionally, a protease that exposes a hidden N-degron in said substrate; (ii) measuring the production of ubiquitylated products and (iii) identifying compounds that modulate the rate of ubiquitylation. The method may further comprise comparing the measured production to that measured in the absence of the candidate compound to determine if the candidate compound modulates the rate of ubiquitylation.

Preferably, the method further comprises testing said one or more active compounds for bioavailability, toxicity and/or biological activity in vivo. Preferably, the method further comprises synthesizing analogues of said one or more active compounds and further screening analogues for activity, bioavailability, biological activity and/or toxicity.

In one embodiment, the active compounds are modulators, preferably inhibitors or promoters of the ubiquitin ligation, preferably inhibitors or promoters of the ubiquitin ligation to an exposed destabilizing N-terminal residue. Preferably the active compounds are inhibitors or promoters of E3 ligase, preferably Type I/II/III-specific N-end rule ubiqutylation inhibitors or promoters. Yet in another embodiment the active compounds identified according to the methods of this invention are inhibitors or promoters of E1 ligase or E2 ligase.

Yet in another embodiment the active compounds identified according to the methods of this invention are protease activity modulators, preferably inhibitors or promoters of a proteolytic cleavage necessary to expose N-degron.

Another preferred embodiment of the present invention is a method for determining whether the active compound is a specific modulator of a protease, or a ligase system. While the active compounds which modulate the activity of a ligase system will not inhibit or promote production and/or detection of activated fragments of substrate proteins having exposed N-degron, the modulators specific for a protease will inhibit or promote production and/or detection of activated fragments of substrate proteins. Therefore, according to one embodiment of the present invention, the method further comprises measuring the accumulation of non-ubiquitylated activated fragments to determine if the active compound is an inhibitor of protease activity or ubiquitylation activity. By way of example, these fragments will appear as bands in a gel electrophoresis analysis of the assay products if the ubiquitylation activity is diminished or absent but the bands will be greatly diminished or absent in the presence of ubiquitylation activity.

According to a particularly preferred embodiment, the method further comprises formulating the one or more compounds into drugs for administrating to humans and/or animals. To prepare a pharmaceutical formulation, a suitable carrier is added to one or more active compounds identified according to the method of the instant invention. A skilled artisan will find FDA approved additives in a National Formulary compiled by the U.S. Pharmacopeia, or may develop his own.

Preferably, the formulating comprises determining the suitable amount of the one or more active compounds in the drug and mixing the suitable amount with one or more excipients and/or carriers. Preferably, the excipient comprises sugar and/or starch.

In one specific embodiment of the instant invention the active compounds are biological, naturally occurring moieties such as natural biosynthesis products, small molecules, saccharides, lipids, nucleic acids, peptides and proteins extracted from microorganisms, fungi, or plant or animal life forms, or produced by modern chemical and biological techniques. According to the instant invention the naturally occurring moieties include antibodies and antibody fragments, including naturally occurring antibodies and/or antibody fragments and the ones produced by recombinant, phage and other immunological means either in vivo, ex vivo or in vitro. Yet according to another embodiment the active compounds are selected from synthetic compound libraries, including commercially available compound libraries and/or selected from the compound library expansion by means of modern combinatorial chemistry.

One embodiment of the invention relates to a method for selecting or identifying biologically active compounds from a library of compounds, said method comprising screening said library of compounds for biological or biochemical activity, wherein said screening includes assaying the library of compounds for the biological or biochemical activity.

The invention includes the use of the methods of the invention to screen for new drugs, preferably, by high-throughput screening (HTS), preferably involving screening of greater than 50, more preferably 100, more preferably 500, even more preferably 1,000, and most preferably 5,000. According to a particularly preferred embodiment, the screening involves greater than 10,000, greater than 50,000, greater than 100,000, greater than 500,000 and/or greater than 1,000,000 compounds. In one specific embodiment of the present invention the active compounds are selected from the libraries of FDA approved drugs, such as FDA2000.

Such screening and/or drug discovery methods include those set forth in U.S. Pat. No. 5,565,325 to Blake; U.S. Pat. No. 5,593,853 to Chen et al.; U.S. Pat. No. 5,721,135 to Thatrup et al., U.S. Pat. No. 5,985,585 to Daggett et al.; U.S. Pat. No. 5,684,711 to Agrafiotis et al.; U.S. Pat. No. 5,639,603 to Dower et al.; U.S. Pat. No. 5,569,588 to Ashby et al.; U.S. Pat. Nos. 5,541,061; 5,574,656; and U.S. Pat. No. 5,783,431 to Peterson et al.

According to another embodiment, the invention further comprises identifying adverse effects associated with the drug and storing information relating to the adverse effects in a database. See, U.S. Pat. No. 6,219,674 by Classen, hereby incorporated by reference.

The invention also includes bivalent inhibitors of E3 ubiquitin ligases, comprising a first moiety that binds the Type I site and a second moiety that binds the Type II site of an N-end rule E3 ligase, preferably UBR1. The two moieties are covalently linked through one or more covalent bonds. Preferably, the two moieties are covalently linked through one or more linking moieties providing, e.g., a bivalent inhibitor with structure M1-L-M2 where M1 is the first moiety, M2 is the second moiety and L is a linking moiety.

Suitable first and second moieties are, preferably, selected from moieties known to act as inhibitors of Type I or Type II N-end rule ubiquitylation and are, most preferably, Type I or Type II destabilizing amino acids. Preferably, the bivalent inhibitors have molecular weights of less than 2000, more preferably less than 1200 and most preferably less than 950 Daltons. Surprisingly, we have found that such small molecules comprising Type I and Type II inhibitors not only inhibit both Type I and Type II activities but also show better inhibition than a mixture of the corresponding monovalent inhibitors. Although applicants do not wish to be bound by theoretical explanations of the effect, such effect may be attributed to a stronger binding of a bivalent inhibitor to the E3 ligase through cooperative binding of the two moieties to the Type I and Type II sites.

In one embodiment of the invention, the bivalent inhibitors of the present invention are linear molecules. The Type I and Type II inhibiting moieties are, preferably, separated by less than 90 bonds, more preferably by less than 50 bonds, more preferably by less than 36 bonds, even more preferably by less than 30 bonds.

In an especially preferred embodiment, the bivalent inhibitors are peptides, preferably of less than 30 amino acid residues, more preferably of less than 25 amino acid residues, more preferably of less than 20 amino acid residues, more preferably of less than 12 residues.

Peptide-based inhibitors preferably comprise two N-terminal amino acids so as to provide Type I and Type II destabilizing residues. Such peptides may be made, e.g., by including in the peptide a branching monomer that has two amino groups. Linkage of the amino groups to the C-terminal residues of two peptide sequences (a first peptide sequence and a second peptide sequence) results in a peptide-based inhibitor having two N-termini. The two peptide sequences are chosen so that the N-terminal residue of the first peptide sequence is recognized by the Type I site and the N-terminal residue of the second peptide sequence is recognized by the Type II site. Especially preferred branching monomers are lysine and arginine, most preferably lysine where one of the peptide sequences is linked to the lysine via the alpha amino group and the other is linked via the epsilon amino group. The synthesis of branched peptides is easily accomplished by solid phase peptide synthesis and is well within the purvue of the skilled artisan.

One embodiment of inhibitors of the present invention are inhibitors of general chemical formula:

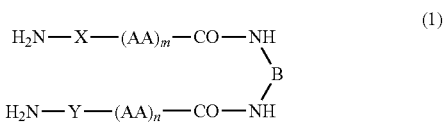

(1)

where X is an amino acid (inhibitor of Type I site) selected from the group of Arg, Lys and His;
Y is an amino acid (inhibitor of Type II site) selected from the group of Phe, Leu, Trp, Tyr, and Ile;
AA is any amino acid residue either naturally occurring, or synthetic;
B is a branching monomer, preferably Lys or Arg, most preferably Lys; and
n and m are in between 0 and 30 and where n+m is less or equal to 30.

In some specific embodiments of the invention, the preferred inhibitors of the present invention are of chemical formulae:

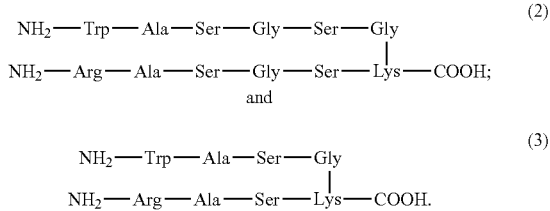

In structures 2 and 3, the vertical bond coming from the lysine refers to a peptide bond between the epsilon amino group of the lysine and the carboyl group of the attached glycine.

In one preferred embodiment, the invention relates to modulating the abundance and/or activity of N-end rule ubiquitylation substrates in vitro, ex vivo or in vivo. The modulation is achieved by mutating a site of proteolytic cleavage necessary to expose N-degron, preferably by mutating a key residue or by engineered a new cleavage site, thereby either retarding or accelerating degradation of an N-end rule substrate. In one preferred embodiment of the invention, the mutation is accelerating the substrate cleavage and/or the substrate clearance from the cell, thereby lowering the activity of the protein. Yet in another embodiment of the invention the mutation is inactivating the N-end rule pathway, therefore creating an overpopulation of a substrate of interest. Such overpopulation is desirable for studying protein function, or analyzing a protein-dependent phenotype.

Yet in another preferred embodiment the abundance of a substrate is modulated by administering one or more active compounds identified according to the present invention.

Yet in another embodiment the invention is directed to a method for generating a phenotypic line (cell, or animal) by modulating the abundance of a protein via enriching or inactivating N-end rule pathway for a specific protein. Such mutation may be used in a phenotypic background of an animal imitating a complex disease, such as for example modulating the abundance of protein tau in a background of a mouse overexpressing Aβ.

Another preferred embodiment the invention relates to a kit for producing and analysing polypeptides ubiquitylated via N-end rule pathway preferably polypeptides selected from proteins listed in Table 1, or variants thereof. The kit components are conveniently designed to provide DNA fragments, for example in a form of cDNA clones, or cDNA clones incorporated into appropriate vectors, preferably cDNA clones which encode proteins listed in Table 1, or variants thereof and reagents necessary to produce desired protein sequences by in vitro coupled transcription translation as described to the co-pending U.S. patent application Ser. No. 10/238,960, entitled "Methods, Reagents, Kits and Apparatus for Protein Function", incorporated herein by this reference. The kit may also include one or more assay components, such as (i) one or more binding reagents; (ii) a pH buffer; (iii) one or more blocking reagents; (iv) luminescent label; (v) luminescence co-reactant; (vi) preservatives; (vii) stabilizing agents; (viii) enzymes; (ix) detergents; and (x) desicants.

One specific embodiment relates to a kit which includes components required for active compound and/or pharmaceutical composition identification according to the methods of the instant invention.

The invention is further directed to methods of treating disease by administering pharmaceutical compositions comprising modulators of N-end rule ubiquitylation, preferably, modulators of the N-end rule ubiquitylation of a protein listed in Table 1. In certain embodiments of the invention, the modulator is a bivalent N-end rule inhibitor as described above.

One embodiment of the invention is a method for treating ataxia, preferably ocular motor ataxia, or Freidreich ataxia, a disease which is characterized by loss of aprataxin, a protein identified herein as an N-end rule ubiquitylation substrate. In one preferred embodiment of the invention, a therapeutic dose of an N-end rule ubiquitylation inhibitor, preferably a protease and/or ubiquitin ligase inhibitor, most preferably a protease inhibitor is administered into a patient in need thereof, thereby increasing the effective concentration of aprataxin. In another preferred embodiment, the disease is treated using gene therapy by introducing a clone encoding aprataxin but having a mutated protease cleavage site, where cleavage at the site in the unmodified protein leads to exposure of an N-degron. The mutation is selected to i) prevent proteolytic cleavage at the site and/or ii) prevent the exposure, on cleavage at the proteolytic cleavage site, of an N-degron. Such mutation will inhibit N-end rule dependent degradation of aprataxin, thereby increasing the lifetime of a protein, preferably reducing the necessary dose in gene therapy.

Another embodiment of the invention is a method for treating a neurodegenerative disorder selected from the group of neurodegenerative disorders generally characterized as tauopathies, preferably Alzheimer's disease, or Parkinson's disease, or Frontotemporal Dementia, which are characterized by neurofibrillary tangles formed predominantly from tau, a protein identified herein as an N-end rule ubiquitylation substrate. In one preferred embodiment of the invention, a therapeutic dose of an N-end rule ubiquitylation promoter is administered to a patient in need thereof, thereby accelerating the degradation of tau via the N-end rule dependent pathway. Yet another embodiment of the invention is a method of medical treatment by administering to a patient in need thereof a therapeutic dose of i) a protease which cleaves the tau protein and exposes an N-degron and/or ii) a ubiquitin ligase that ubiquitylates an activated fragment of tau having exposed an N-degron thereby accelerating tau degradation via the N-end rule dependent pathway.

Another embodiment of the invention is a method for treating a neurodegenerative disorder selected from the group of neurodegenerative disorders generally characterized by a disruption in neurotransmission via disruption in membrane trafficking or other mechanisms, for example Alzheimer's disease and Griscelli syndrome, which are linked to an aberrant performance of SLP, a protein identified herein as an N-end rule ubiquitylation substrate. In one preferred embodiment of the invention, a therapeutic dose of an N-end rule ubiquitylation modulator is administered to a patient in need thereof. The modulator is chosen to decelerate (e.g., by inhibiting the N-end rule E3 or a protease or other enzyme responsible for exposing a hidden N-degron) or accelerate (e.g., by enhancing the rate of an N-end rule E3) the effective degradation of a SLP via N-end rule dependent pathway. Deceleration is desirable, e.g., in the treatment of Alzheimer's diseases and acceleration is desirable, e.g., in the treatment of Griscelli syndrome. Yet another embodiment of the invention is a method of medical treatment by administering to a patient i) a therapeutic dose of a protease which cleaves the SLP protein and exposes an N-degron and/or ii) a ubiquitin ligase that ubiquitylates an activated fragment of a SLP having an exposed N-degron thereby accelerating a SLP degradation via the N-end rule dependent pathway. Yet another embodiment of the invention is a method of medical treatment by administering to a patient a therapeutic dose of i) an inhibitor of a protease which cleaves the SLP protein and exposes an N-degron and/or ii) an inhibitor of a ubiquitin ligase that ubiquitylates an activated fragment of a SLP having an exposed N-degron thereby decelerating a SLP degradation via the N-end rule dependent pathway.

Another embodiment of the invention is a method for treating a cancer that is characterized by the activation of a telomerase which can be inhibited by PinX1, a protein identified herein as an N-end rule substrate. In one preferred embodiment of the invention, a therapeutic dose of on N-end rule ubiquitylation inhibitor is administered to a patient, thereby decelerating the effective degradation of PinX1 via N-end rule dependent pathway. Yet another embodiment of the invention is a method of medical treatment by administering to a patient a therapeutic dose of i) an inhibitor of a protease which cleaves the PinX1 protein and exposes an N-degron and/or ii) an inhibitor of a ubiquitin ligase that ubiquitylates an activated fragment of PinX1 having an exposed N-degron thereby decelerating PinX1 degradation via the N-end rule dependent pathway and thereby inhibiting telomerase activity.

Another embodiment of the invention is a method for treating human disorders selected from the group of human neoplastic disease, cerebral autosomal dominant arteriopathy with subcortical infarcts and leucoencepholopathy, Alagille syndrome, Epstein-Barr virus-induced immortalization (the process associated with human malignancies such as Burkitt's lymphoma, nasopharyngeal carcinoma, Hodgkin's disease and lymphoproliferative disease in immunosuppressed patients) which are linked to an aberrant performance of CIR, a protein identified herein as an N-end rule ubiquitylation substrate. In one preferred embodiment of the invention, a therapeutic dose of an N-end rule ubiquitylation modulator is administered to a patient, thereby decelerating or accelerating the degradation of a CIR via the N-end rule dependent pathway. Yet another embodiment of the invention is a method of medical treatment by administering to a patient i) a therapeutic dose of a protease which cleaves the CIR protein and exposes an N-degron and/or ii) a ubiquitin ligase that ubiquitylates an activated fragment of a CIR having an exposed N-degron thereby accelerating CIR degradation via the N-end rule dependent pathway. Yet another embodiment of the invention is to method of medical treatment by administering to a patient a therapeutic dose of i) an inhibitor of a protease which cleaves the CIR protein and exposes an N-degron and/or ii) an inhibitor of a ubiquitin ligase that ubiquitylates an activated fragment of a CIR having an exposed N-degron thereby decelerating CIR degradation via the N-end rule dependent pathway.

Another embodiment of the invention is a method for treating diseases and/or disorders generally characterized by a disruption in protein processing and clearance which involves a putative E3 ligase Cullin-3, a protein identified herein as an N-end rule ubiquitylation substrate. In one preferred embodiment of the invention, a therapeutic dose of an N-end rule ubiquitylation modulator is administered to a patient, thereby decelerating (e.g., in case of overexpression of cyclin D1, a cullin-3 substrate, which has been implicated in a variety of tumors such as breast cancers, gastrointestinal tumors and lymphomas) the degradation of a Cullin-3 via the N-end rule dependent pathway and improving target substrate clearance or accelerating (e.g., in case of katanin, a cullin-3 substrate, which has been implicated in a suppression of microtubule instability) the degradation of a Cullin-3 via N-end rule dependent pathway thereby reducing the clearance of a target protein. Yet another embodiment of the invention is a method of medical treatment by administering to a patient i) a therapeutic dose of a protease which cleaves the cullin-3 protein and exposes an N-degron and/or ii) a ubiquitin ligase that ubiquitylates an activated fragment of a cullin-3 having an exposed N-degron thereby accelerating cullin-3 degradation via the N-end rule dependent pathway. Yet another embodiment of the invention is a method of medical treatment by administering to a patient a therapeutic dose of i) an inhibitor of a protease which cleaves cullin-3 protein and exposes an N-degron and/or ii) an inhibitor of a ubiquitin ligase that ubiquitylates an activated fragment of cullin-3 having an exposed N-degron thereby decelerating cullin-3 degradation via the N-end rule dependent pathway.

One embodiment of the invention is a method for improving astrocyte differentiation in response to CNS injury, which is achieved by modulating the concentration of HMGN3, a protein identified herein as an N-end rule ubiquitylation substrate. In one preferred embodiment of the invention, a therapeutic dose of an N-end rule ubiquitylation inhibitor, preferably a protease and/or ubiquitin ligase inhibitor, most preferably a protease inhibitor is administered to a patient, thereby increasing the effective concentration of HMGN3. In another preferred embodiment, the disease is treated using gene therapy by introducing a clone encoding HMGN3 but having a mutated protease cleavage site, where cleavage at the site in the unmodified protein leads to exposure of an N-degron. The mutation is selected to i) prevent proteolytic cleavage at the site and/or ii) prevent the exposure, on cleavage at the proteolytic cleavage site, of an N-degron. Such mutations will inhibit the N-end rule dependent degradation of HMGN3, thereby increasing the lifetime of a protein, preferably reducing the necessary dose in gene therapy. Yet another embodiment of the invention is a method of medical treatment by administering to a patient i) a therapeutic dose of an inhibitor of a protease which cleaves HMGN3 protein and exposes an N-degron and/or ii) an inhibitor of a ubiquitin ligase that ubiquitylates an activated fragment of HMGN3 having an exposed N-degron thereby decelerating HMGN3 degradation via N-end rule dependent pathway.

Another embodiment of the invention is a method for treating certain lymphomas, which are characterized by aberrant lymphocyte apoptosis regulation by HSPC144, a protein identified herein as an N-end rule ubiquitylation substrate. In one preferred embodiment of the invention, a therapeutic dose of an N-end rule ubiquitylation promoter is administered to a patient, thereby accelerating the degradation of HSPC144 via the N-end rule dependent pathway. Yet another embodiment of the invention is a method of medical treatment by administering to a patient i) a therapeutic dose of a protease which cleaves the HSPC144 protein and exposes an N-degron and/or ii) a ubiquitin ligase that ubiquitylates an activated fragment of HSPC144 having an exposed N-degron thereby accelerating HSPC144 degradation via the N-end rule dependent pathway.

One embodiment of the invention is a method for treating certain types of cancers, which are characterized by down-regulation of the expression of cdc6, a protein identified herein as an N-end rule ubiquitylation substrate. In one preferred embodiment of the invention, a therapeutic dose of an N-end rule ubiquitylation inhibitor, preferably a protease and/or ubiquitin ligase inhibitor, most preferably a protease inhibitor is administered to a patient, thereby increasing the effective concentration of cdc6. In another preferred embodiment, the disease is treated using gene therapy by introducing a clone encoding cdc6 but having a mutated protease cleavage site, where cleavage at the site in the unmodified protein leads to exposure of an N-degron. The mutation is selected to i) prevent proteolytic cleavage at the site and/or ii) prevent the exposure, on cleavage at the proteolytic cleavage site, of an N-degron. Such mutations will inhibit N-end rule dependent degradation of cdc6, thereby increasing the lifetime of a protein, preferably reducing the necessary dose in gene therapy. Yet another embodiment of the invention is a method of medical treatment by administering to a patient a therapeutic dose of i) an inhibitor of a protease which cleaves cdc6 protein and exposes an N-degron and/or ii) an inhibitor of a ubiquitin ligase that ubiquitylates an activated fragment of Cdc6 having an exposed N-degron thereby decelerating Cdc6 degradation via the N-end rule dependent pathway.

Another embodiment of the invention is a method for treating certain diseases, which are characterized by aberrant cell differentiation regulation by HMGN2, a protein identified herein as an N-end rule ubiquitylation substrate. In one preferred embodiment of the invention, a therapeutic dose of an N-end rule ubiquitylation promoter is administered to a patient, thereby accelerating the degradation of HMGN2 via the N-end rule dependent pathway. Yet another embodiment of the invention is a method of medical treatment by administering to a patient i) a therapeutic dose of a protease which cleaves the HMGN2 protein and exposes an N-degron and/or ii) a ubiquitin ligase that ubiquitylatea an activated fragment of HMGN2 having an exposed N-degron thereby accelerating HHMGN2 degradation via the N-end rule dependent pathway.

A person of ordinary skill in the art will readily recognize the possible modification to the methods of treating diseases described above.

7. EXAMPLES

The following examples are illustrative of some of the methods falling within the scope of the present invention. They are, of course, not to be considered in any way limitative of the invention. Numerous changes and modifications can be made with respect to the invention by one of ordinary skill in the art without undue experimentation.

Materials and Methods
Preparation of Plasmid DNA:

Studies on N-end rule substrates were conducted using proteins produced using the following IMAGE Consortium clones: IMAGE ID #3994375 (aprataxin), #3887570 (synaptotagmin-like protein), #4448167 (microtubule-associated protein tau), #3447081 or #3455121 (both HMGN2), #3890883 or #4749335 (both HMGN3), 43867414 (cell cycle controller Cdc6), #4426807 (cullin 3), #3910222 (CBF1 interacting protein (CIR)), #3907737 (HSPC144) and #3911679 (PIN2 interacting protein I (PINX1)). Bacteria containing clones were grown in 25 ml LB with 250 µg/ml Amp and DNA was isolated using QIAprep Spin Midiprep Kits (Qiagen). DNA yield was 100-150 µg.

Streptavidin Labeled with Electrochemiluminescent Labels:

The label Compound 1 pictured below (Sulfo-TAG™ NHS Ester, Meso Scale Discovery, a division of Meso Scale Diagnostics, LLC, Gaithersburg, Md.) was used to label streptavidin for electrochemiluminescence measurements.

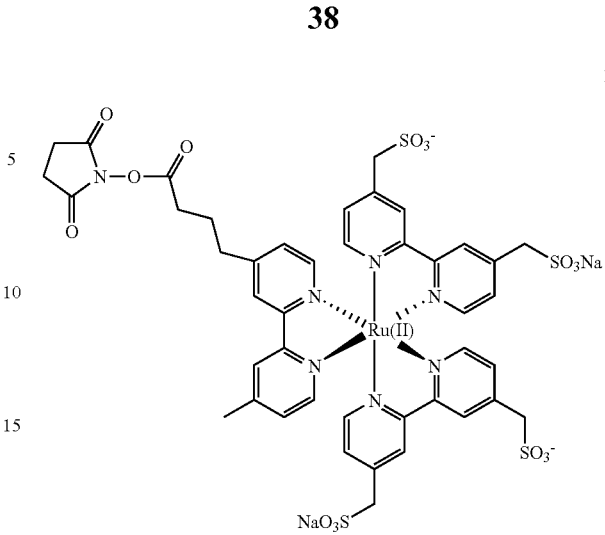

Labeling of streptavidin was carried out by adding the Sulfo-TAG NHS Ester to a solution of the streptavidin molecules in phosphate buffered saline, pH 8.0. The labeled protein was purified from unbound label by size exclusion chromatography using Sephadex G50 (Pharmacia Biosciences). The average number of labels per protein molecule (typically around 11) was calculated from the concentration of labels (calculated from the extinction coefficient of Sulfo-TAG label at 455 nm, $\epsilon_{455}$~15,400 $M^{-1}$ $cm^{-1}$) and the concentration of streptavidin (determined using the BCA Protein Assay, Pierce Chemicals)

Multi-Well Plates for Electrochemiluminescence Measurements:

Electrochemiluminescence measurements were carried out using specially designed multi-well plates having integrated carbon ink electrodes for carrying out electrochemiluminescence measurements (Multi-Array™ or Multi-Spot™ plates, Meso Scale Discovery, a division of Meso Scale Diagnostics, LLC, Gaithersburg, Md.). A dielectric layer patterned over the working electrode in each well exposed four regions or "spots" on the working electrode. The exposed working electrode in two of the spots was coated with FK2 (Affiniti Research Products) a mouse monoclonal antibody that is specific for poly-ubiquitylated proteins. Another spot was coated with BSA and used as a negative control. FK2 was diluted to 0.1-0.5 mg/ml with PBS, pH7.4, 0.015% Triton-X100, microdispensed (250 nl per spot) onto two spots of each well of a 4-Spot Multi-Spot plate and air-dried for 5 hours. Then 200 µl of a blocking solution (PBS, pH7.2, 5% BSA 0.1% 2-chloroacetamide) was introduced into each well and blocking was performed overnight at 4° C. The plates were washed three times with PBS prior to use.

Electrochemiluminescence Measurement Instrument:

Electrochemiluminescence was induced and measured in the Multi-Spot plates using a Sector HTS™ reader (Meso Scale Discovery, a division of Meso Scale Diagnostics, LLC, Gaithersburg, Md.).

Electrochemiluminescence Assay for Substrates of N-End Rule-Dependent Ubiquitylation:

Protein was produced from the plasmid DNA in a transcription-translation reaction mixture containing rabbit reticulocyte lysate and SP6 RNA polymerase (TNT SP6 Quick Mix, Promega) and that was further supplemented with 20 µM methionine, 8-30 µg/ml plasmid DNA, 20 µg/ml biotinylated Lys-tRNA (transcend tRNA, Promega), and 50 µM of the proteosome inhibitor MG-132 (Calbiochem) in a total volume of 12.5 μl. Ubiquitylation of newly synthesized proteins occurred in the same reaction mixtures and was driven by the ubiquitylation system present in reticulocyte lysates. An ECL-based ubiquitylation assay (described below) was used to determine if the newly synthesized protein was ubiquitylated. To determine if the protein produced from each clone was ubiquitylated through the N-end rule pathway, the ECL ubiquitylation assay was repeated in the presence of 1 mM Arg-β-Ala (an inhibitor of ubiquitylation of Type I N-end rule substrates), 1 mM Trp-Ala (an inhibitor of ubiquitylation of Type I N-end rule substrates), 1 mM of each of the two dipeptide inhibitors, or, in some experiments, 1 mM of bivalent inhibitor 3, an inhibitor comprising peptide sequences having both N-terminal Arg-Ala and Trp-Ala moieties. These reactions were carried out in the presence of 0.15 nM bestatin, an aminopeptidase inhibitor that was added to prevent degradation of the dipeptide inhibitors.

The reactions were allowed to proceed for a desired period of time at 30° C. In some experiments, several reaction time points were analyzed. Then 1 μl of each reaction mixture was mixed with 50 μl binding buffer (20 mM Tris-HCl, 150 mM NaCl, pH7.4, 0.1% BSA, 0.2% Tween-20, 20 mM EDTA, and a cocktail of protease inhibitors (Roche Applied Sciences)) containing 1 μg/ml sulfotag-labeled streptavidin in the well of the FK2-coated Multi-Spot plates. The plate was incubated on a tabletop shaker for 1 hour. During this time, newly synthesized proteins comprising both a biotin label and polyubiquitin bind to both immobilized FK2 and Sulfo-TAG labeled streptavidin resulting in the accumulation of Sulfo-TAG labels on the FK2 "spot". Thereafter the plate was washed three times with 20 mM Tris-HCl, 0.004% Triton X-100 followed by addition of 150 μl of a buffered solution containing tripropylamine (MSD Read Buffer, Meso-Scale Discovery, Gaithersburg Md.) into each well. ECL signals from labels bound to the electrode surfaces were measured using a Sector HTS instrument.

Analysis of N-End Rule-Dependent Degradation of Proteins by Denaturing Gel:

Proteins were synthesized as described in the previous section except that biotinylated Lys-tRNA was substituted with [$^{14}$C]-lysine, and MG-132 was omitted. The reactions were incubated at 30° C. for indicated times. They were stopped by transferring of aliquots of reactions into SDS-sample buffer. The samples were heated for 5 min at 95° C. and fractionated by SDS-PAGE on 4-20% gradient polyacrylamide gels. Gels were soaked in Amplify™ fluorographic reagent (Amersham Pharmacia Biotech), dried and exposed to X-ray films.

Example 1

RGS4 a Known N-End Rule Ubiquitylation Substrate is Confirmed as an N-End Rule Substrate RGS4 was produced and characterized as an N-end rule substrate as described in the Materials and Methods section. RGS4 is a known Type 1 N-end rule ubiquitylation substrate (Davydov and Varshavsky, 2000, *J. Biol. Chem.*, 275: 22931).

Figure 2A:
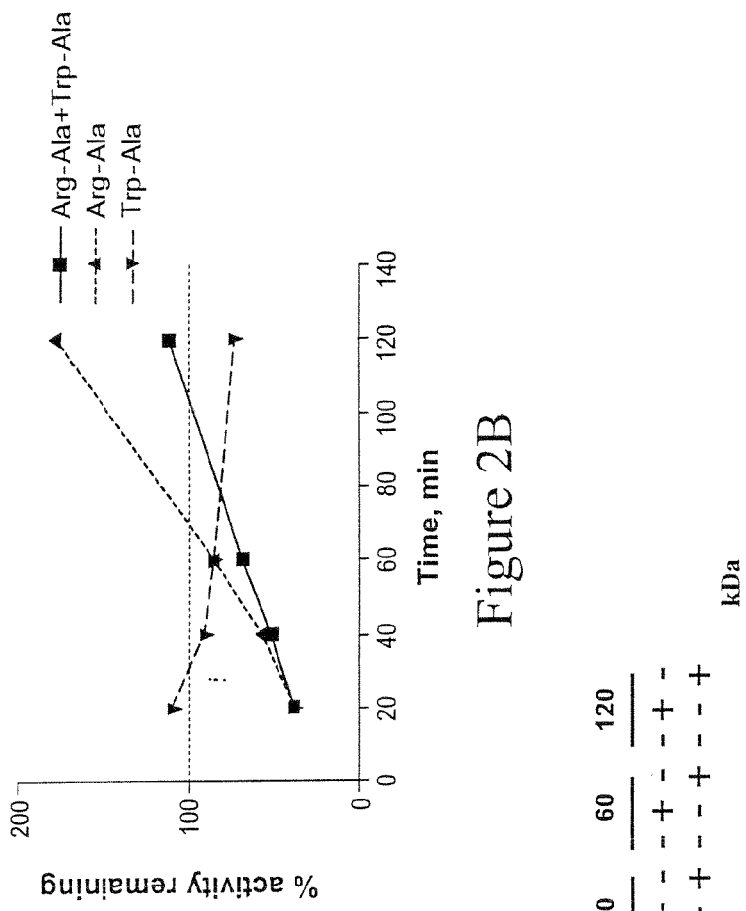
FIG. 2 shows (A) the time course for an ECL assay for N-end rule ubiquitylation of RGS4; (B) the % inhibition of the ECL signal in the presence of N-end rule inhibitors; and (C) gel electrophoretic analysis of the products of the ubiquitylation reactions.
Figure 2B:
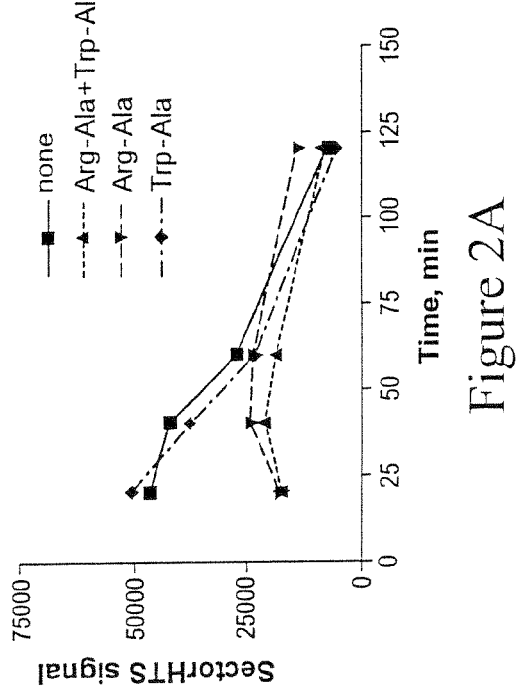

FIG. 2(A) shows the time course of the accumulation of ubiquitylated RGS4. FIG. 2(B) shows the % of RGS4 ubiquitylation in the presence of specific N-end rule inhibitors compared to the reaction in the absence of the inhibitors. FIGS. 2(A) and (B) show that the mixture of Arg-β-Ala and Trp-Ala dipeptides and Arg-β-Ala alone (Type I inhibitor) inhibit RGS4 ubiquitylation to a similar extent, while Trp-Ala alone (Type II inhibitor) has little to no effect. These results identify RGS4 as a Type 1 substrate for an N-end rule ubiquitylation pathway.

Figure 2C:
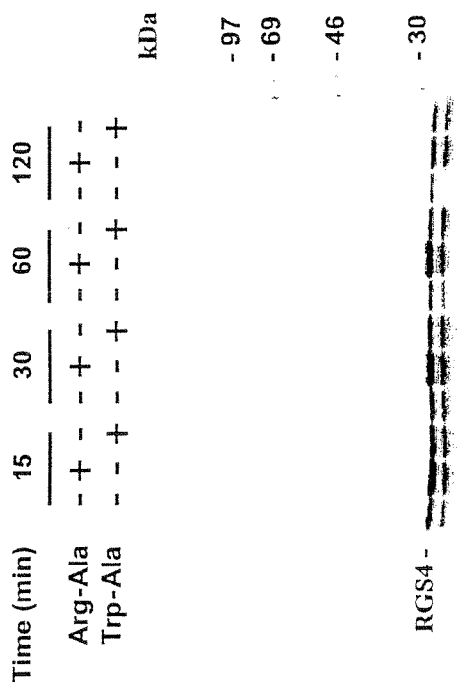

The autoradiogram pictured in FIG. 2(C) indicates that N-end rule ubiquitylation of RGS4 most likely proceeds after a proteolytic cleavage event exposes an N-degron. FIG. 2(C) shows the time course of RGS4 ubiquitin/proteosome degradation via N-end rule pathway in the presence or absence of a Arg-β-Ala or Trp-Ala dipeptide inhibitors of E3 ubiquitin ligase. The C-terminal fragment of a RGS4 having the N-terminal Met removed shows a time dependent accumulation exclusively in the presence of Arg-β-Ala inhibitor, confirming it as a Type I N-end rule ubiquitylation substrate. In the absence of the inhibitors the fragment is presumably degraded via the N-end rule pathway.

Example 2

Microtubule-Associated Protein Tau is an N-End Rule Ubiquitylation Substrate

Microtubule-Associated Protein Tau (MAPT, tau) was produced using IMAGE clone #4448167 and analyzed for its ability to act as an N-end rule substrate by ECL assay and by gel electrophoresis as described in the Materials and Methods.

FIG. 3(A) shows the time course of the accumulation of ubiquitylated tau. FIG. 3(B) shows the % of tau ubiquitylation in the presence of specific N-end rule inhibitors compared to the reaction in the absence of the inhibitors. FIGS. 3(A) and (B) show that the mixture of Arg-β-Ala and Trp-Ala dipeptides and Arg-β-Ala alone (Type I inhibitor) inhibit tau ubiquitylation to a similar extent, while Trp-Ala alone (Type II inhibitor) has little to no effect. These results identify tau as a Type 1 substrate for an N-end rule ubiquitylation pathway.

The autoradiograms pictured in FIGS. 3(C) and 3(D) indicate that N-end rule ubiquitylation of tau most likely proceeds after a proteolytic cleavage event exposes an N-degron. FIG. 3(C) shows the time course of tau ubiquitin/proteosome degradation via N-end rule pathway in the presence or absence of a mixture of Arg-β-Ala and Trp-Ala dipeptide inhibitors of E3 ubiquitin ligase. FIG. 3(D) is an overexposed version of FIG. 3(C). The proteolytic degradation of tau appears to be a complex process involving multiple cleavage events, as apparent from the complex ladder formation seen on the gel. However, the time dependent accumulation of ~15-20 kDa activated fragment of tau exclusively in the presence of the inhibitors (FIG. 3(D) pointer) identifies tau as an N-end rule ubiquitylation substrate. In the absence of the inhibitors, this fragment is presumably degraded via N-end rule pathway.

Example 3

Aprataxin is an N-End Rule Ubiquitylation Substrate

Aprataxin was produced using IMAGE clone #3994375 and analyzed for its ability to act as an N-end rule substrate by ECL assay and by gel electrophoresis as described in the Materials and Methods.

FIG. 4(A) shows the time course of the accumulation of ubiquitylated aprataxin. FIG. 4(B) shows the % of aprataxin ubiquitylation in the presence of specific N-end rule inhibitors compared to the reaction in the absence of the inhibitors. FIGS. 4(A) and (B) show that the mixture of Arg-β-Ala and Trp-Ala dipeptides and Arg-β-Ala alone (Type I inhibitor) inhibit aprataxin ubiquitylation to a similar extent, while Trp- Ala alone (Type II inhibitor) has little to no effect. These results identify aprataxin as a Type 1 substrate for an N-end rule ubiquitylation pathway.

FIG. 4(A) also shows that, at equivalent concentrations, bivalent peptide inhibitor 2 provides better inhibition of aprataxin ubiquitylation than the mixture of Arg-β-Ala and Trp-Ala dipeptides and Arg-β-Ala alone. Although applicants do not wish to be bound by theoretical explanations of the effect, such effect may be attributed to a stronger binding of a bivalent inhibitor to E3 ligase due to cooperative binding at two different sites.

The autoradiogram pictured in FIG. 4(C) indicates that N-end rule ubiquitylation of aprataxin most likely proceeds after a proteolytic cleavage event exposes an N-degron. FIG. 4(C) shows the time course of aprataxin ubiquitin/proteosome degradation via N-end rule pathway in the presence or absence of a mixture of Arg-β-Ala and Trp-Ala dipeptide inhibitors of E3 ubiquitin ligase. Band 1 (aprataxin) shows a time dependent retardation in the degradation of an aprataxin in the presence of the inhibitors. The retardation is seen predominantly at later time points. Bands 2 (~20-21.5 kDa C-terminal fragment of aprataxin) and 3 (~16.5-18 kDa N-terminal fragment of aprataxin) are derived from the starting molecule in band 1 via a single proteolytic cleavage. Band 2 (C-terminal fragment of aprataxin) shows a time dependent accumulation exclusively in the presence of inhibitors, confirming it as an N-end rule ubiquitylation substrate. In the absence of the inhibitors, the fragment is presumably degraded via the N-end rule pathway. Finally, band 3 corresponds to N-terminal fragment of aprataxin—a product of a proteolytic cleavage necessary to expose N-degron.

The molecular weights of the bands place the protease cleavage site between residues 150-160 of aprataxin. The exact site is identified by scanning mutagenesis starting with residues Glu, Gln, Cys, Arg, Lys, His specific to Type I N-end rule substrate within this segment, or by mass-spectroscopy.

Example 4

Synaptotagmin-Like Protein 2 is an N-End Rule Ubiquitylation Substrate

Synaptotagmin-like protein 2 was produced using IMAGE clone #3887550 and analyzed for its ability to act as an N-end rule substrate by ECL assay and by gel electrophores is as described in the Materials and Methods.

FIG. 5(A) shows the time course of the accumulation of ubiquitylated synaptotagmin-like protein 2. FIG. 5(B) shows the % of synaptotagmin-like protein 2 ubiquitylation in the presence of specific N-end rule inhibitors compared to the reaction in the absence of the inhibitors. FIGS. 5(A) and (B) show that the mixture of Arg-β-Ala and Trp-Ala dipeptides and Trp-Ala alone (Type II inhibitor) inhibit synaptotagmin-like protein 2 ubiquitylation to a similar extent, while Arg-β-Ala alone (Type I inhibitor) has little to no effect. These results identify synaptotagmin-like protein 2 as a Type II substrate for an N-end rule ubiquitylation pathway.

FIG. 5(A) also shows that bivalent peptide inhibitor 2 provides better inhibition of synaptotagmin-like protein 2 ubiquitylation than the mixture of Arg-β-Ala and Trp-Ala dipeptides and Trp-Ala alone.

The autoradiogram pictured in FIG. 5(C) indicate that N-end rule ubiquitylation of synaptotagmin-like protein 2 most likely proceeds after a proteolytic cleavage event exposes an N-degron. FIG. 5(C) show the time course of an synaptotagmin-like protein 2 ubiquitin/proteosome degradation via N-end rule pathway in the presence or absence of a mixture of Arg-β-Ala and Trp-Ala dipeptide inhibitors of E3 ubiquitin ligase. Band 1 (synaptogmin-like protein 2) shows a time dependent retardation in the degradation of a synaptotagmin-like protein 2 in the presence of the inhibitors. Band 2 (C-terminal fragment of synaptotagmin-like protein 2) is derived from a starting molecule in band 1 via a single proteolytic cleavage that removes a small N-terminal fragment of no more than 50 amino acid residues. Band 2 (C-terminal fragment of synaptotagmin-like protein 2) shows the time dependent accumulation exclusively in the presence of inhibitors, which identifies it as an N-end rule ubiquitylation substrate. In the absence of the inhibitors, this fragment is presumably degraded via N-end rule pathway. Finally, the lack of observed N-terminal fragment of synaptotagmin-like protein 2—a product of a proteolytic cleavage necessary to expose N-degron may result from a cleavage site located very close to the N-terminus of synaptotagmin-like protein 2, most likely within the first 50 amino acids.

The data identified the cleavage site to be located within the first 50 amino acid residues of synaptotagmin-like protein 2. The site location is refined by scanning mutagenesis starting with residues Leu, Ile, Tyr, Phe, Trp specific for Type II substrate, within the first 50 amino acids, or by mass-spectroscopy.

The cleavage site is also identified when Synaptotagmin-like protein 2 is produced using IMAGE clone #3887550 having an engineered affinity purification tag which allows capture of an N-terminal fragment followed by sequencing.

Example 5

HMGN2 (HMG17) is an N-End Rule Ubiquitylation Substrate

High Mobility Group Chromosomal Protein 17 (now renamed HMGN2) was produced using IMAGE clone #3455121 and analyzed for its ability to act as an N-end rule substrate by ECL assay as described in Materials and Methods. Alternatively IMAGE clone #3447081 may be used.

Figure 6B:
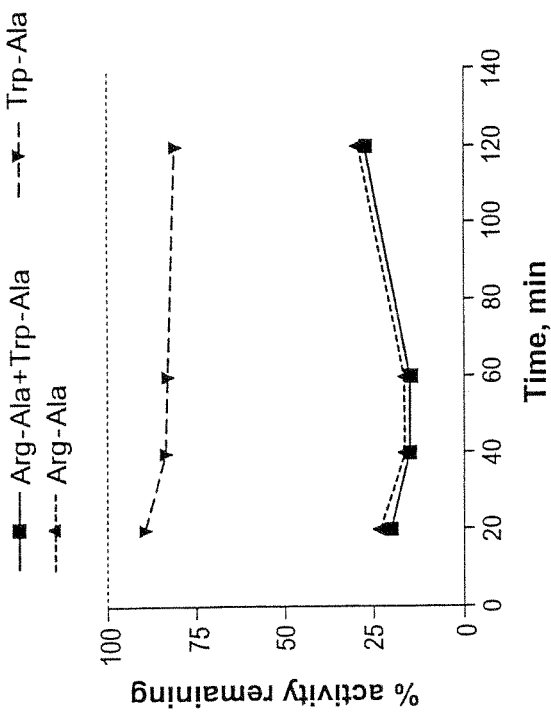
FIG. 6 shows (A) the time course for an ECL assay for N-end rule ubiquitylation of HMGN2; and (B) the % inhibition of the ECL signal in the presence of N-end rule inhibitors.
Figure 6A:
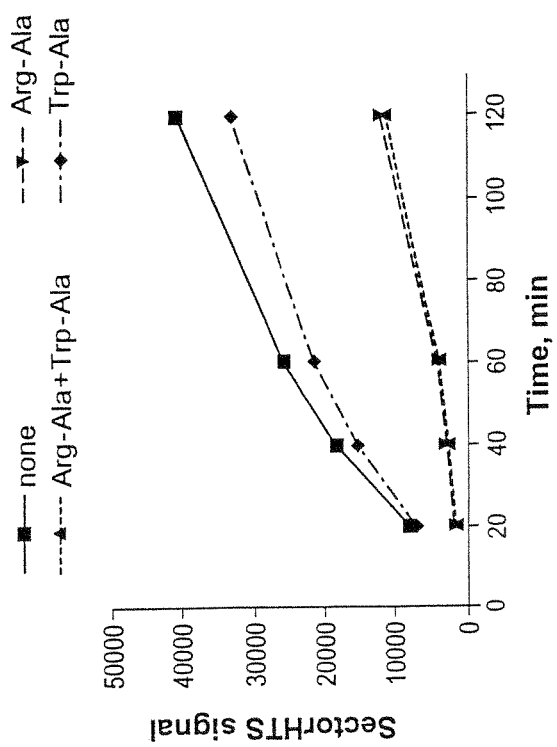

FIG. 6(A) shows the time course of the accumulation of ubiquitylated HGMN2. FIG. 6(B) shows the % of HMGN2 ubiquitylation in the presence of specific N-end rule inhibitors compared to the reaction in the absence of the inhibitors. The FIGS. 6(A) and (B) show that the mixture of Arg-β-Ala and Trp-Ala dipeptides and Arg-β-Ala alone (Type I inhibitor) inhibit HMGN2 ubiquitylation to a similar extent, while Trp-Ala alone (Type II inhibitor) has little to no effect. These results identify HMGN2 as a Type 1 substrate for an N-end rule ubiquitylation pathway.

Example 6

Cell Cycle Controller Cdc6 is an N-End Rule Ubiquitylation Substrate

Cell Cycle Controller cdc6 was produced using IMAGE clone #3867414 and analyzed for its ability to act as an N-end rule substrate by ECL assay and by gel electrophoresis as described in the Materials and Methods.

Figure 7A:
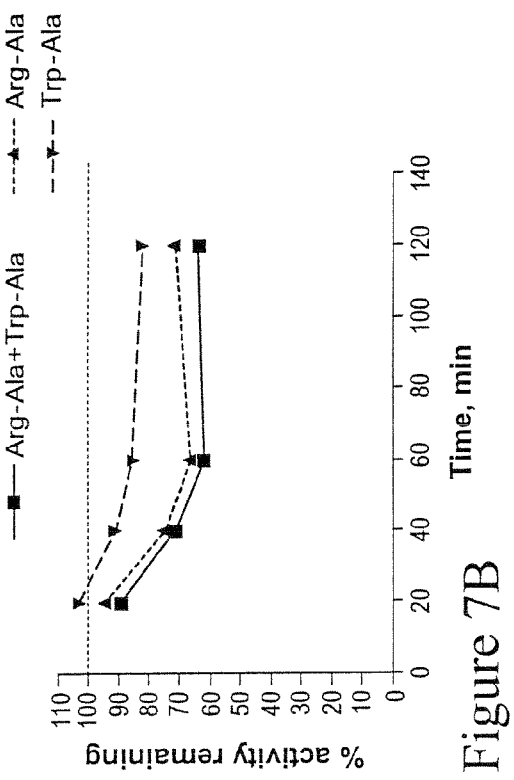
FIG. 7 shows (A) the time course for an ECL assay for N-end rule ubiquitylation of CDC6; (B) the % inhibition of the ECL signal in the presence of N-end rule inhibitors; and (C) gel electrophoretic analysis of the products of the ubiquitylation reactions.
Figure 7B:
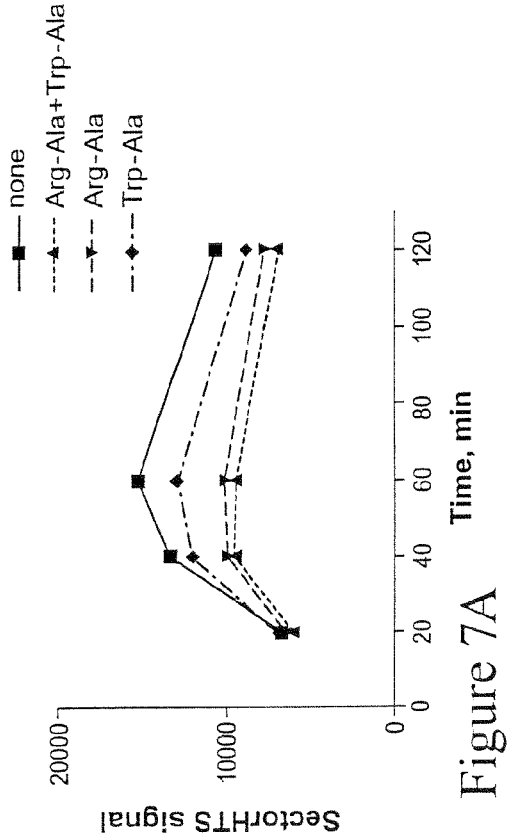

FIG. 7(A) shows the time course of the accumulation of ubiquitylated cdc6. FIG. 7(B) shows the % of cdc6 ubiquitylation in the presence of specific N-end rule inhibitors compared to the reaction in the absence of the inhibitors. FIGS. 7(A) and (B) show that the mixture of Arg-β-Ala and Trp-Ala dipeptides and Arg-β-Ala alone (Type I inhibitor) inhibit cdc6 ubiquitylation to a similar extent, while Trp-Ala alone (Type II inhibitor) has smaller effect. These results identify cdc6 as a Type 1 substrate for an N-end rule ubiquitylation pathway.

Figure 7C:
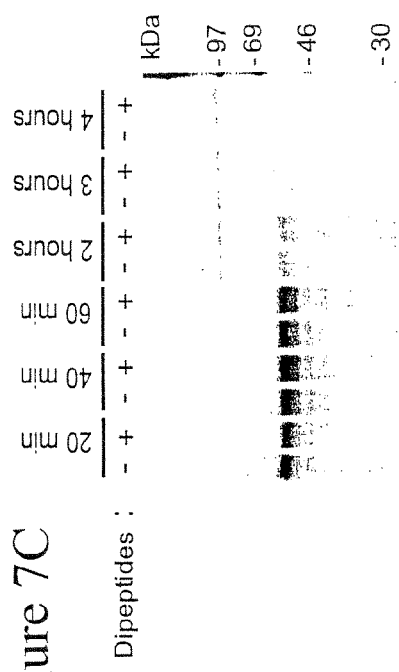

The autoradiogram pictured in FIG. 7(C) indicates that N-end rule ubiquitylation of cdc6 most likely proceeds after a proteolytic cleavage event exposes an N-degron. FIG. 7(C) show the time course of a Cell Cycle Controller cdc6 ubiquitin/proteosome degradation via N-end rule pathway in the presence or absence of a mixture of Arg-β-Ala and Trp-Ala dipeptide inhibitors of E3 ubiquitin ligase. The proteolytic degradation of Cdc6 appears to be a complex process involving multiple cleavage events, as apparent from the complex ladder formation seen on the gel. The protein is clearly unstable as evidenced from a disappearance of a major band (Cdc6 ~55 kDa) after 2 hours. However, the cdc6 band at about 55 kDa shows slight time dependent retardation in its degradation in the presence of the inhibitors. The retardation is seen predominantly at medium (~2 hrs) time points. Also bands at about ~40-45 k-Da shows a time dependent accumulation exclusively in the presence of inhibitors, which confirms cdc6 as an N-end rule ubiquitylation substrate. In the absence of the inhibitors the fragment is presumably degraded via the N-end rule pathway.

Example 7

HSPC144 is an N-End Rule Ubiquitylation Substrate

HSPC144 was produced using IMAGE clone #3907737 and analyzed for its ability to act as an N-end rule substrate by ECL assay as described in the Materials and Methods.

Figure 8B:
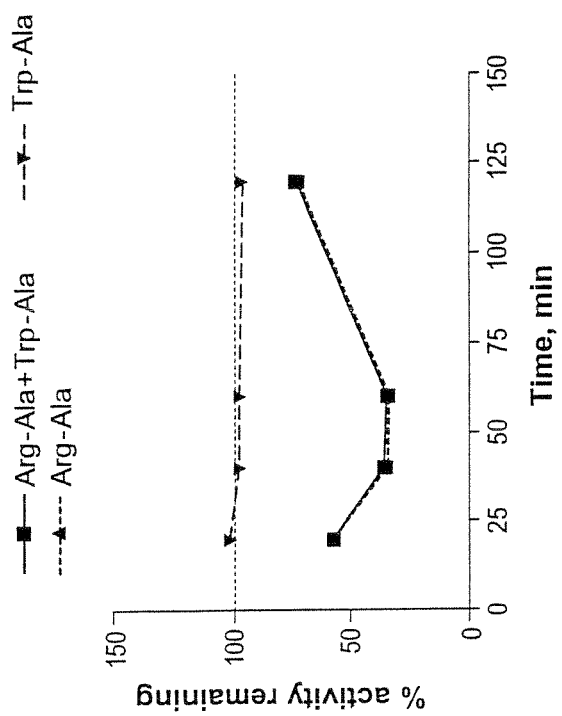
FIG. 8 shows (A) the time course for an ECL assay for N-end rule ubiquitylation of HSPC144 and (B) the % inhibition of the ECL signal in the presence of N-end rule inhibitors.
Figure 8A:
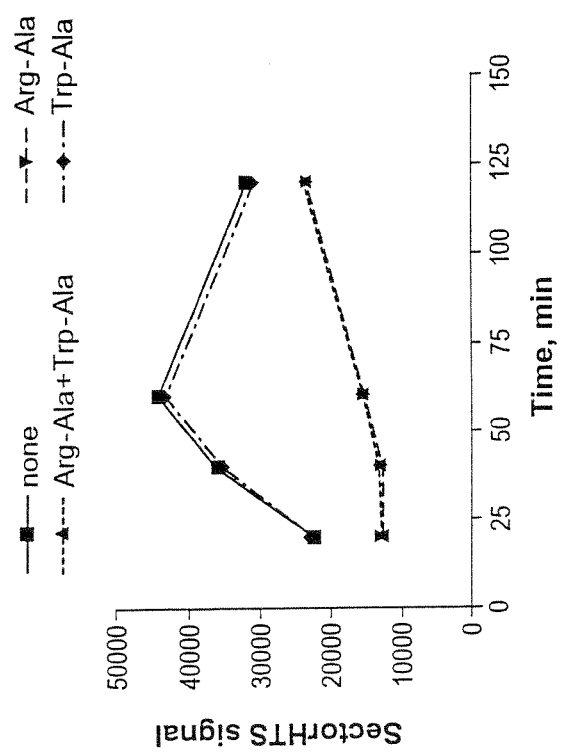

FIG. 8(A) shows the time course of the accumulation of ubiquitylated HSPC144. FIG. 8(B) shows the % of HSPC144 ubiquitylation in the presence of specific N-end rule inhibitors compared to the reaction in the absence of the inhibitors. FIGS. 8(A) and (B) show that the mixture of Arg-β-Ala and Trp-Ala dipeptides and Arg-β-Ala alone (Type I inhibitor) inhibit HSPC ubiquitylation to a similar extent, while Trp-Ala alone (Type II inhibitor) has no effect. These results identify HSPC144 as a Type 1 substrate for an N-end rule ubiquitylation pathway.

Example 8

PIN2 Interacting Protein 1 (PinX1) is an N-End Rule Ubiquitylation Substrate

PinX1 was produced using IMAGE clone #3911679 and analyzed for its ability to act as an N-end rule substrate by ECL assay as described in the Materials and Methods.

Figure 9B:
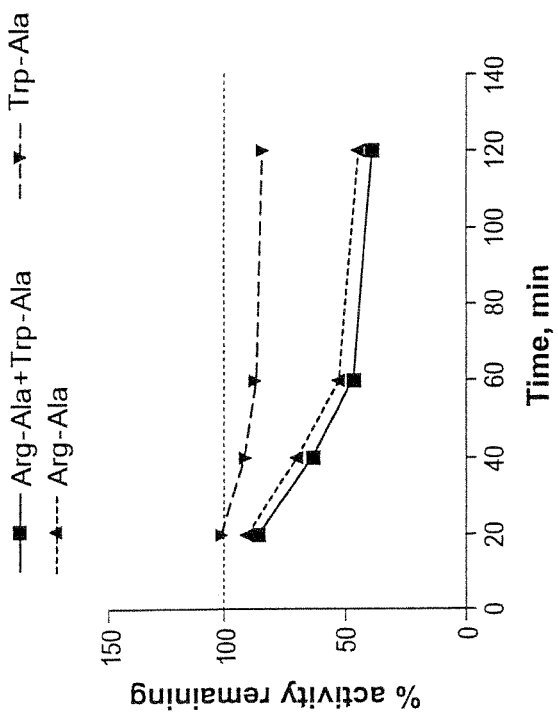
FIG. 9 shows (A) the time course for an ECL assay for N-end rule ubiquitylation of PinX1 and (B) the % inhibition of the ECL signal in the presence of N-end rule inhibitors.
Figure 9A:
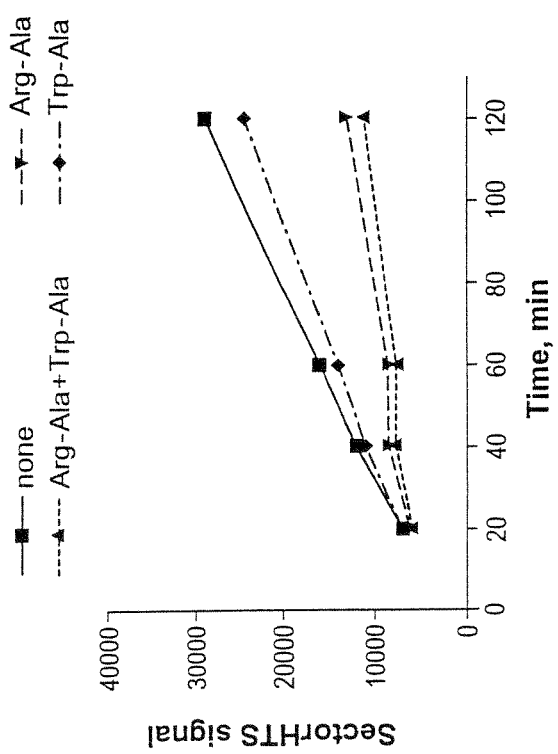
Figure 10B:
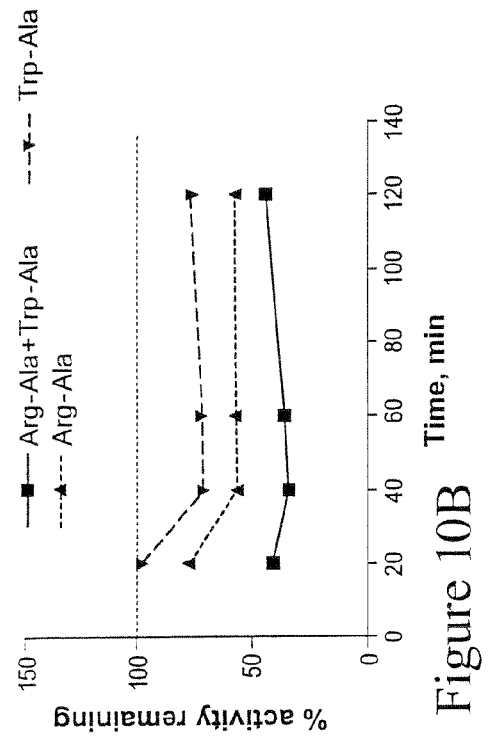
FIG. 10 shows (A) and (C) the time course for an ECL assay for N-end rule ubiquitylation of the products produced from two clones of HMGN3 and (B) and (D) the % inhibition of the ECL signal from these two clones in the presence of N-end rule inhibitors.
Figure 10D:
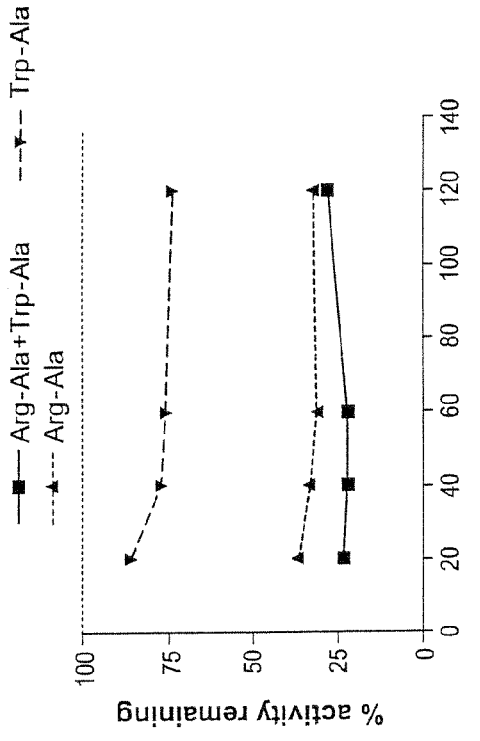
Figure 10A:
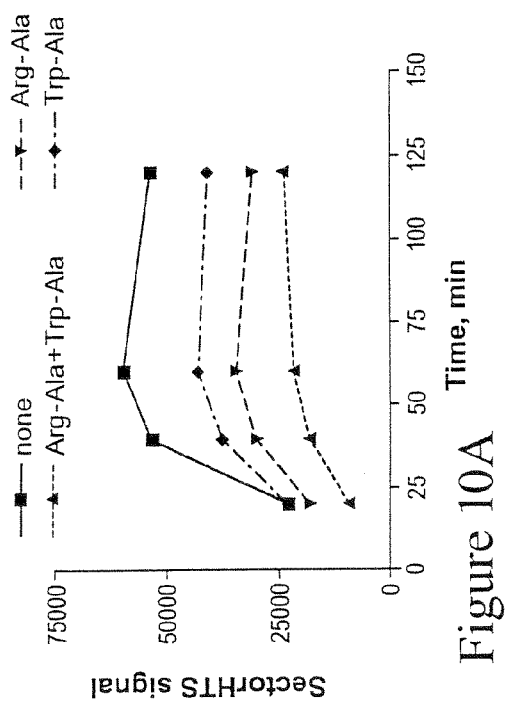
Figure 10C:
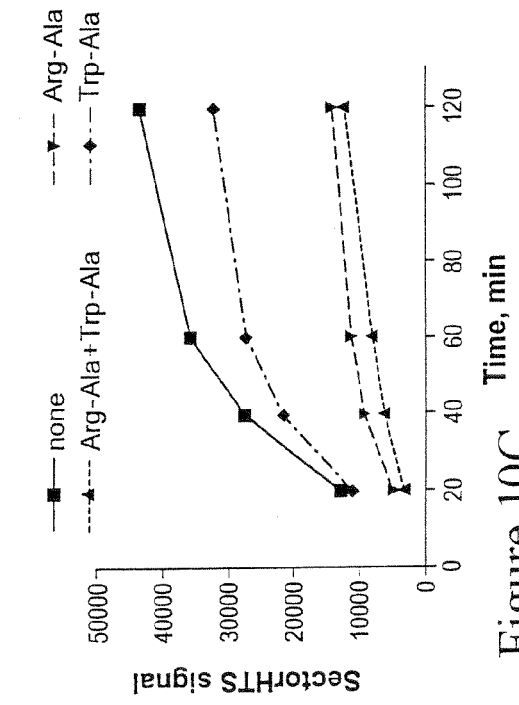

FIG. 9(A) shows the time course of the accumulation of ubiquitylated PinX1. FIG. 9(B) shows the % of PinX1 ubiquitylation in the presence of specific N-end rule inhibitors compared to the reaction in the absence of the inhibitors. FIGS. 9(A) and (B) show that the mixture of Arg-β-Ala and Trp-Ala dipeptides and Arg-β-Ala alone (Type I inhibitor) inhibit PinX1 ubiquitylation to a similar extent, while Trp-Ala alone (Type II inhibitor) has no effect. These results identify PinX1 as a Type I substrate for an N-end rule ubiquitylation pathway.

Example 9

HMGN3 is an N-End Rule Ubiquitylation Substrate

HMGN3 was produced using IMAGE clones #3890883 and #4749335 and analyzed for its ability to act as an N-end rule substrate by ECL assay as described in Materials and Methods.

FIGS. 10 (A) and (C) show the time course of the accumulation of ubiquitylated HMGN3 encoded by clones #3890883 and #4749335, respectively. FIGS. 10 (B) and (D) (HMGN3 encoded by clones #3890883 and #4749335 respectively) show the % of HMGN3 ubiquitylation in the presence of specific N-End Rule inhibitors compared to the reaction in the absence of the inhibitors. FIG. 10 shows that the mixture of Arg-β-Ala and Trp-Ala dipeptides and Arg-β-Ala alone (Type I inhibitor) inhibit HMGN3 ubiquitylation to a greater extent, while Trp-Ala alone (Type II inhibitor) has little effect. The effect is most pronounced for clone #4749335 (FIG. 10 (C-D)). These results identify HMGN3 as a Type I substrate for an N-end rule ubiquitylation pathway.

Example 10

CBF1-Interacting Protein (CIR) is an N-End Rule Ubiquitylation Substrate

CIR was produced using IMAGE clone #3910222 and analyzed for its ability to act as an N-end rule substrate by ECL assay as described in the Materials and Methods.

Figure 11B:
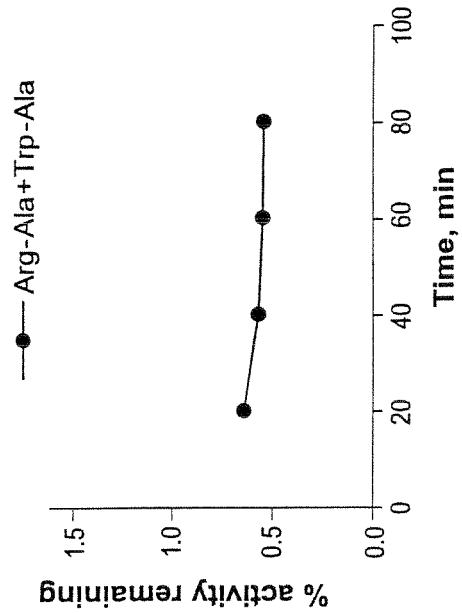
FIG. 11 shows (A) the time course for an ECL assay for N-end rule ubiquitylation of CIR and (B) the % inhibition of the ECL signal in the presence of N-end rule inhibitors.
Figure 11A:
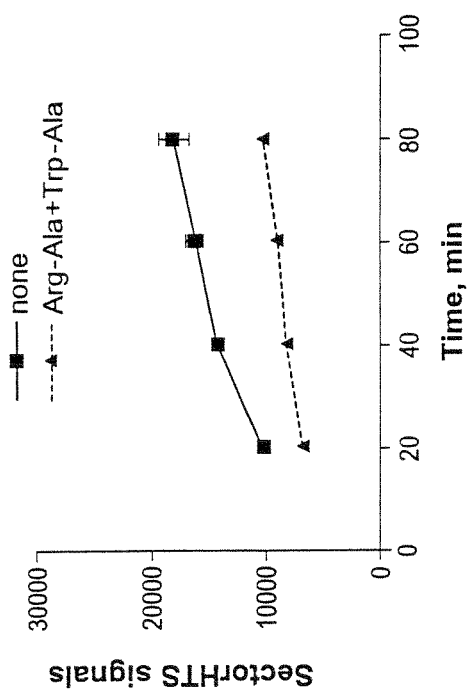

FIG. 11 (A) shows the time course of the accumulation of ubiquitylated CIR. FIG. 11 (B) shows the % of CIR ubiquitylation in the presence of a mixture of N-End Rule inhibitors compared to the reaction in the absence of the inhibitors. The FIG. 11 shows that CIR is a substrate for an N-end rule ubiquitylation pathway.

What is claimed is:

1. An isolated activated fragment of a protein, said fragment having an exposed N-degron, wherein said protein has a hidden N-degron and is selected from the group consisting of apataxin, SLP, HMG17, PinX1, CIR, Cullin 3, HMGN3, HSPC144 and CDC6 and fragments thereof.

2. A composition comprising an isolated activated fragment of a protein having an exposed N-degron, wherein said protein is selected from the group consisting of aprataxin, SLP, HMG17, PinX1, CIR, Cullin 3, HMGN3, HSPC144 and CDC6 and fragments thereof, wherein the concentration of said activated fragment is at least two-fold greater than the concentration of activated fragment from a natural source.

3. A composition comprising the activated fragment of claim 1, wherein said activated fragment is immobilized on a support and/or linked to a label.

4. The activated fragment of claim 1, wherein said activated fragment is further subjected to a proteolysis which removes a C-terminal portion of said activated fragment.

* * * * *